(12) United States Patent
Larsen

(10) Patent No.: US 12,390,600 B2
(45) Date of Patent: Aug. 19, 2025

(54) DRUG DELIVERY DEVICE FOR DELIVERING A PREDEFINED FIXED DOSE

(71) Applicant: Novo Nordisk A/S, Bagsvaerd (DK)

(72) Inventor: Bjoern Gullak Larsen, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 714 days.

(21) Appl. No.: 17/780,276

(22) PCT Filed: Dec. 9, 2020

(86) PCT No.: PCT/EP2020/085201
§ 371 (c)(1),
(2) Date: May 26, 2022

(87) PCT Pub. No.: WO2021/122190
PCT Pub. Date: Jun. 24, 2021

(65) Prior Publication Data
US 2022/0409821 A1    Dec. 29, 2022

(30) Foreign Application Priority Data
Dec. 18, 2019    (EP) .................................... 19217339

(51) Int. Cl.
*A61M 5/315*    (2006.01)
*A61M 5/32*    (2006.01)
(52) U.S. Cl.
CPC .... *A61M 5/31595* (2013.01); *A61M 5/31536* (2013.01); *A61M 5/31583* (2013.01); *A61M 5/31593* (2013.01); *A61M 5/3202* (2013.01)
(58) Field of Classification Search
CPC .......... A61M 5/31536; A61M 5/31595; A61M 5/31593; A61M 2005/2013;
(Continued)

(56) References Cited

U.S. PATENT DOCUMENTS 9,017,293 B2    4/2015    Edhouse et al.
9,138,542 B2    9/2015    Smith
(Continued)

FOREIGN PATENT DOCUMENTS

EP        3108914 A1    12/2016
JP    2002534229 A    10/2002
(Continued)

OTHER PUBLICATIONS

European Application No. EP18203370.4 filed Oct. 30, 2018.

*Primary Examiner* — Jason E Flick
*Assistant Examiner* — Isabella S North
(74) *Attorney, Agent, or Firm* — Wesley Nicolas

(57) ABSTRACT

A drug delivery device (100, 200) for delivering a fixed dose, wherein the drug delivery device comprises: a housing assembly, a drug reservoir with a piston and a drive mechanism. The drive mechanism comprises a piston rod (109, 209) for advancing the piston to expel a drug, and a drive tube (180, 280), wherein the drive mechanism is adapted to deliver the predefined fixed dose in response to activation. The drug delivery device further comprises an activation mechanism for activating the drive mechanism, in response to moving the drive tube in an axial direction. The housing assembly comprises a guide structure for guiding the drive tube during activation and delivery of a dose, wherein the guide structure comprises an axial portion (156, 256) providing a sliding surface for guiding the drive tube during activation, and for providing a rotational stop defining an end of dose, and a helical portion (157, 257) providing a sliding surface adapted for guiding the drive tube (180, 280) during dosing. The drive tube (180, 280) comprises a guide structure comprising an axial portion (182, 282) adapted for slidably engaging the axial portion of the housing assembly for activation, and a helical portion (189, 289) for slidably (Continued)

engaging the helical portion of the housing assembly during dosing during dosing.

15 Claims, 35 Drawing Sheets

(58) Field of Classification Search
CPC ............ A61M 5/31583; A61M 5/3202; A61M 2005/202; A61M 5/3204; A61M 2005/3267; A61M 5/31563; A61M 5/3153; A61M 5/20
USPC ........................................................ 604/155
See application file for complete search history.

(56) References Cited

U.S. PATENT DOCUMENTS

| | | |
|---|---|---|
| D749,719 S | 2/2016 | Sanders et al. |
| 2002/0016571 A1 | 2/2002 | Kirchhofer et al. |
| 2004/0035491 A1* | 2/2004 | Castellano ............... A61M 5/30 141/27 |
| 2014/0221936 A1 | 8/2014 | Edhouse et al. |
| 2014/0228769 A1 | 8/2014 | Karlsson et al. |
| 2014/0257194 A1* | 9/2014 | Edhouse ............ A61M 5/3232 604/198 |
| 2017/0148354 A1 | 5/2017 | Baker et al. |
| 2018/0117240 A1 | 5/2018 | Archilla et al. |
| 2019/0015595 A1 | 1/2019 | Keitel |

FOREIGN PATENT DOCUMENTS

| | | | |
|---|---|---|---|
| JP | 2014527894 A | 10/2014 | |
| WO | 94/26331 A1 | 11/1994 | |
| WO | 04108194 A1 | 12/2004 | |
| WO | 2011039206 A2 | 4/2011 | |
| WO | 2011/111006 A2 | 9/2011 | |
| WO | 2012117255 A1 | 9/2012 | |
| WO | 2013034647 A1 | 3/2013 | |
| WO | 2013034651 A1 | 3/2013 | |
| WO | 2013034986 A2 | 3/2013 | |
| WO | 17064275 A1 | 4/2017 | |
| WO | 2017106221 A1 | 6/2017 | |
| WO | WO-2017098460 A1 * | 6/2017 | ............. A61M 5/20 |
| WO | 2017144601 | 8/2017 | |
| WO | 2018007259 A2 | 1/2018 | |
| WO | 2018215270 A2 | 11/2018 | |
| WO | 2018215271 A1 | 11/2018 | |
| WO | 201909179 A1 | 1/2019 | |
| WO | 2019011394 A1 | 1/2019 | |
| WO | 2019011688 A1 | 1/2019 | |
| WO | 2020089167 A1 | 5/2020 | |

* cited by examiner

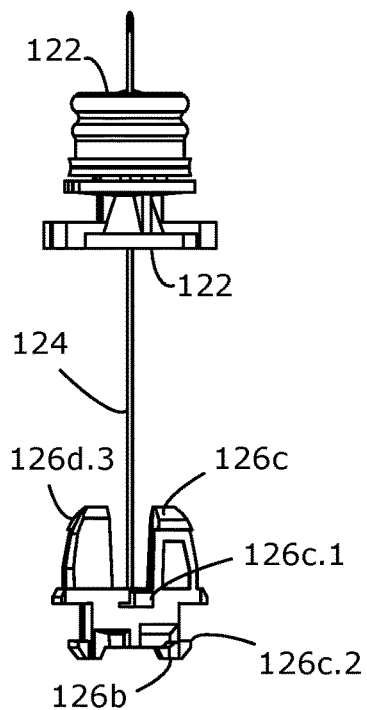
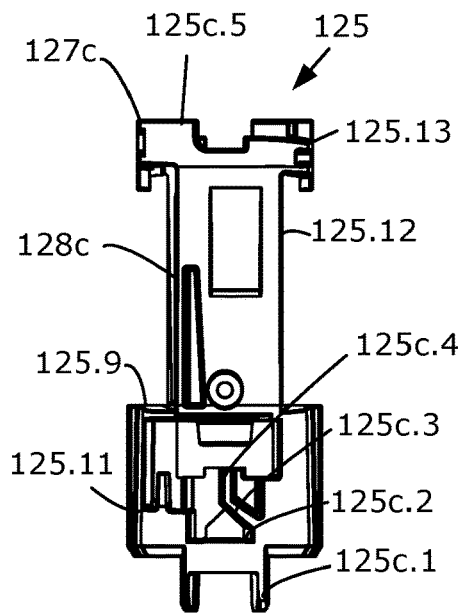
Fig. 1D    Fig. 1E
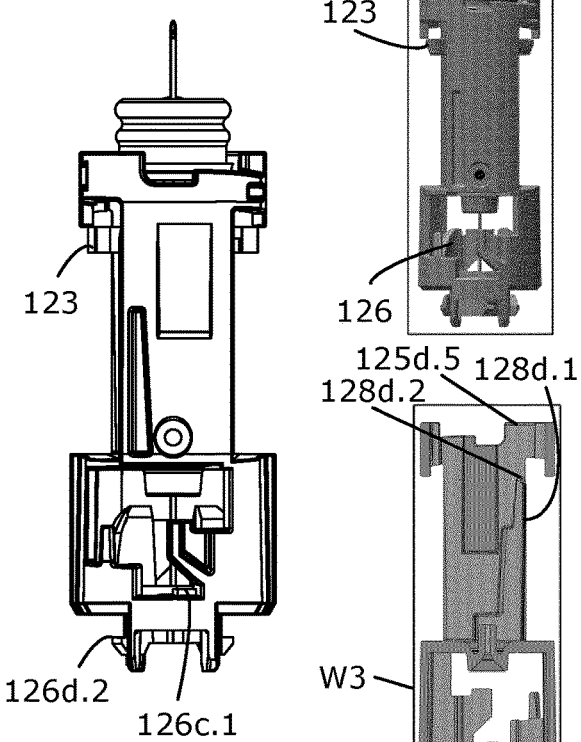
Fig. 1F

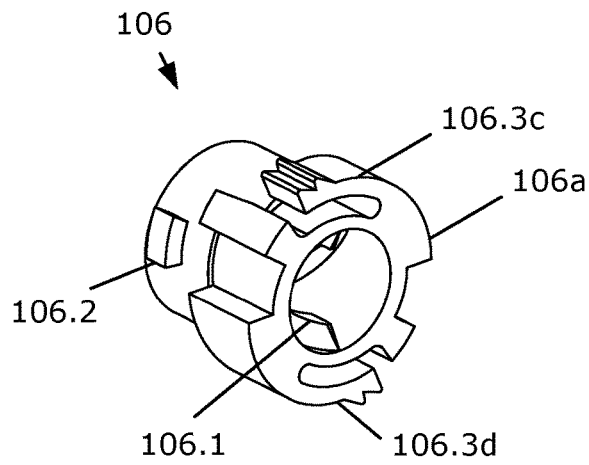
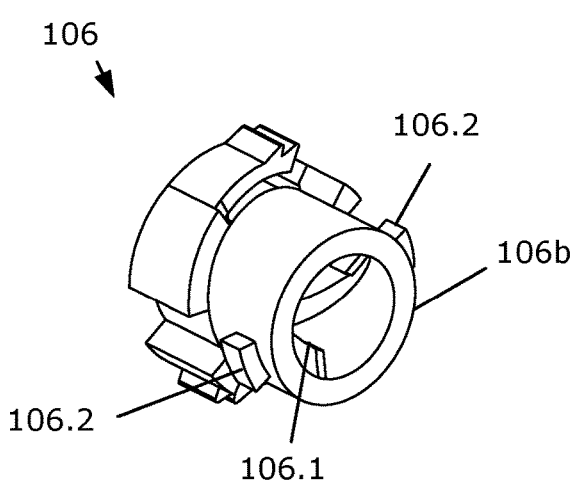
Fig. 4A
Fig. 4B
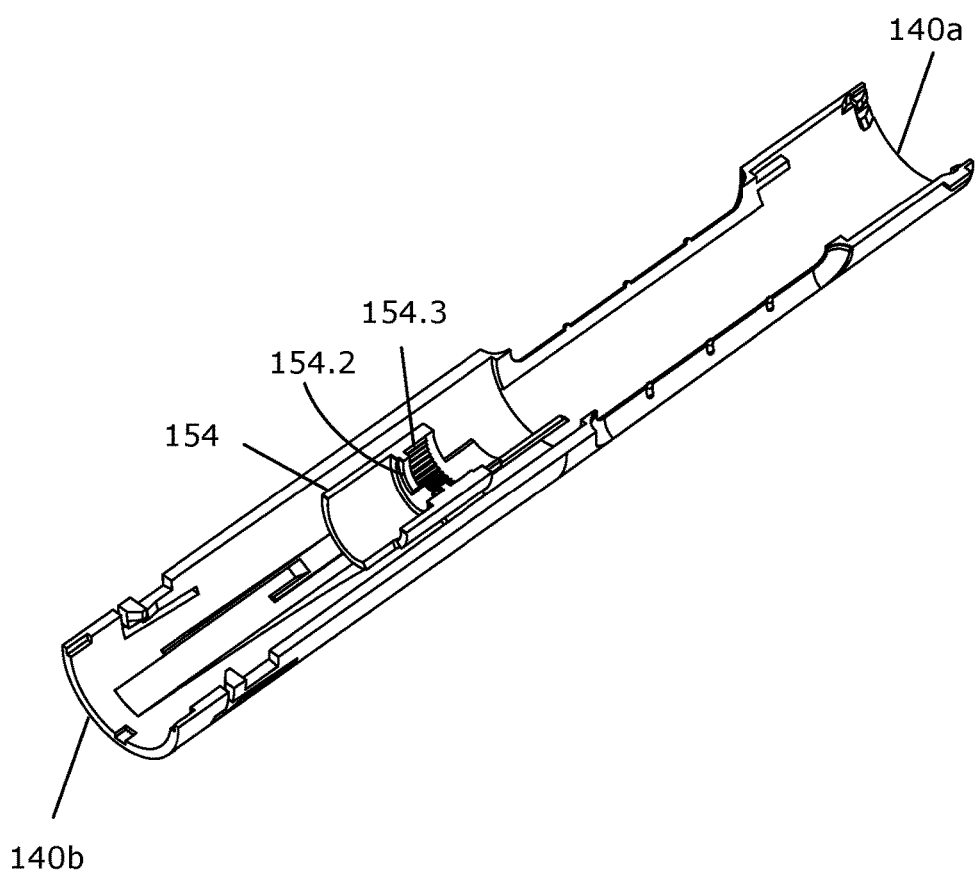
Fig. 5

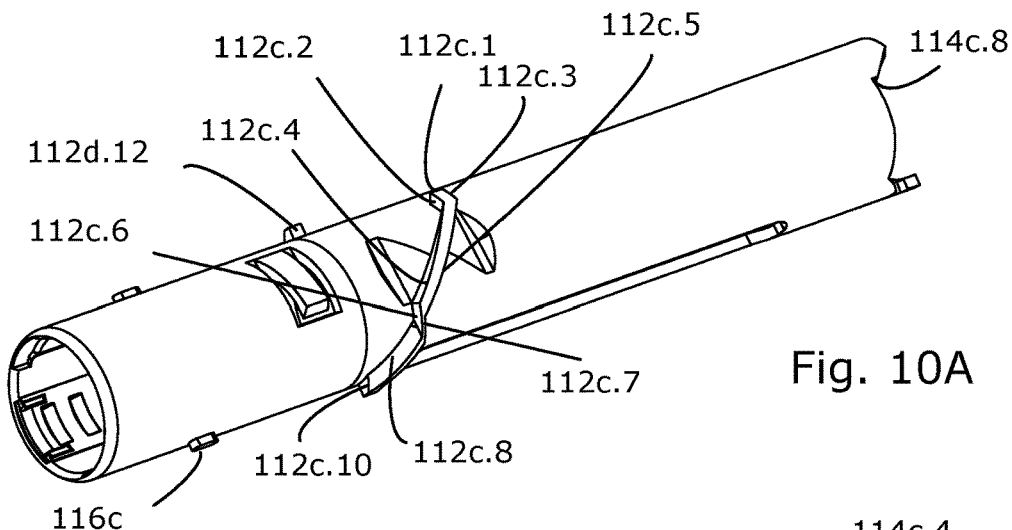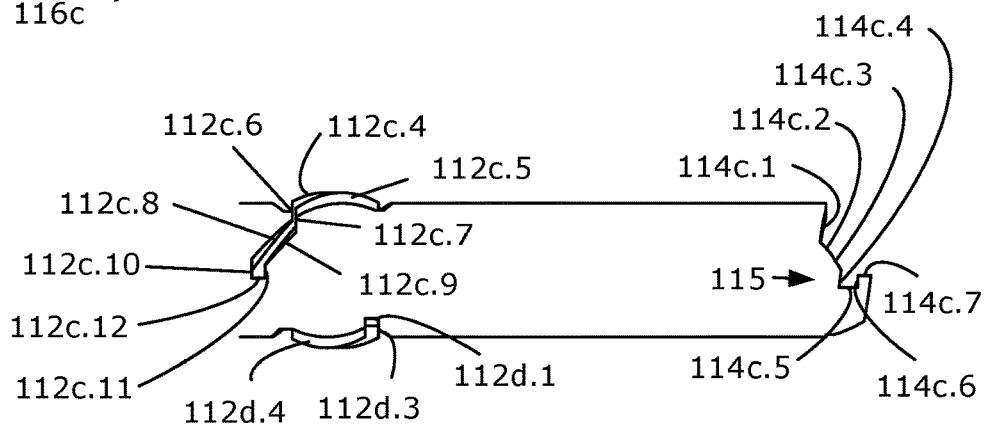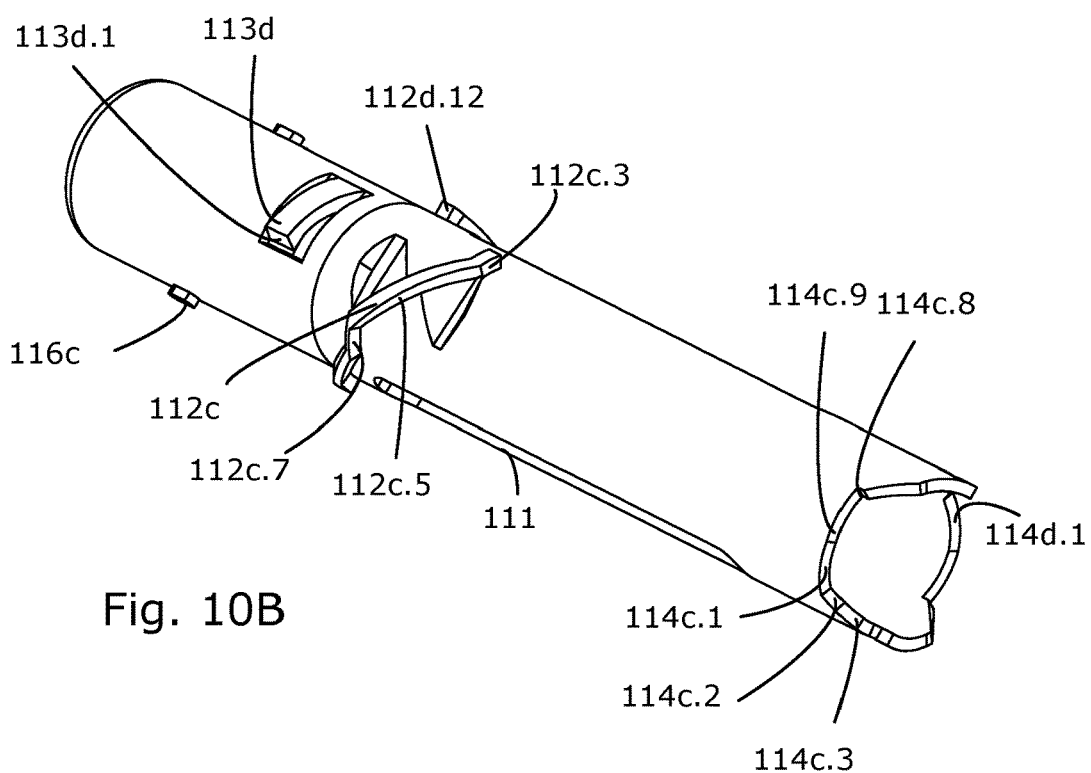

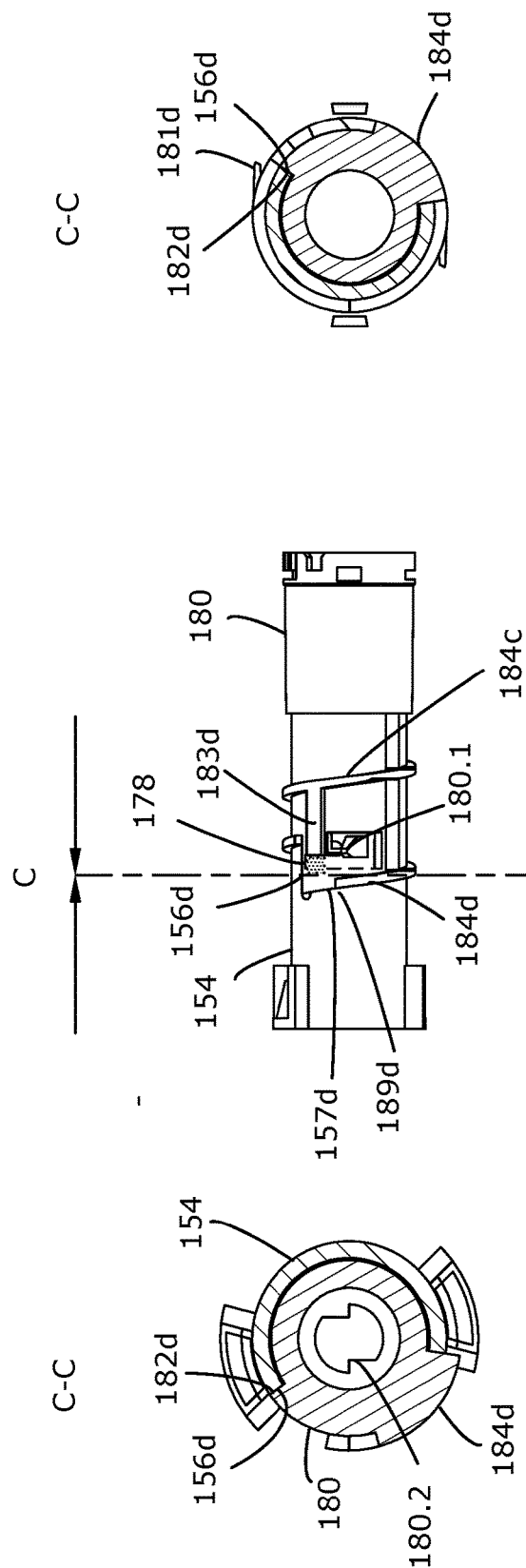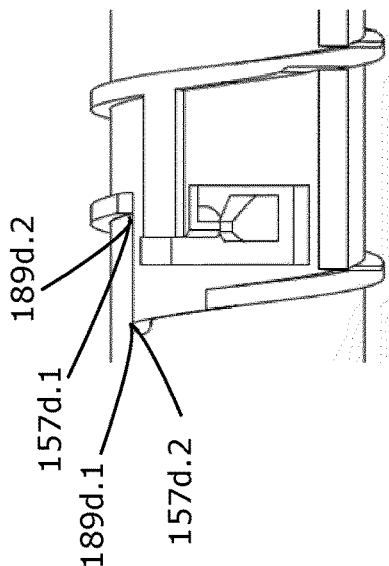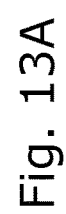
Fig. 13C
Fig. 13D
Fig. 13A
Fig. 13B

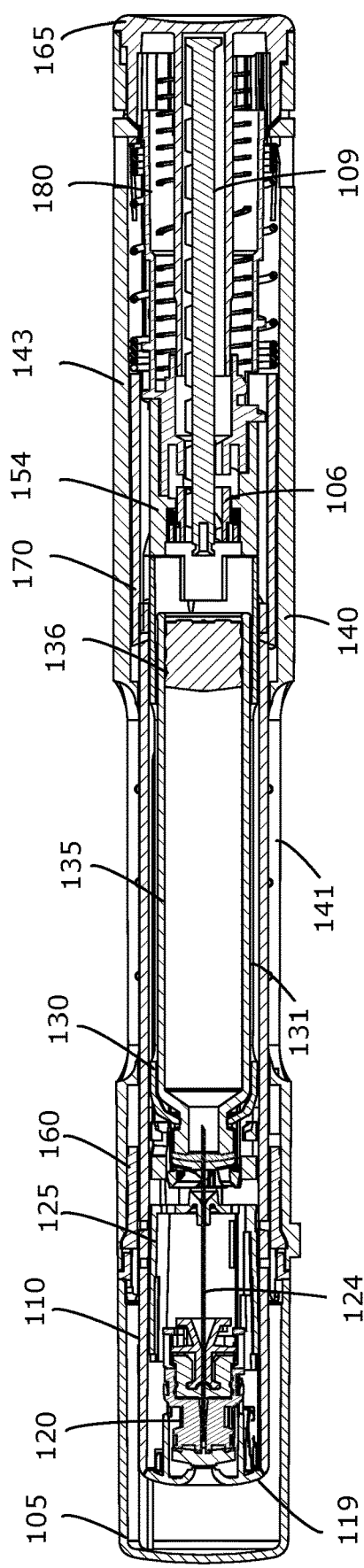
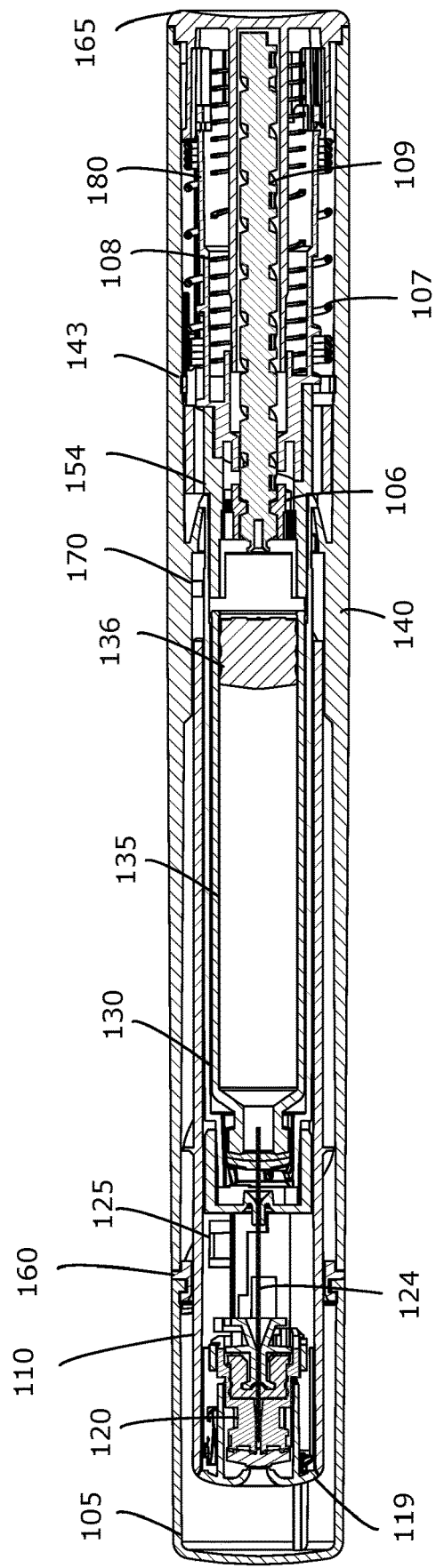
Fig. 14A
Fig. 14B

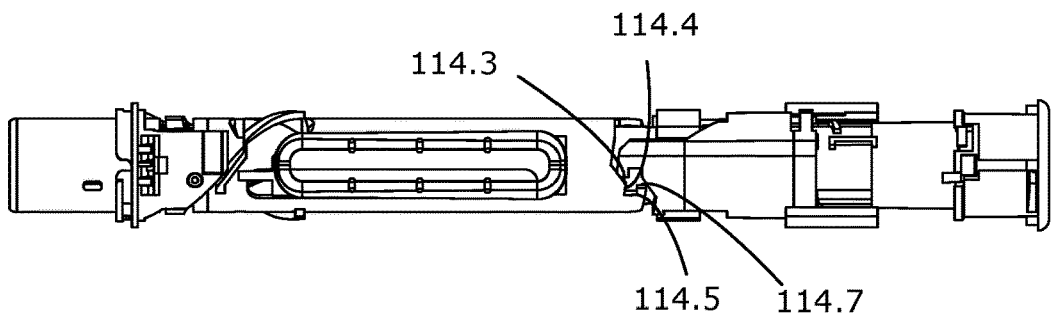
Fig. 16I
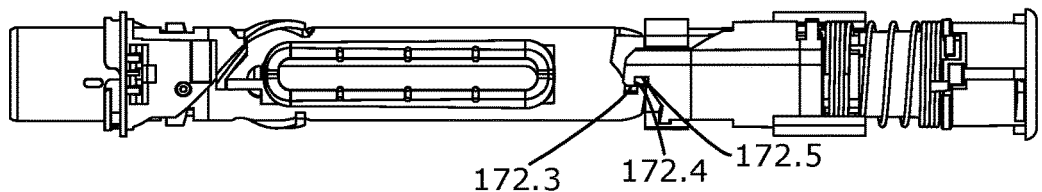
Fig. 16J
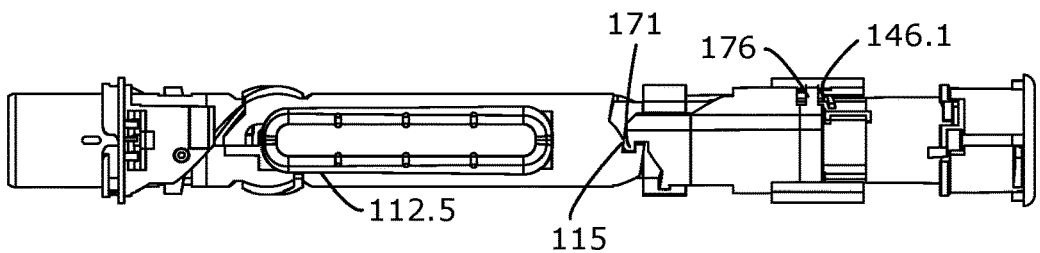
Fig. 16K1
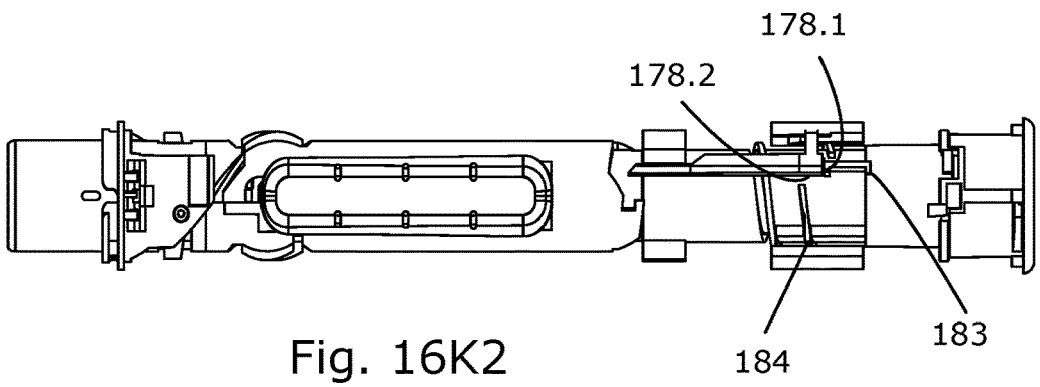
Fig. 16K2

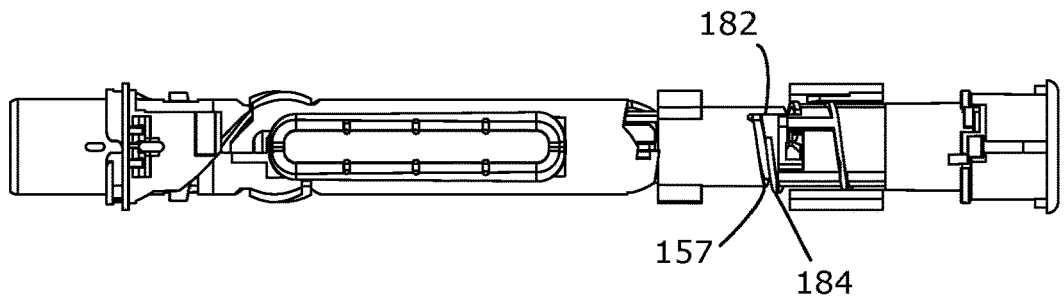
Fig. 16K3
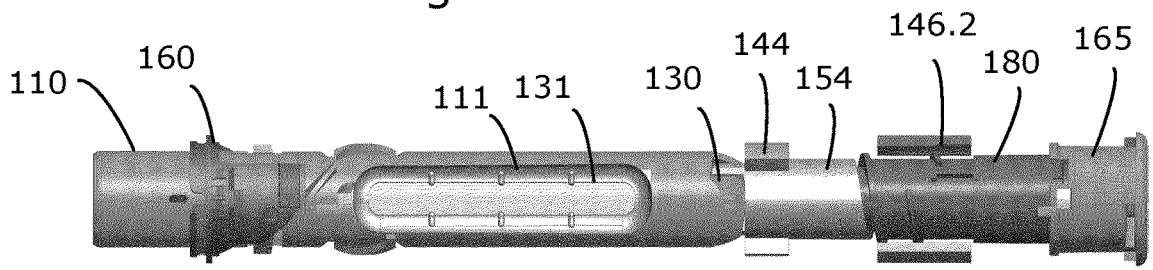
Fig. 16K4
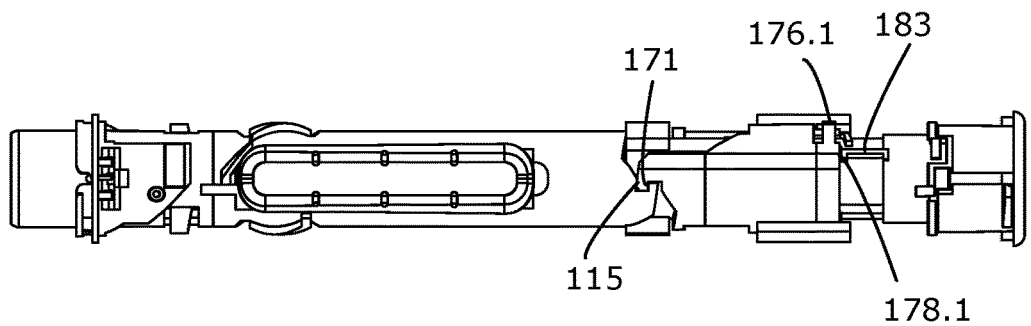
Fig. 16L1
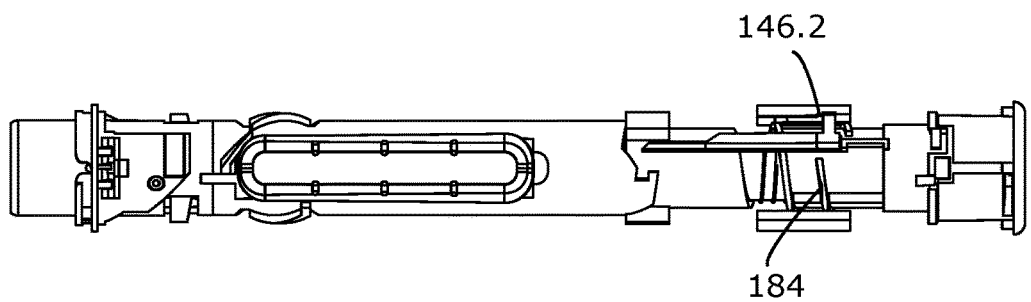
Fig. 16L2

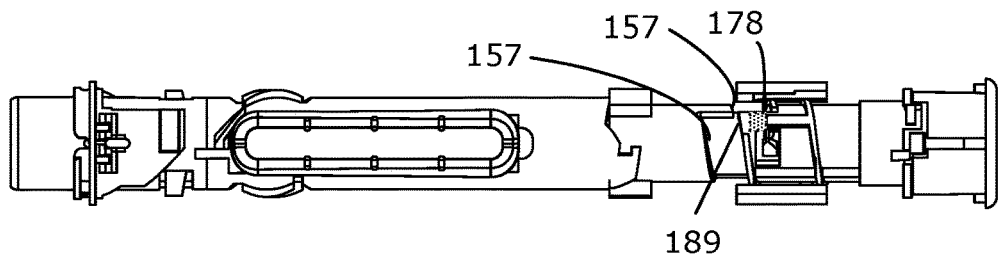
Fig. 16L3
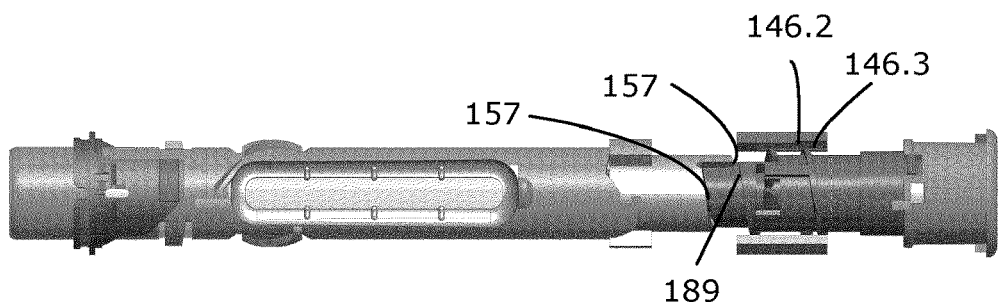
Fig. 16L4
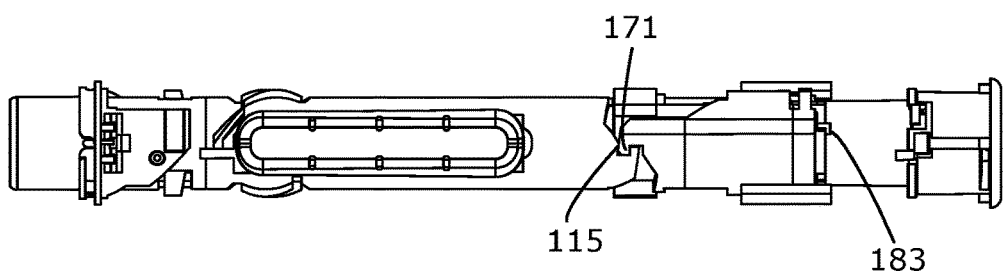
Fig. 16M1
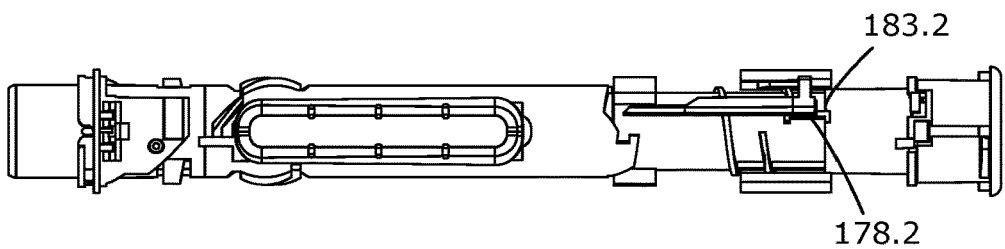
Fig. 16M2

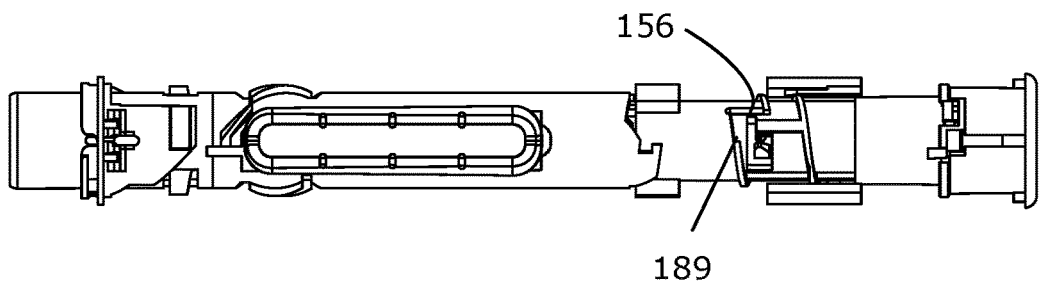
Fig. 16M3
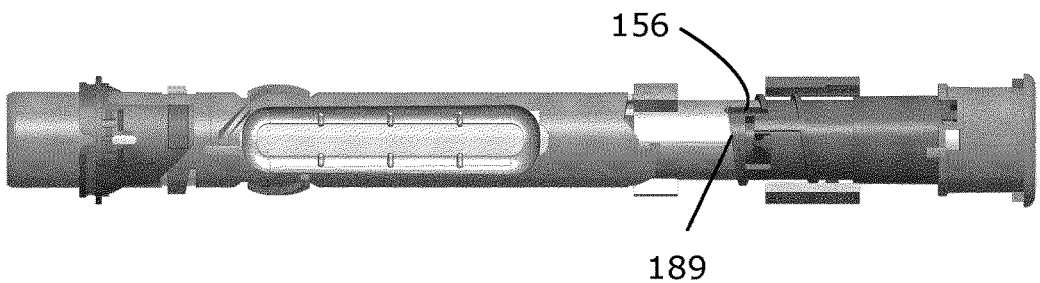
Fig. 16M4
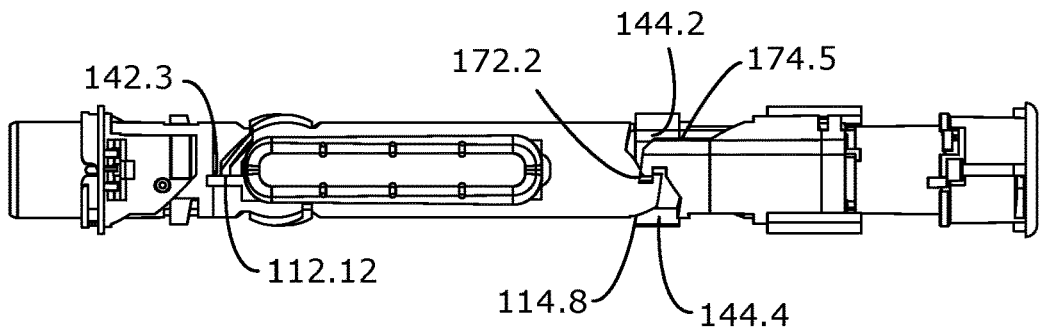
Fig. 16N1
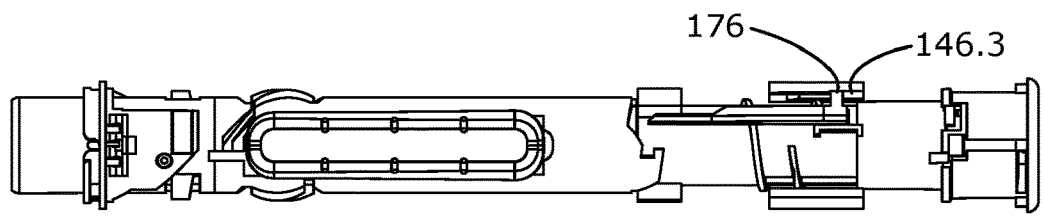
Fig. 16N2

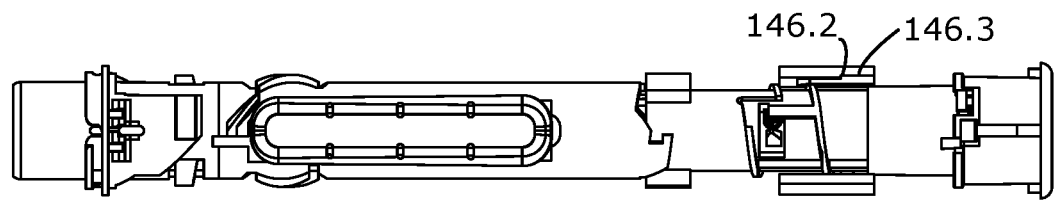
Fig. 16N3
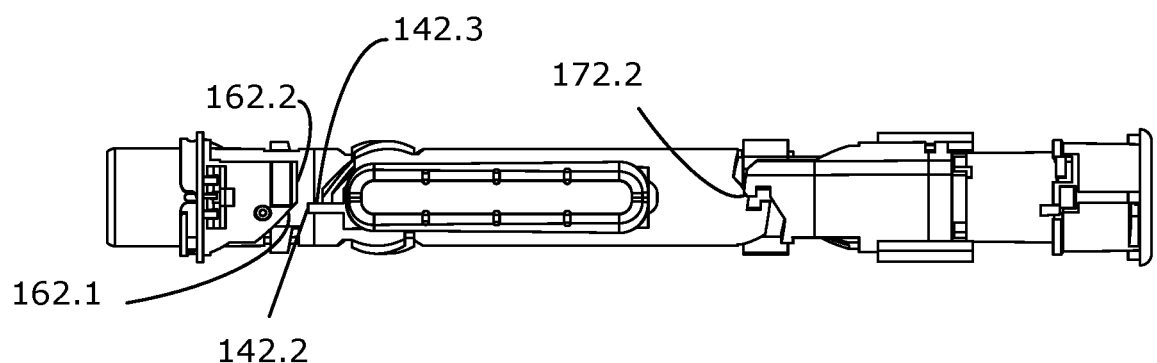
Fig. 16O
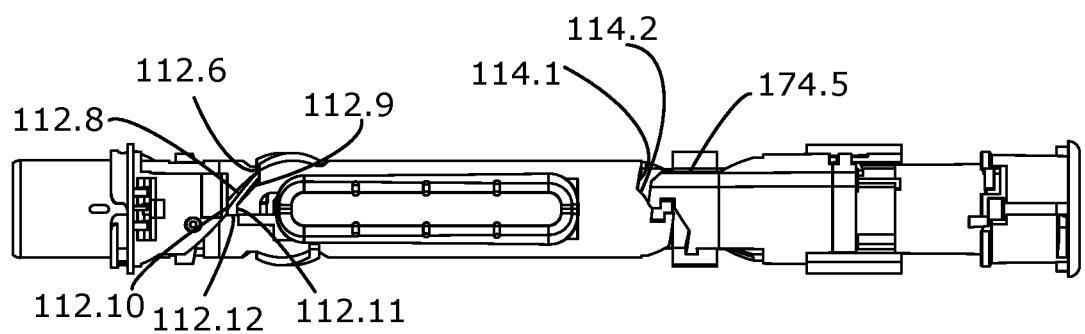
Fig. 16P

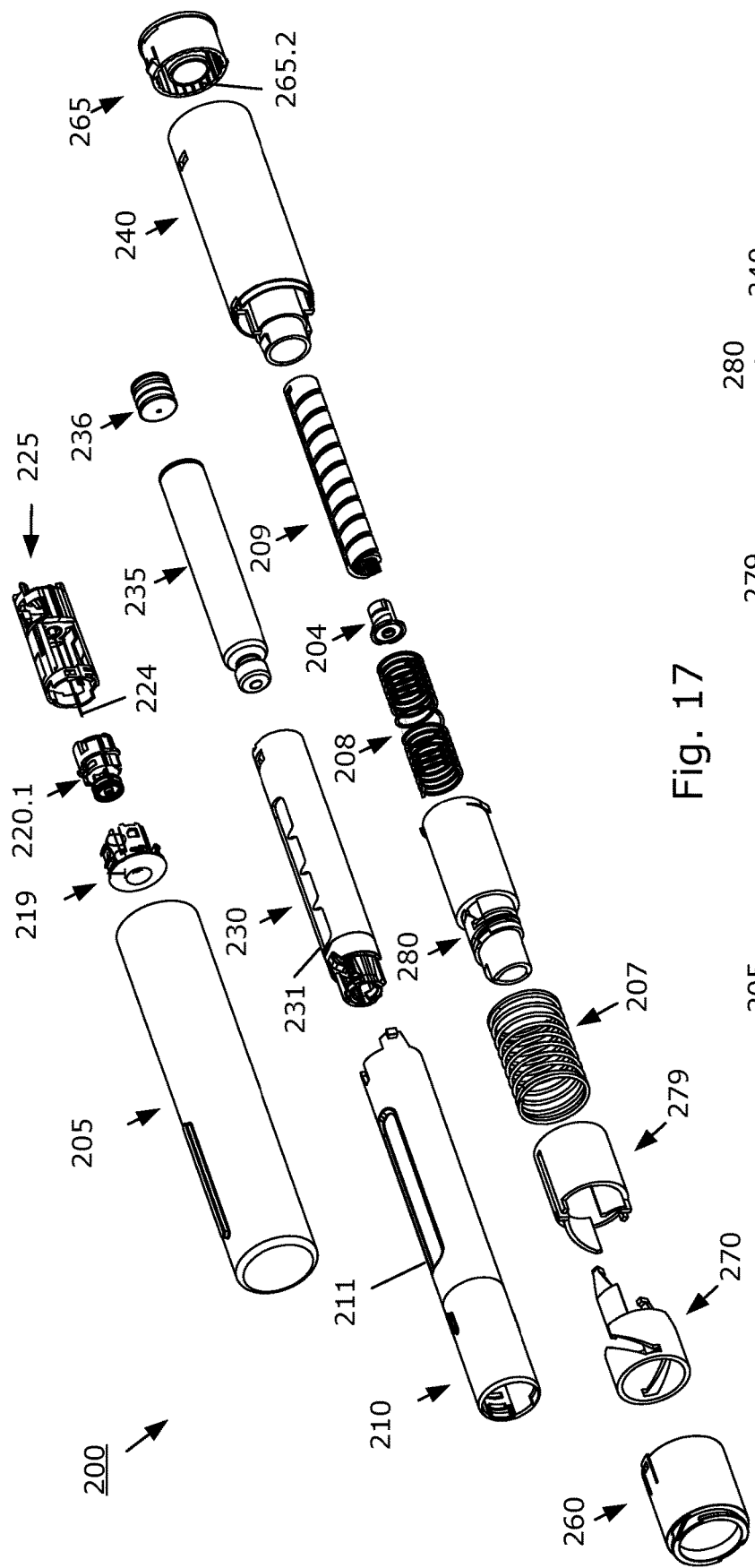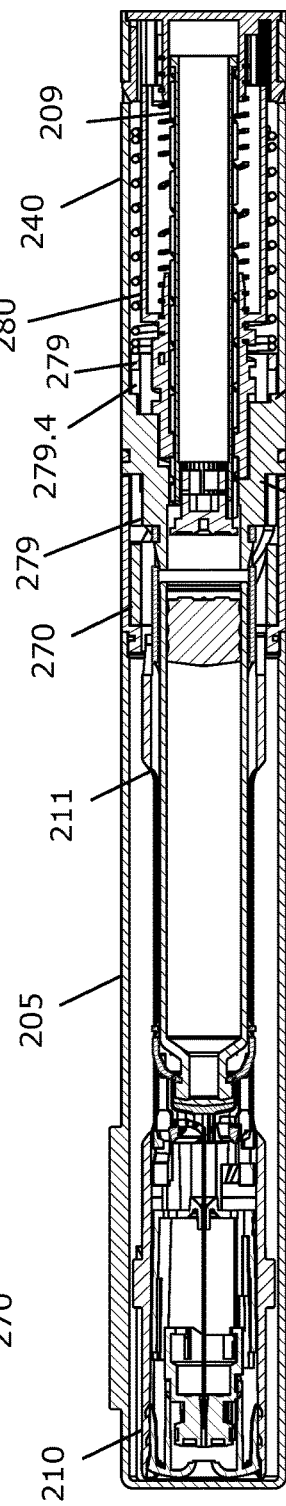

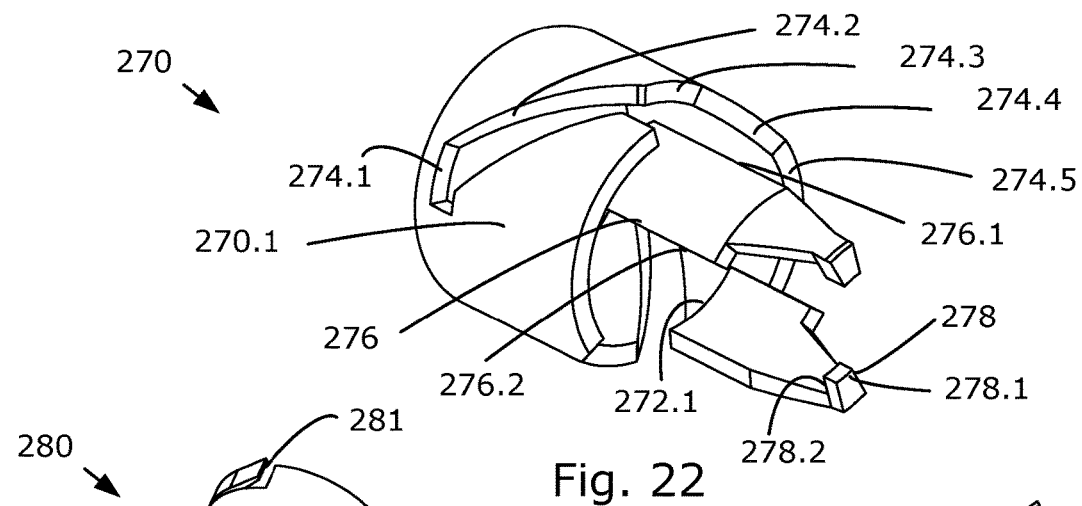
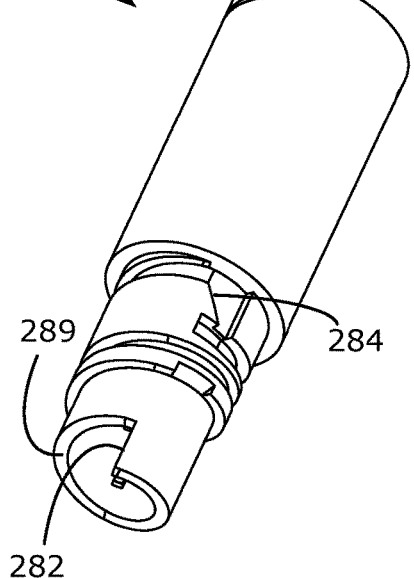
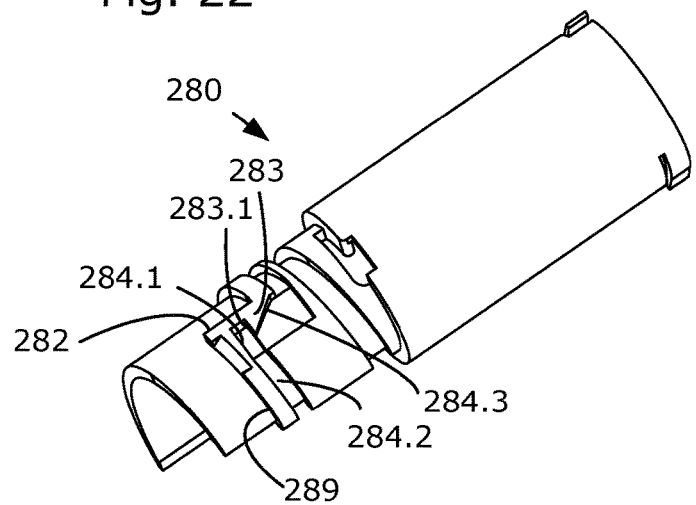
Fig. 22
Fig. 23A
Fig. 23B
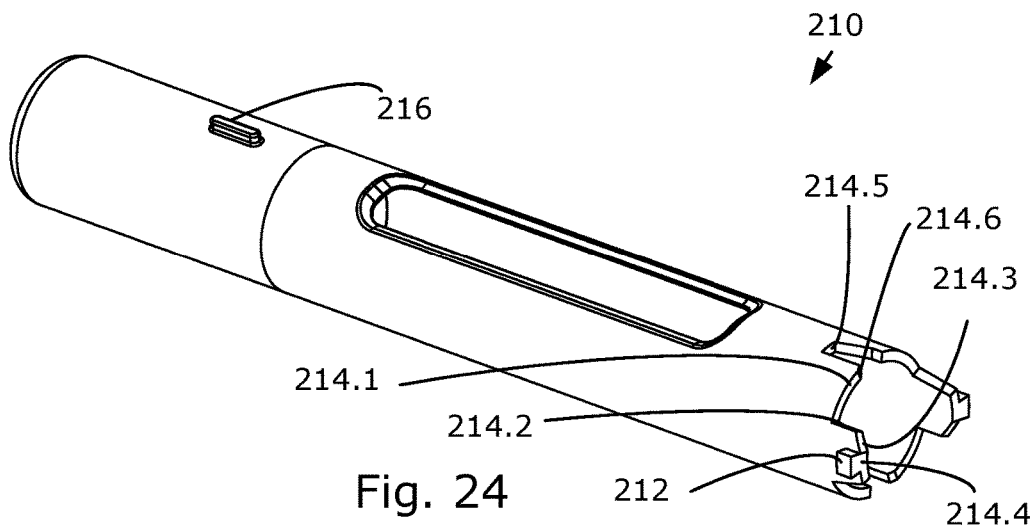
Fig. 24

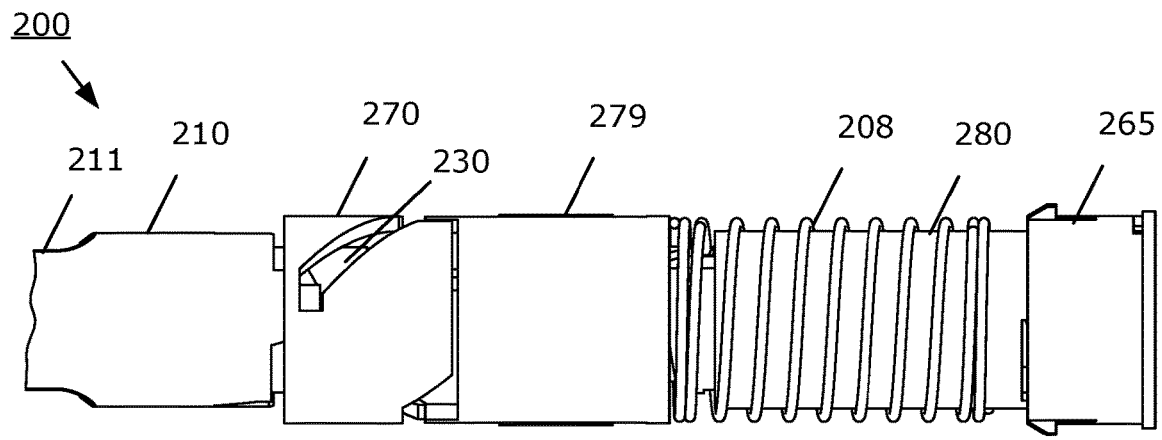
Fig. 25A1
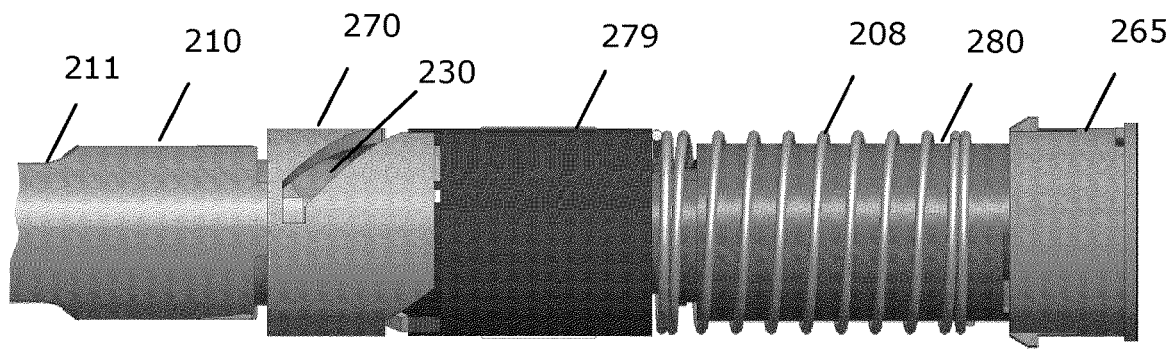
Fig. 25A2

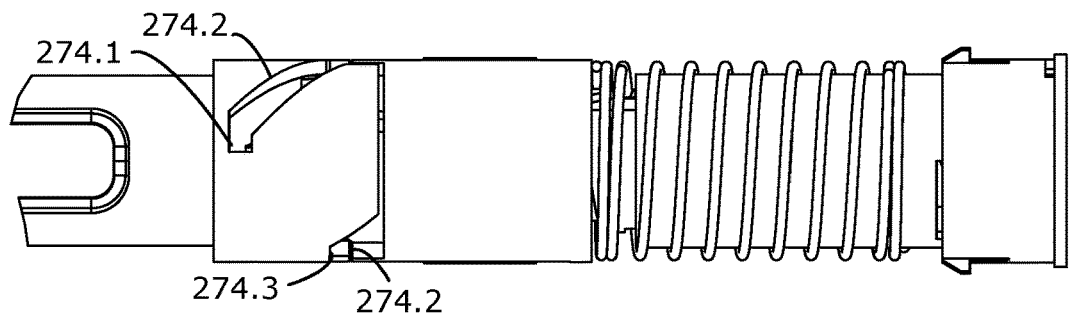
Fig. 25B1
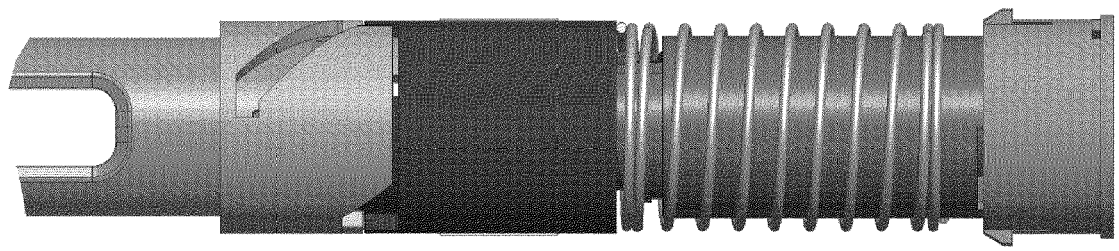
Fig. 25B2
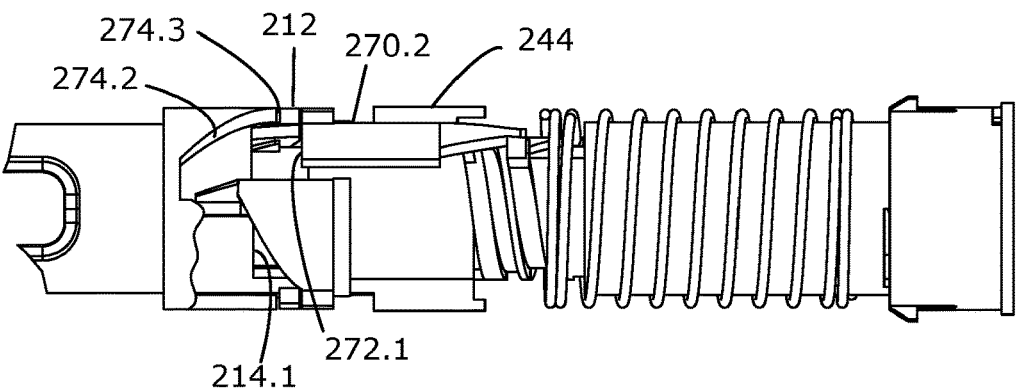
Fig. 25B3
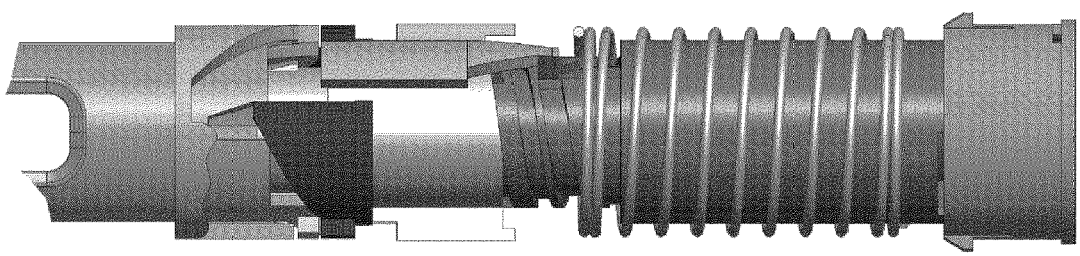
Fig. 25B4

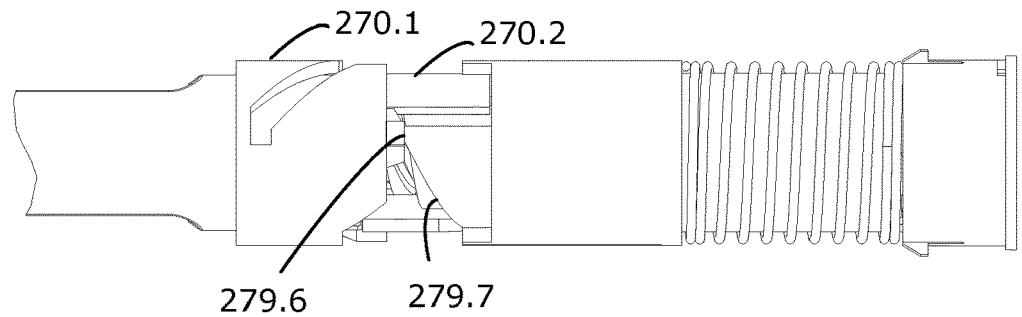
Fig. 25C1
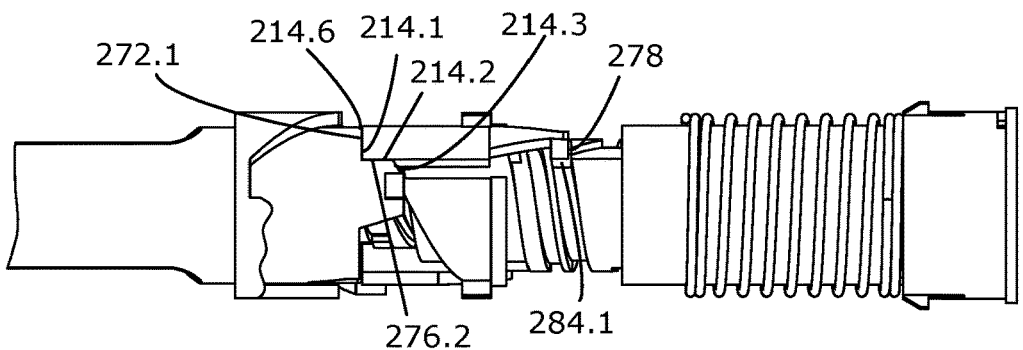
Fig. 25C2
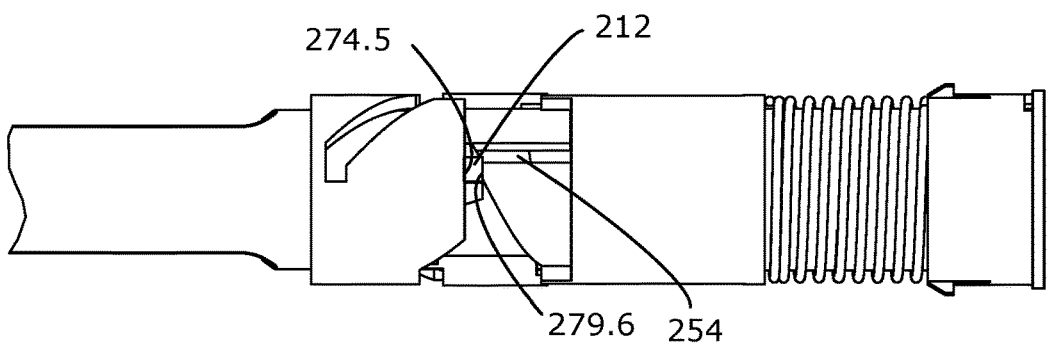
Fig. 25D1
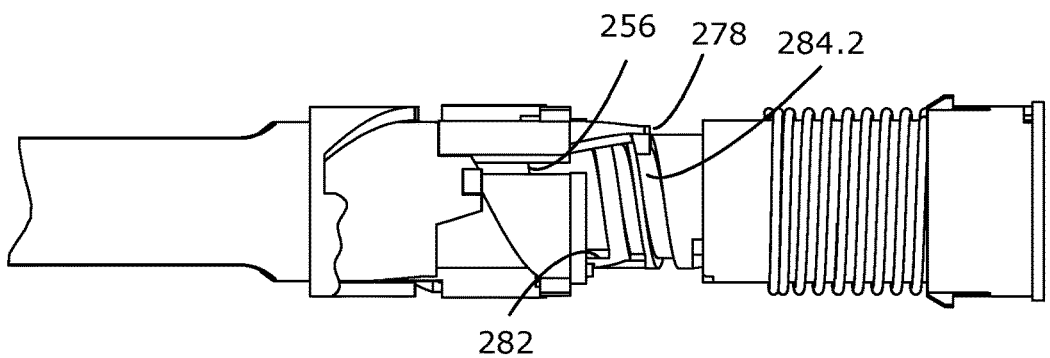
Fig. 25D2

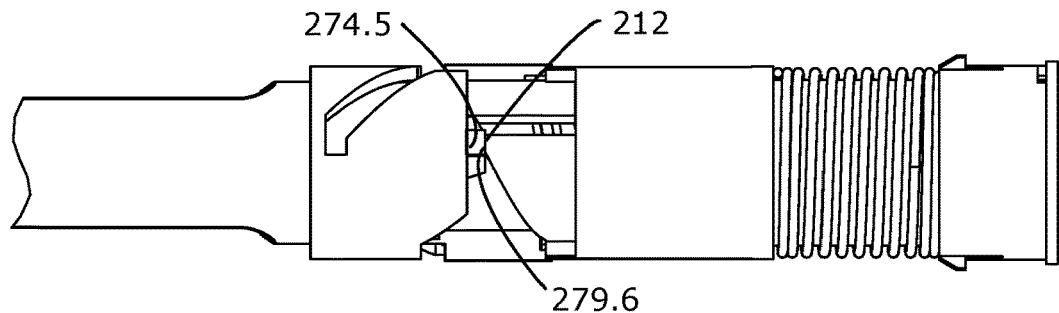
Fig. 25E1
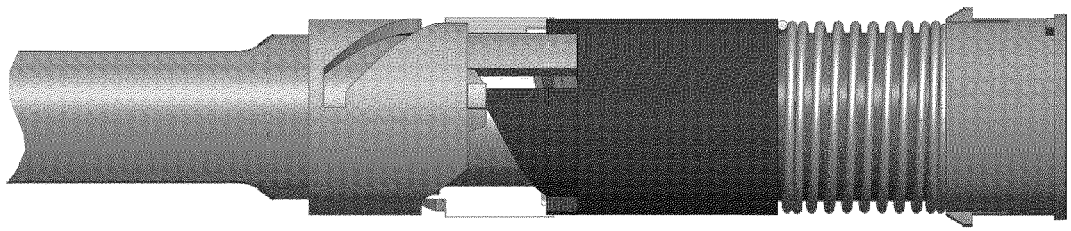
Fig. 25E2
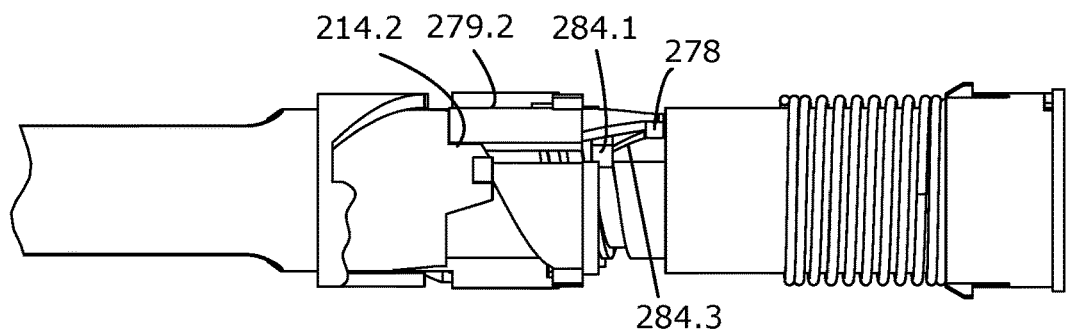
Fig. 25E3
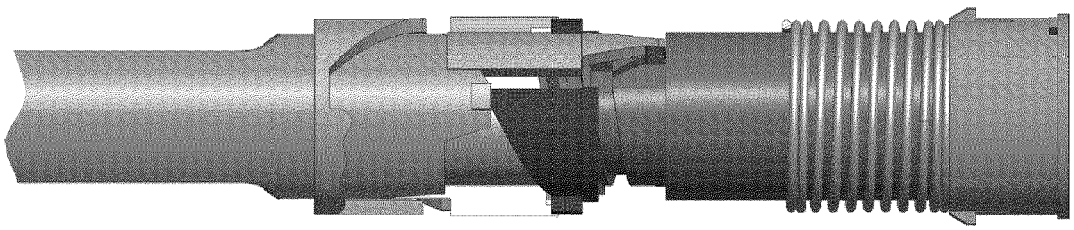
Fig. 25E4

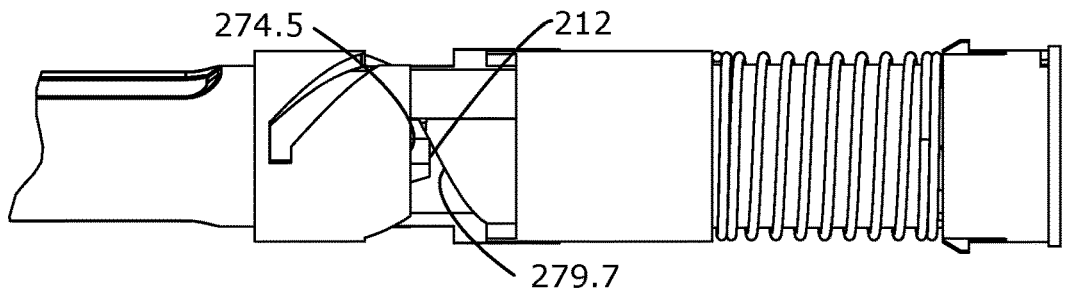
Fig. 25F1
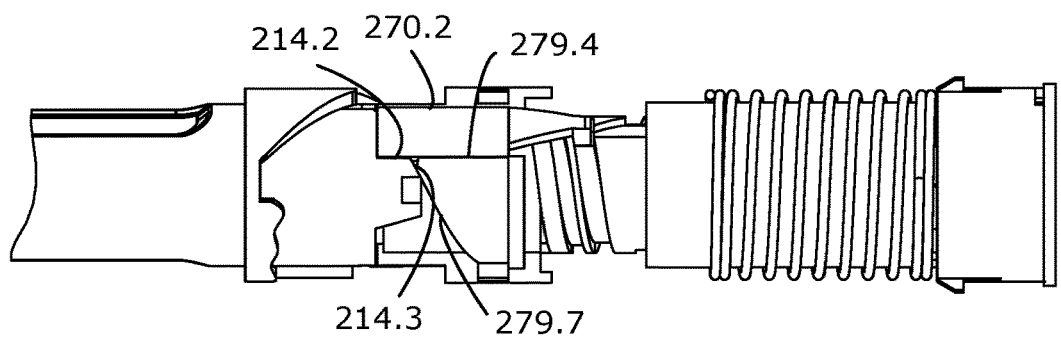
Fig. 25F2
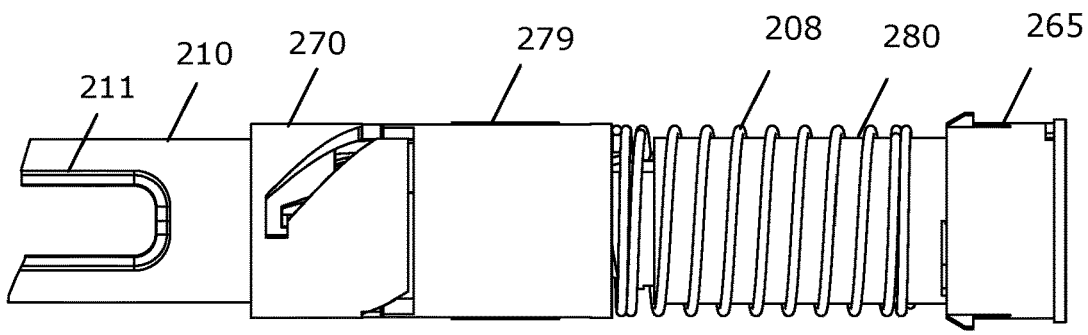
Fig. 25G1
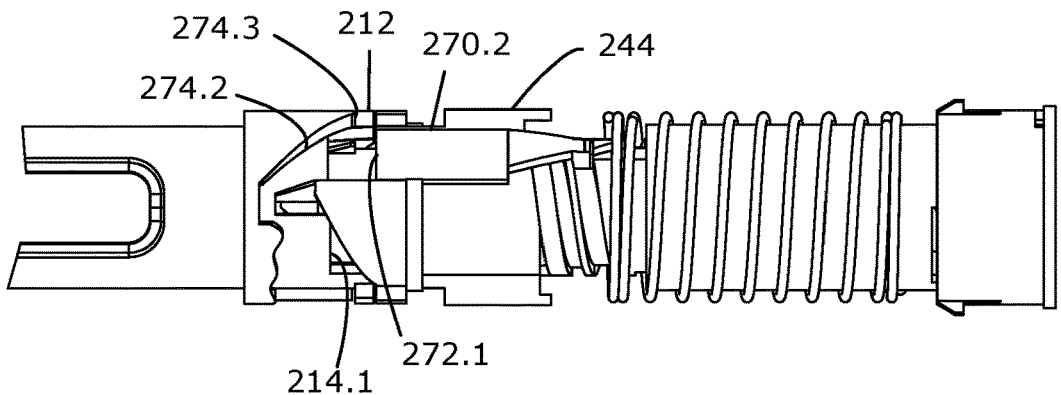
Fig. 25G2

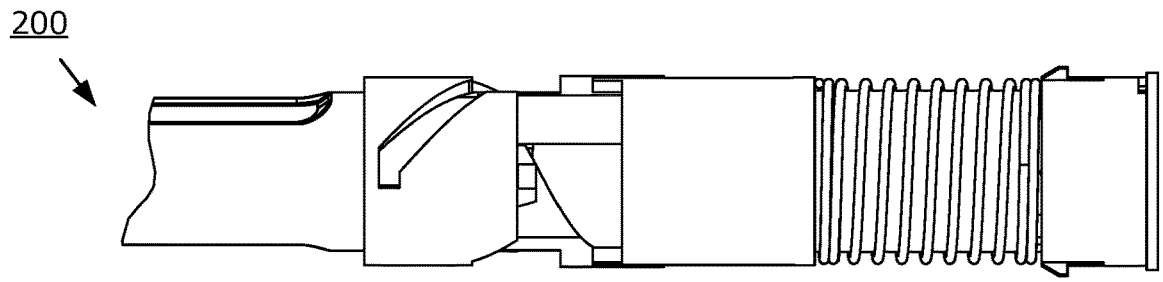
Fig. 26A1
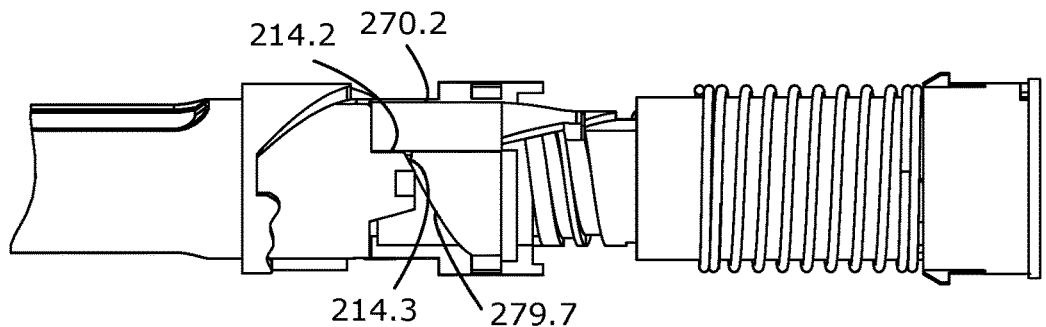
Fig. 26A2
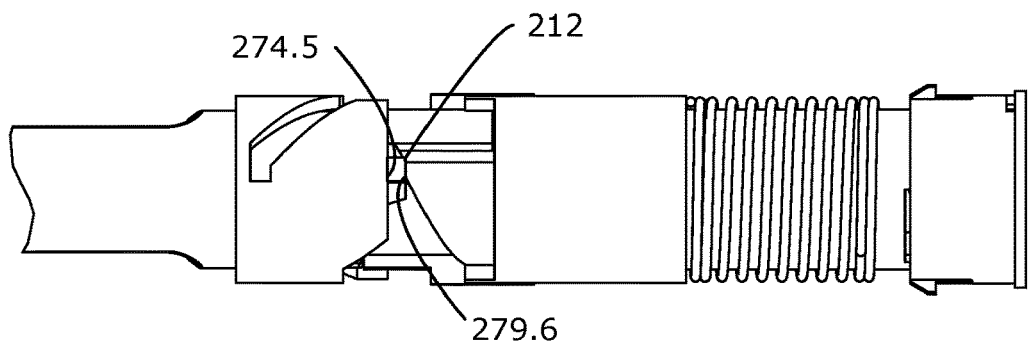
Fig. 26B1
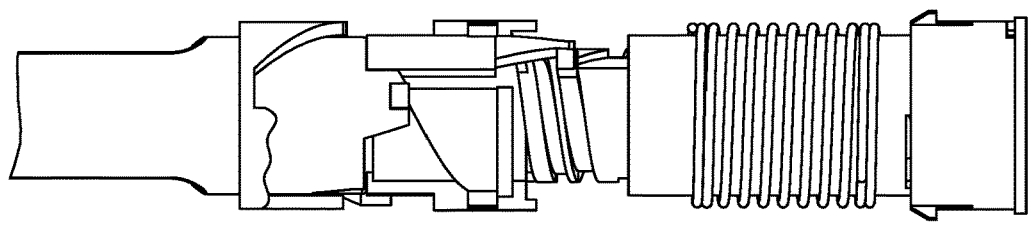
Fig. 26B2

DRUG DELIVERY DEVICE FOR DELIVERING A PREDEFINED FIXED DOSE

CROSS-REFERENCE TO RELATED APPLICATIONS

This application is a 35 U.S.C. § 371 National Stage application of International Application PCT/EP2020/085201 (published as WO 2021/122190), filed Dec. 9, 2020, which claims priority to European Patent Application 19217339.1, filed Dec. 18, 2019; the contents of which are incorporated herein by reference.

The present invention relates to a drug delivery device for delivering a fixed dose. The present invention especially relates to such drug delivery device comprising a drive mechanism with helical and axial guiding portions.

BACKGROUND OF THE INVENTION

Drug delivery devices for self-administration of different liquid drug formulation presently exist in various shapes and sizes. Some are adapted for connecting to an infusion set, and some are connectable or integrated with an injection needle. The latter type is referred to as injection devices. Some are durable devices comprising a cartridge with a drug reservoir, wherein the cartridge can be changed. Others are disposable devices that are discarded when the cartridge is empty. Disposable devices can be either multi-dose devices, in which the user can set the desired dose size prior to each injection, or single dose devices, capable of administering only a single dose of a given size. The latter exists with so-called "Shield activation", where the cannula is covered by a shield in the front of the device that releases the dose when pressed. The cannula is then exposed only to enter the skin, when the user presses the device against the skin, and thereby depresses the shield, and releases the dose. These injection devices are disposed after a single injection.

Fixed dose devices are preferable to some users, since they may not feel comfortable with or be capable of operating the device to adjust the correct dose each time. When devices for instance are used by children or older people, simplicity and ease of use is important to avoid user error leading to over- or under dosing. In other cases, the treatment regimen prescribes a fixed dose of e.g. a GLP-1 type of drug.

However, the device itself is responsible for a considerably part of the costs of the unit, not to mention the amount of materials used and thus necessary to dispose. It would therefore be desirable to make a fixed dose device capable of delivering multiple doses of a fixed volume.

In existing multi-dose devices, the motor consists of a spring being wound up when adjusting the dose. One solution is to make a normal multi-dose device where the maximum dose size is limited, so it is only possible to dial up to the fixed dose size. This would however introduce a risk that the user does not dial up sufficiently and thus gets a smaller dose than expected, this problem has been solved in WO2020089167 filed by Novo Nordisk, wherein a ratchet tube is locked to the housing until the full dose has been set and the drive mechanism has been released.

Another fixed dose device is disclosed in WO2019/09179 filed by Sanofi-Aventis. The disclosure relates to an injection device with a longitudinally displaceable dose tracker, providing an automated dose setting in accordance to a preselected size of a dose. The disclosed injection device comprises an elongated housing 10 extending along a longitudinal axis (z), a piston rod 20, 120 to operably engage with a piston 7 of a cartridge 6 filled with the medicament. The injection device further comprises a dose tracker 60, 150, 250, 350, 450, 550 selectively operably engageable with the piston rod 20, 120, wherein the dose tracker is proximally displaceable relative to the housing 10 from an initial position (i), see FIG. 25, towards at least a first activation position (a), see FIG. 26, for setting of the dose and wherein the dose tracker is distally displaceable relative to the housing (10) from the activation position (a) towards the initial position (i) for dispensing of the dose. The injection device comprises a spring 80, 144 to urge the dose tracker in the proximal direction. The injection device further comprises an interlock 84, 184, 284, 584 to lock the dose tracker in the initial position (i), and a release member 100, 101, 190, 290, 590 to release the interlock 84, 184, 284. For example, if the release member 190 is activated in order to liberate or to release the dose tracker 150 the dose tracker 150 starts to rotate relative to the housing under the action of the relaxing spring 144. An alternative fixed dose device wherein the size of the fixed dose can be selected is disclosed in WO 2017/106221 filed by Merch Sharp & Dohme Corp. However, enabling the possibility of selecting between different sizes of fixed doses adds to the complexity of the device and the selection functionality is not always desirable. The functionality of providing different fixed dose sizes can, alternatively, be obtained with a set of two or more different fixed dose devices.

An alternative fixed dose device is disclosed in WO2018/007259 filed by Copernicus. The disclosure relates to an injection device for delivering a defined number of equal doses of a fluid substance. The disclosed injection device comprises a housing 1 with an arming mechanism and a dose delivery mechanism arranged along the longitudinal axis of the housing. The housing is coupled to an enclosure 3 for receiving a reservoir with the fluid substance. The arming mechanism comprises a setting sleeve 5, which is axially non-displaceable. The arming mechanism is rotatable about the axis of the housing in two opposite directions by a defined setting angle (a). The setting sleeve 5 is coupled with a torsion spring 10, which is strained by the rotation of the setting sleeve 5 during arming of the device. The dose delivery mechanism comprises a screw ring 6 and a piston rod 4 which is non-rotatable and axially displaceable within the setting sleeve 5. When the piston rod 4 cooperates with the screw ring 6, during arming of the device, the screw ring 6 and the piston rod 4 are immobilized. During delivery of each dose, the piston rod 4 is displaced along the housing 1 by a defined distance due to unwinding of the spring 10 and rotation of the screw ring 6. Displacement of the piston rod 4 causes the fluid substance to be discharged from the reservoir. As appears, to enable ejection of a dose the torsion spring must be strained. An alternative design utilizing the compression of a spring is described in WO 2017/098460 also filed by Copernicus. Another alternative device also utilizing the compression of a spring before each fixed dose is disclosed in WO94/26331 filed by Owen Mumford. However, arming the device between each dose is not always desirable, as it requires that the user can provide enough force to arm the device.

An alternative fixed dose device is disclosed in WO2013/034651 filed by Menarini. The disclosure relates to a device for the automatic injection of two doses of a medicament at two successive times. The disclosure describes an automatic injection device comprising a sliding sheath 30 which, when depressed with its front end 3 against the injection site, interacts with cam means 26, 27, 28 to activate the triggering of a plunger 8, controlling the delivery of a drug dose.

Plunger guide means 44 are provided on the inner surface of an outer housing 1 for controlling the triggering sequence and a dose knob 4 is used for arming or setting the device in the dose delivery condition. The device is adapted for automatic needle re-sheathing and resetting of a lock-out condition after each dose is delivered are provided. The number of the device components is reduced resulting in a simpler structure and cost reduction. Devices of same applicant and with a similar functioning are disclosed in WO2013/034647 and WO2011/111006. As appears all alternatives utilize a compression spring as the power means for driving the plunger.

Therefore, an unmet need exists for delivering alternative injection devices for delivering a predefined fixed dose, which addresses the needs for simple, safe, user-friendly and robust drug delivery devices.

Having regard to the above, it is an object of the present invention to provide a user-friendly, safe and robust drug delivery device for delivering a fixed dose of medicament. A further object is to provide such a drug delivery device comprising a drive mechanism with helical and axial guiding portions.

DISCLOSURE OF THE INVENTION

In the disclosure of the present invention, embodiments and aspects will be described which will address one or more of the above objects or which will address objects apparent from the below disclosure as well as from the description of exemplary embodiments.

In a first aspect of the present disclosure is provided a drug delivery device for delivering a fixed dose, wherein the drug delivery device comprises:
 a housing assembly,
 a drug reservoir with a piston
 a drive mechanism comprising a piston rod operationally arranged in the housing assembly and adapted for advancing the piston to expel a drug during dosing, and a drive tube operationally arranged with the piston rod (109, 209), wherein the drive tube (180, 280) is adapted to be axially movable relative to the housing assembly and rotationally blocked in a stationary state, and adapted to be axially movable and rotatable relative to the housing in a dosing state, wherein the drive mechanism is adapted to deliver the predefined fixed dose in response to activation;
 an activation mechanism for activating the drive mechanism, in response to moving the drive tube in an axial direction,
wherein the housing assembly comprises a guide structure for guiding the drive tube during activation and delivery of a dose, wherein the guide structure comprises an axial portion providing a sliding surface for guiding the drive tube during activation, and for providing a rotational stop defining an end of dose position, and a circumferential portion providing a sliding surface adapted for guiding the drive tube during dosing;
wherein the drive tube comprises a guide structure comprising an axial portion adapted for slidably engaging the corresponding axial portion of the housing assembly for activation, and a circumferential portion for slidably engaging the corresponding circumferential portion of the housing assembly during dosing during dosing,
whereby the drive tube (180, 280) can be guided along the axial portion (156, 256) without rotation and thereby changed from the stationary state to the dosing state during activation, whereby the drive tube (180, 280) can be moved axially and rotated by the drive mechanism in the dosing state, and whereby the drive tube (180, 280) can be guided along the circumferential portion (189, 289) until the end of dose position and thereby changed from the dosing state to the stationary state, in response to activation of the drive mechanism.

Hereby, is provided a drug delivery device, wherein the drive mechanism comprises helical and axial guide portions to provide a fixed dose upon activation.

In a further aspect, the guide structure of the housing assembly is a closed guide providing a work cycle for the drive tube, and wherein a starting position and an end of dose position of the drive tube is the same.

Hereby, the drive mechanism is adapted for providing a plurality of fixed doses using the same work cycle.

In a further aspect, the circumferential portion (157, 257) of the guide structure of the housing assembly is a helical portion (157, 257), or a stepped portion comprising at least one step, and wherein the corresponding circumferential portion (189, 289) of the guide portion of the drive tube (180, 280) is a helical portion (189, 289) corresponding to the helical portion (157, 257) of the housing assembly or a stepped portion comprising at least one step corresponding to stepped portion of the housing assembly.

In a further aspect, the housing assembly further comprises an inner tread, wherein the piston rod comprises an outer thread engaging the inner thread of the housing assembly.

Hereby is the piston rod operationally arranged in the housing via a thread connection.

In a further aspect, the drive tube is axially splined to the piston rod, whereby relative axial movement is allowed and relative rotation is prevented, and whereby the piston rod (109, 209) is advanced in response to rotation of the drive tube.

Hereby is the drive tube operationally arranged with the piston rod in a spline connection. A spline connection may comprise a key fitting in a key way.

In a further aspect, the drive mechanism further comprises a motor mechanism for imparting rotation of the drive tube for delivering a dose, in response to activation of the drive mechanism, wherein the drive tube is axially splined to the piston rod, whereby the drive tube is axially movable and rotationally locked relative to the piston rod, wherein drive mechanism further comprises a return mechanism for moving the drive tube in an axial direction, and thereby returning the drive tube after activation.

In a further aspect, the triggering mechanism comprises a movably arranged connector, wherein the connector comprises an activation tab, and wherein the activation tab is adapted for engaging a surface portion of the drive tube, in response to moving the connector in an axial direction, whereby the connector is operatively connected to the drive mechanism and adapted for triggering the drive mechanism, wherein the surface portion is oriented in a direction towards the activation tab.

Hereby, the activation tab can abut the surface portion of the drive tube during activation.

In a further aspect, the stationary state comprises: that the drive tube can be arranged in a home position, wherein the drive tube can be arranged in a first axial position, wherein the drive tube is allowed to move in one axial direction and blocked by the housing in the other axial direction, and arranged in a first angular position, wherein the drive tube is rotationally blocked by the housing in one direction and restricted in the other rotational direction by the drive mechanism, wherein the guide structure of the drive tube abuts the axial portion of the housing assembly and the helical portion of the guide structure of the housing assembly; wherein the dosing state comprises:

the drive tube can be arranged in a first dosing position, wherein the drive tube can be arranged in a second axial position and the first angular position, whereby the drive mechanism is activated and a second dosing position, wherein the drive tube can be arranged in an axial position between the first and the second axial positions, and an angular position different from the first angular position, wherein the helical portion of the guide structure is slidably arranged along the helical portion of the guide structure of the housing assembly, whereby a dose can be expelled.

In a further aspect, the connector is adapted to move the drive tube between the first axial and the second axial position, whereby the position of the drive tube (180, 280) is changed from the home position to the first dosing position, in response to moving the connector from a first axial to a second axial position, and wherein the drive mechanism is adapted to rotate the drive tube, and thereby change the position of the drive tube from the first dosing position, to the second dosing position and to the home position, in response to activation of the drive mechanism by setting the drive tube in the first dosing position.

In a further aspect, the first and second position of the connector is different from the first and second position of the drive tube.

In a further aspect, the axial distance between the first and second position of the connector is larger than or equal to the axial distance between the first and the second position of the drive tube.

In a further aspect, the motor mechanism comprises a torsional drive spring for rotating the drive tube by unwinding, wherein the drive spring is fixed between the housing assembly and the drive tube, wherein the drive spring further is compressible for moving the drive tube axially during rotation, whereby the drive spring provides the returning mechanism for returning the drive tube after activation.

In a further aspect, the drive spring comprises a compressible section.

In a further aspect, the activation tab of the connector comprises a transverse surface portion, and wherein the engageable surface portion of the drive tube is transverse, whereby initiation of dosing can be provided by a rotational movement induced by the torsional drive spring, in response to activation of the drive mechanism.

In a further aspect, the drug delivery device comprises a spring base rotationally arranged relative to the housing assembly, wherein a one-way ratchet mechanism is provided between the rotationally arranged spring base and the housing assembly, whereby the spring can be strained by rotating the spring base.

In a further or alternative aspect, the motor mechanism comprises a compression drive spring, wherein the activation tab comprises a helical surface portion, wherein the engageable surface portion of the drive tube for activating the drive tube comprises a helical surface portion, wherein the activation tab is adapted to impart an initial rotation of the drive tube in the dosing direction, in response to engaging the tab and moving the drive tube against the biasing force of the compression spring and between the distal and the proximal position, and wherein the helical portion of the housing assembly and the compression spring is adapted to provide further rotation of the drive tube, in response to the initial rotation, whereby a complete fixed dose can be delivered.

In a further aspect, the piston rod comprises an axially extending track, wherein the drive tube comprises inward protrusions adapted to slidably engage the axial track, whereby the drive tube is rotationally locked relative to the piston rod.

In a further embodiment the axial portion and the helical portion of the guide structure of the housing is an axial surface portion and a helical surface portion, respectively, and wherein the axial portion and the helical portion of the guide structure of the drive tube is an axial surface portion and a helical surface portion, respectively.

In a further aspect, the movement of the connector from the first axial to the second axial position is a pure axial movement.

In a further aspect, the first axial position is a distal position, and the second axial position is a proximal position.

In a further aspect, the drug delivery device is an injection device.

In a further aspect, the drug delivery device further comprises a shield for operating the connector, wherein the shield is adapted to cover a portion of a needle cannula in a distal position, and for exposing the needle cannula in a proximal position, wherein, for the shield being in the proximal position, the needle can be inserted into a subject, and wherein the shield is adapted to move the connector between the first and the second axial position, in response to moving the shield from the distal to the proximal position, wherein the first and the second position of the connector is a distal and a proximal position.

In a further or alternative aspect, the piston rod is axially splined to the housing assembly, whereby the piston rod is axially movable and rotationally locked relative to the housing assembly, wherein the drive tube further comprises an inner thread, whereby the piston rod is operationally arranged in the housing assembly, wherein the piston rod further comprises an outer thread for threadably engaging the inner thread of the drive tube, whereby the piston rod is operationally arranged with the housing assembly and the drive tube and wherein the piston rod is advanced during rotation of the drive tube, wherein the drive mechanism comprises a motor mechanism comprising a compressional drive spring for axially moving the drive tube and the piston, wherein the drug delivery device further comprises a connector with an inclined activation tab adapted to engage an inclined surface of the drive tube and impart an initial rotation of the drive tube in the dosing direction, in response to engagement between the activation tab and the drive tube against the biasing force of the compressional drive spring, wherein the stationary state comprises the drive tube can be arranged in a home position, wherein the drive tube can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the guide structure of the drive tube abuts the axial portion of the housing assembly and the helical portion of the guide structure of the housing assembly;

wherein the dosing state comprises:

the drive tube can be arranged in a first dosing position, wherein the drive tube can be arranged in a second axial position and the first angular position, wherein the activation tab engages the drive tube against the biasing force of the compressional drive spring, whereby the drive mechanism is activated, and a second dosing position, wherein the drive tube can be arranged in an axial position between the first and the second axial position, and an angular position different from the first angular position, wherein the helical portion (189, 289) of the guide structure is slidably arranged at any position along the helical portion (157, 257) of the guide structure of the housing assembly, whereby a dose can be expelled wherein the drive tube and the piston moves together, when the position of the drive tube is changed from the home position to the first dosing position, wherein the drive tube can rotate relative to the piston rod, in response to the angular position of the drive tube is changed from the first dosing position to the second dosing position, wherein the change of angular position relative to the housing is induced by the helical guide surface of the housing and the compressional drive spring, wherein the drive tube at the same time can move together with the piston rod, in response to the axial position of the drive tube is changed from the first dosing position to the home position, wherein the change of axial position relative to the housing is induced by the helical guide surface of the housing and the compressional drive spring, whereby a fixed dose has been delivered when the drive tube has returned to the home position, in response to activation of the drive mechanism.

BRIEF DESCRIPTION OF THE DRAWINGS

In the following embodiments of the invention will be described with reference to the drawings:

FIG. 1C illustrate structures both in black and white, and in grayscale in window W1, wherein the piston is separated from the chamber.

FIGS. 1D-1F illustrate details of the shield following portion, the cannula, the needle hub and the cartridge engaging structure of the cleaning assembly of the embodiment shown in FIG. 1A. In FIG. 1F window W2 illustrate the assembly in greyscale and W3 illustrate a section of the hub in greyscale to reveal guides on an inner surface.

FIGS. 2B, 2C and 2D illustrate structures both in black and white, and in grayscale in windows W4, W5 and W6, respectively, to increase the assessability of voids, inclined surfaces and separate parts. Window W6 is angled to show a slit in the hub.

FIGS. 4A and 4B illustrate details of the zero-point-adjustment nut of the embodiment shown in FIG. 1A.

FIG. 5 illustrates further details of the zero-point-adjustment mechanism provided on the elongate housing structure of the embodiment shown in FIG. 1A.

FIGS. 10A-10C show details of the elongate shield structure of the embodiment shown in FIG. 1A.

FIGS. 13A-13D show details of the drive mechanism of the embodiment shown in FIG. 1A.

FIGS. 14A-14B show cross sectional views of the entire injection device from two different angles. The illustrated device is the same as the embodiment shown in FIG. 1A.

FIG. 15A illustrate the operation for taking a first fixed dose, and 15B illustrates a subsequent dose.

FIG. 17 shows an exploded view of an injection device according to a second embodiment of the present disclosure.

FIG. 18 illustrates details a cross sectional view of the embodiment shown in FIG. 17.

FIG. 22 illustrates details of the connector of the embodiment shown in FIG. 17.

FIGS. 23A-23B illustrate details of the drive tube of the embodiment shown in FIG. 17.

FIG. 24 illustrates details of the elongate shield structure of the embodiment shown in FIG. 17.

FIG. 15A illustrate the operation for taking a first fixed dose, and 15B illustrates a subsequent dose.

FIGS. 25A-25G show the injection device of FIG. 17 in different states and intermediate arrangement, and thereby provide a detailed illustration of the operation of the device during a first dose.

FIGS. 26A-26B show the injection device of FIG. 17 in different states and intermediate arrangement during a subsequent dose.

Figure 1A:
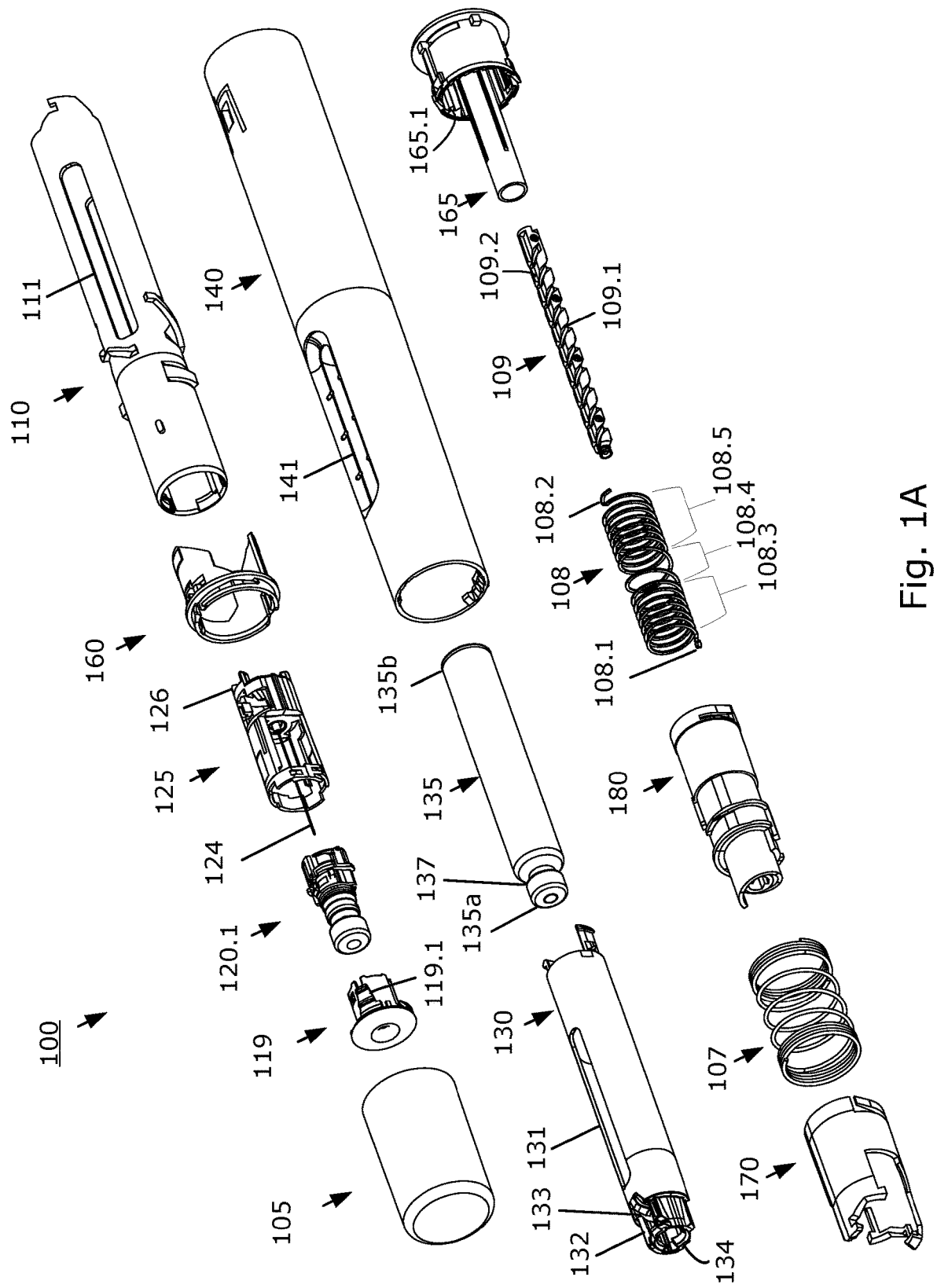
FIG. 1A shows an exploded view of an injection device according to a first embodiment of the present disclosure.

In the figures like structures are mainly identified by like reference numerals. Reference numbers followed by the letter "a" is used to denote the distal end of the structure, and numbers followed by "b" is used to denote the proximal end. Reference numbers comprising a first number followed by a "." and a second number is used to denote a functional or structural detail of a structure. In this way the first number indicates a primary (relatively large) structure and the second number indicates a secondary (relatively small) structure or a specific function. Reference numbers followed by the letters c, d and e indicate features with rotational symmetry.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member is used for a given component it can be used to define a unitary component or a portion of a component, having one or more functions.

In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term distal and proximal end is in analogy with the terminology from anatomy used to describe the end situated away from or nearest the point of attachment to the body. Therefore, the distal end of an injection device is defined in a context, where a user holds the device in a ready to inject position, whereby the end with the injection needle will be the distal end and the opposite end will be the proximal end. Furthermore, distal and proximal ends of individual components of the device is also defined in that context.

As used herein, a trailing edge and a front edge is used to describe the edges of a structure moving relative to another structure. The front edge is the edge in the moving direction and the trailing edge is the opposite. In this way, the front edge and the trailing edge defined according to the direction of the relative movement between structures.

As used herein, rotational symmetry, is a property of a structure when it appears the same or possess the same functionality after some rotation by a partial turn. A structure's degree of rotational symmetry is the number of distinct orientations in which it appears the same for each rotation. Rotational symmetry of order n, wherein n is 2 or more, is also called n-fold rotational symmetry, or discrete rotational symmetry of the $n^{th}$ order, with respect to a particular point (in 2D) or axis (in 3D), which means that rotation by an angle of 360°/n does not change the object. The property of the structure may both relate to the visible appearance and the functional capability of structural feature.

As used herein, the term clockwise direction is used to describe the direction that the hands of a clock rotate as viewed from in front. Therefore, the clockwise rotation of the injection device is the clockwise rotation observed, when viewing the device from in front of the distal end. Counterclockwise or anticlockwise rotation is defined as the opposite direction.

As used herein, a proximal face is a face of the device as viewed from the proximal end and in the distal direction, wherein a distal face is a face of the device as viewed from the distal end and in the proximal direction.

As used herein, a positive axial or longitudinal direction is defined from the proximal end towards the distal end. A positive axial direction and a distal direction are used interchangeably with the same meaning. Similar, the definitions a negative axial direction and proximal direction are used interchangeably with the same meaning. A central axis of the device is defined through the centre of the injection device in the positive axial direction, which is also referred to as a longitudinal axis, with the same meaning.

As used herein, a positive radial direction is defined along a radial axis originating at the central axis and with a direction perpendicular to the central axis.

A positive circumferential or positive angular direction is defined for a point positioned at a radial distance from the central axis, wherein the circumferential direction is counterclockwise and perpendicular to the axial and radial direction. A direction can as used in the present disclosure be both positive and negative. For example the term axial direction covers the positive axial direction from the proximal end towards the distal end and the negative axial direction, which is in the opposite direction.

Both the radial and the circumferential direction are herein referred to as transverse directions, as they are transverse normal to the axial direction. The transverse plane is herein defined as a plane spanned by two vectors in the radial and circumferential direction, for a given coordinate along the axis, and with the central axis as the normal vector.

As used herein, axial movement of a structure is used to describe a movement, wherein the displacement vector of the structure has a component in the axial direction. A translational movement is used to describe a uniform motion in the axial direction only. A pure, strict or uniform axial movement is the same as a translational movement and the terms are used interchangeably.

Radial movement of a structure is used to describe a movement, wherein the displacement vector of the structure has a component in the radial direction. A pure or strict radial movement is used to describe a uniform motion in the radial direction only. Thus a pure, strict and uniform radial movement is the same and the terms are used interchangeably.

Circumferential, angular or rotational movement of a structure is used to describe a movement, wherein the displacement vector of the structure has a component in the circumferential direction. A pure or strict circumferential movement is used to describe a uniform motion in the circumferential direction only. Thus a pure, strict and uniform circumferential movement is the same as pure, strict and uniform angular or rotational movement, and these terms are used interchangeably. The definition of rotational movement for a structure also encompasses the special case, wherein the structure comprises a central axis defining the axis of rotation. In this special case, all the positions of the structure, which are off the central axis, are subject to a circular circumferential movement, whereas the displacement vector of the positions on the central axis is zero.

Therefore, a structure rotating about its own central axis and moving in an axial direction is said to perform a rotational movement.

A helical movement of a structure is used to describe a combined axial and angular or rotational movement, wherein the displacement vector of the structure comprises a circumferential and an axial component. The definition of helical movement for a structure also encompasses the special case, wherein the structure comprises a central axis defining an axis of rotation. In this special case, all the positions of the structure, which are off the central axis, are subject to a helical movement, whereas the displacement vector of the positions on the central axis only comprises an axial component. Therefore, a structure rotating about its own central axis and moving in an axial direction is said to perform a helical movement.

In this context pure, strict and uniform movements are abstract mathematical definitions, and these terms are used to describe an ideal or abstract movement of the devices. Therefore, a structure in a real device should not be expected to exhibit this ideal behaviour, rather such a structure should be expected to move in a pattern approximating such an ideal movement.

As used herein a right-handed thread or helical portion is a thread or helix portion whose helix moves in the positive axial direction, when the screw is turned clockwise. A screw with a right handed-thread is by convention the default thread, and is screwed in the positive axial direction by counterclockwise rotation usually performed by the right hand. Similar, a screw with a left-handed thread is screwed in the positive axial direction by clockwise rotation, and can thus be performed with the left hand and mirror the movement of the right hand operating a right handed thread.

The embodiments of the present disclosure are described in detail in relation to an injection device which is adapted for providing a plurality of fixed doses. However, the injection device may also be adapted to provide only one predefined fixed dose, wherein the volume of drug is defined by the drive mechanism including the number of rotations per dose and the pitch thread of the piston rod.

The embodiments of the present disclosure, wherein the injection device is adapted for providing a plurality of predefined fixed doses, are described in detail in relation to an injection device comprising a reusable integrated needle cannula with a cleaning chamber. However, in an alternative embodiment a needle magazine as described in EP20157959.6 titled an injection device with integrated needles could be integrated instead one single re-usable needle and filed by Novo Nordisk.

First Embodiment

Figure 15A:
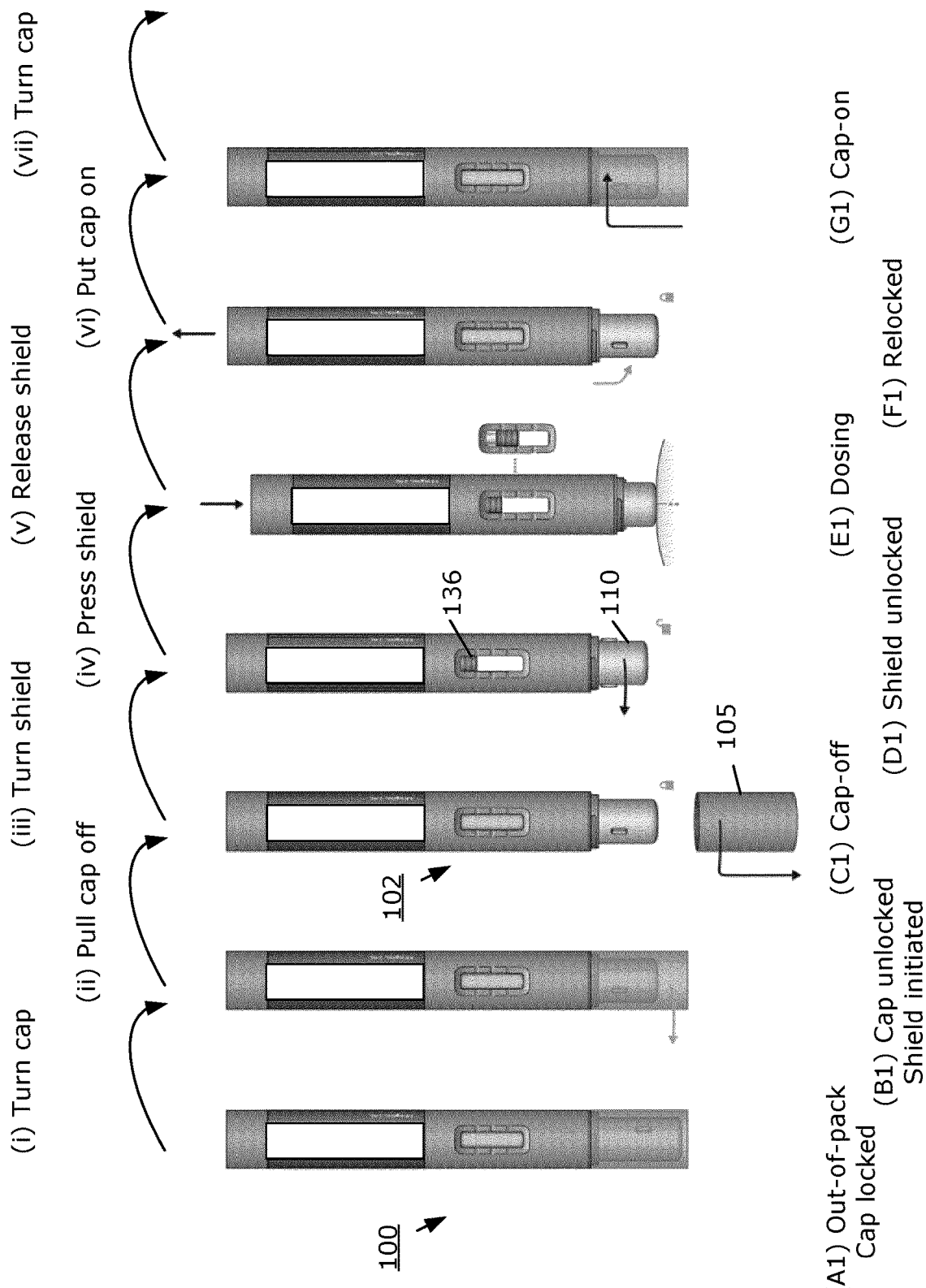
FIGS. 15A-15B illustrate user operations and states during the operation of the injection device of FIG. 1A.
Figure 15B:
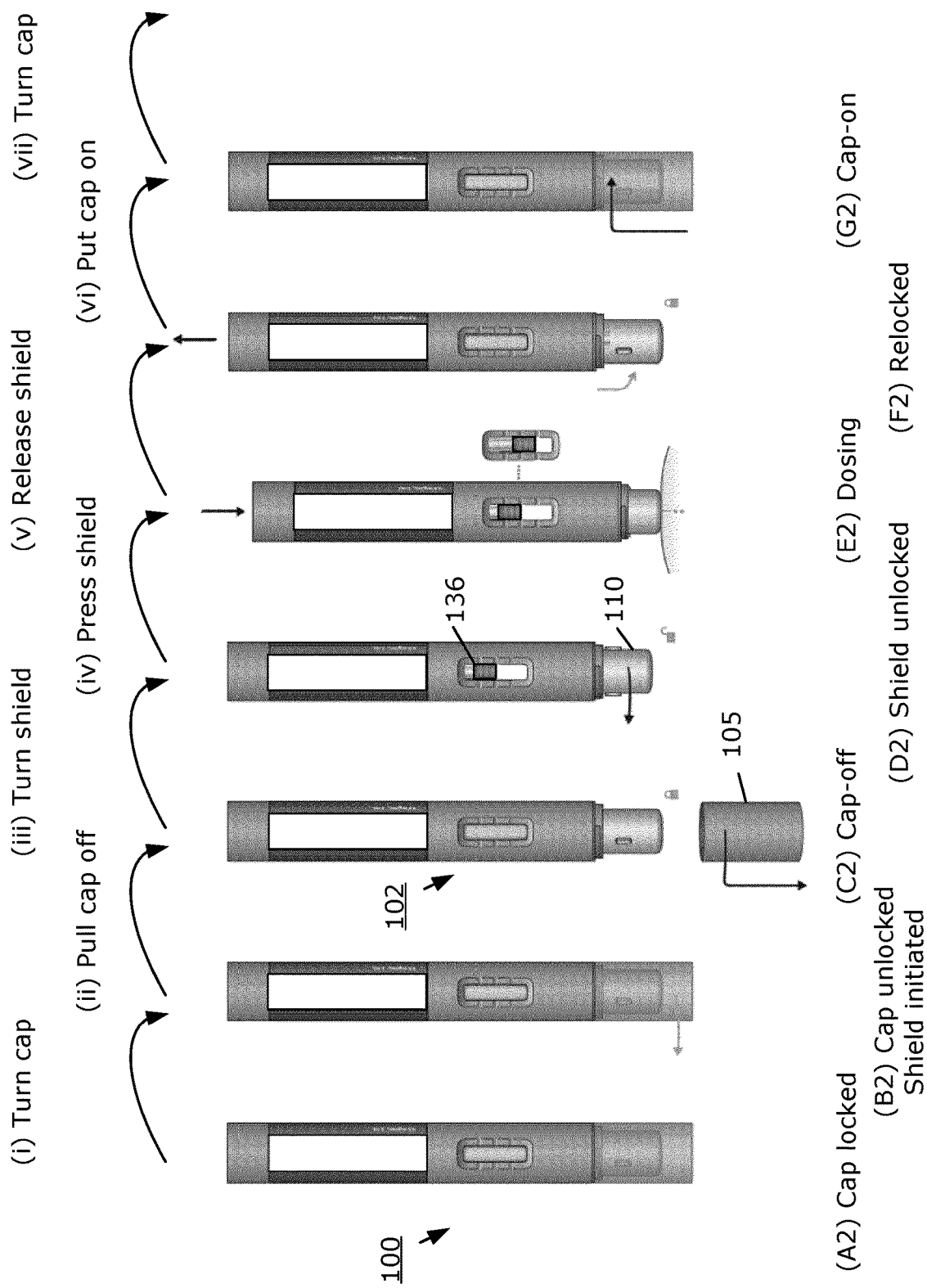

FIG. 1-16 illustrate a first embodiment of an injection device for delivering a plurality of fixed dosses according to the present disclosure. FIG. 1A shows an exploded view of such an injection device. FIG. 1B-14 show further details of the individual structures and mechanism. FIGS. 15A and 15B show in perspective view, a sequence of states during use of the injection device 100, and thereby illustrates the user operations from receiving the device, initiating the device and delivering the plurality of fixed doses. FIG. 16 illustrate in details the interrelation of the mechanical structures during operation. As used herein, a state defines a certain arrangement or configuration of the device, and the states and the operations provide a frame for explaining the working principles of the device.

FIG. 1A shows a cap 105, a shield tip 119, a shield following portion 120.1 of a cleaning module 120 (see FIG. 2B), a needle hub 125 with a needle cannula 124, a housing insert portion 160, a tubular elongate needle shield structure 110, a cartridge holder 130, a cartridge 135, a tubular elongate housing structure 140, a connector 170, a shield return spring 107, a drive tube 180, a dose drive spring 108, a piston rod 109, and a spring base 165.

Housing Assembly

The injection device comprises a housing assembly, providing a rigid frame with guides and connectors for guiding and connecting the other components of the device. The housing assembly comprises the housing insert portion 160, the tubular elongate housing structure 140, the cartridge holder 130 and the spring base 165. After final assembly these structures are fixedly connected, and the housing assembly can provide a frame of reference for describing the relative movement and position of the other structures. The elongate housing structure 140 comprises an internal thread for engaging an outer thread of the piston rod. The internal thread may be provided in the form of an integral nut member, which is fixed to the housing structure 140 both rotationally and axially. In one example, the nut member is an integral part of the housing structure 140. Alternatively, the nut member can be a separate part which is fixed to the housing during assembly of the injection device e.g. by gluing or welding. The nut member is on an inner surface provided with an inner thread which engages with the outer thread of the piston rod 109 such that the piston rod is moved helically when it is rotated relatively to the housing structure. Alternatively, the inner thread is provided directly in the housing. The housing insert portion 160 comprises a cap snap at the end of a track for a bayonet coupling with the cap. The housing insert portion 160 further comprises a proximal edge for guiding the shield. For further description, the housing assembly may in short be referred to as the housing, and the needle shield assembly as the needle shield.

The injection device 100 comprises a drive mechanism and a triggering or activation mechanism. The drive mechanism comprises the piston rod 109, the drive spring 108, and the drive tube 180, and for expelling a dose the structures are operationally arranged in the housing. The triggering mechanism comprises the elongate shield structure 110 and the connector 170, and for triggering the dose expelling mechanism the structures are operationally arranged in the housing.

Needle Shield Assembly

The injection device further comprises a needle shield assembly comprising the shield tip 119 and the elongate shield structure 110. The elongate shield structure 110 comprises a window 111 for inspection of the drug, the elongate shield can be arranged in a first position of overlapping with the cartridge holder window 131, and in a second position with no overlap, wherein a solid portion of the elongate shield structure covers the window 131 in the second position.

Cartridge Holder

Figure 1B:
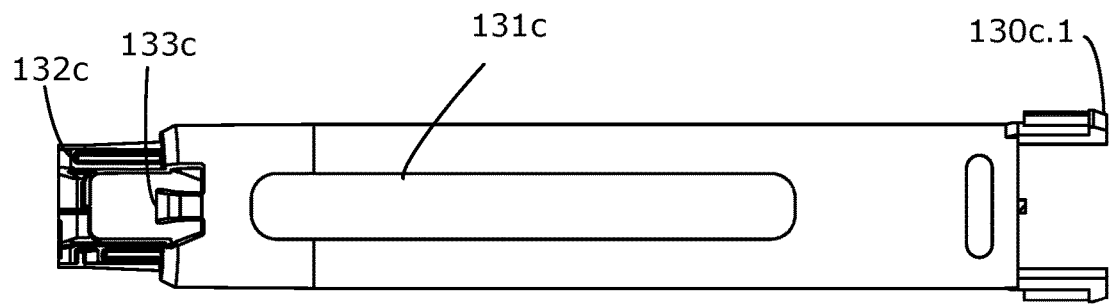
FIG. 1B illustrates details of the cartridge holder of the embodiment shown in FIG. 1A.

The cartridge holder 130 is adapted for receiving the cartridge 135. The cartridge holder comprises a window 131 for inspecting the drug in the cartridge 135. FIG. 1B show in profile the cartridge holder 130 comprising an axial rib 132 for axially guiding the needle hub, a flexible arm for snapping to a neck portion 137 (FIG. 1A) of the cartridge and a proximally extending tab 130.1 for aligning and positioning the cartridge when inserted into the housing during assembly. On an inner surface at the distal end of the cartridge holder is provided a circumferentially extending flange 134 (FIG. 1A), providing a small axial clearance to the distal end surface of the cartridge, after assembly and in an initial out-of-pack state.

Cartridge

As further shown in FIG. 1A, the elongate cartridge 135 comprises a distal end 135a sealed by a pierceable septum and an open proximal end 135 closed by a piston. The piston is not shown on FIG. 1. The cartridge comprises a reservoir containing the plurality of fixed doses of a medicament. At the distal end 135a is provided a septum capped on by a cap. The cap and a main portion of the reservoir is separated by the neck portion 137.

Needle Assembly

The injection device further comprises a needle assembly comprising a needle hub 125 and a reusable needle cannula 124. The cannula comprises a proximal end for piercing the pierceable septum and for establishing fluid communication with the reservoir, and a distal end for insertion into the skin of a subject or user of the device.

Piston Washer

A piston washer, although not shown on FIG. 1, can be connected to the piston rod to provide a pressure foot for contacting the piston. Alternatively, a dose measuring module for measuring the relative rotation between the piston rod and the piston can be provided between the piston rod and the piston. Such a measuring module also provides a suitable pressure foot. Such a dose measuring module is described in WO 20141128155, titled "Dose capturing cartridge module for drug delivery device. Alternatively, the piston rod directly contacts the piston".

Cap

The cap 105 is adapted for releasable mounting to the housing insert portion 160. The cap comprises an inner surface with a protrusion 105.2 (FIG. 16F) adapted to be guided by the axial and the circumferential cap mount track 161, which will be described in detail later in the application. The protrusion is further adapted to cooperate with a snap lock 161.1 and thereby releasably lock the cap 105 to the inner housing portion 160. The cap is adapted to be mounted and demounted by a sequential axial and rotational movement, and thereby provides a bayonet coupling together with the injection device. The inner surface of the cap 105 further comprises an axially extending rib 105.1 (FIG. 16A) protruding from the inner surface and adapting the cap for transferring a torque to the shield structure 110 through an axially extending rib 116 on the outer surface of the shield, as will be explained later with reference to FIG. 16A.

Spring Base

The spring base 165 is fixedly mounted to the housing structure 140 at the proximal end and is adapted to receive and support a compressible torsional drive spring 108.

Drive Spring

The drive spring 108 is pre-strained or winded up and positioned between the spring base and the drive tube 180. The drive spring is further adapted to induce a torque on the drive tube, whereby the medicament can be expelled. The drive spring comprises torsional sections 108.3, 108.4, wherein the spacing between the coils is relatively small and a compressible section 108.4 adapted to transfer an axial force to the drive tube after compression and during expelling of the medicament. The ability to drive the drive tube in an axial direction enables an end of dose mechanism, and to enable a resetting of the drive tube.

Return Spring

The connector return spring 107 is positioned between the spring base 165 and the connector 170 and is adapted to urge the connector in the distal direction.

Cleaning Assembly

Cleaning the needle between injections allows the same integrated needle to be used a plurality of times in a clean condition. Therefore, in an alternative embodiment of the present disclosure, the injection device comprises a cleaning assembly 120, as illustrated in FIG. 2B. The movable shield structure 110 is fixedly connected to the cleaning assembly 120 through a shield following portion 120.1, and the principles of the cleaning module is disclosed in further details in WO2019/101670. The cleaning assembly 120 comprises a cleaning agent, which keeps the distal end of the needle cannula 124 clean between injections. The shield following portion 120.1 of the cleaning module is fixedly connected to the shield tip 119, which again is fixedly connected to the movably arranged elongate needle shield structure 110. The shield tip 119 can be click fitted to the needle shield structure 110 via resilient arms 119.1 engaging the elongate shield structure 110, such that the cleaning chamber assembly 120 follows axial and rotational movements of the movably arranged shield structure 110. The shield structure 110 which is connected to the cleaning assembly 120 is movably arranged relative to the needle cannula 124, which is fixed to the housing.

The cleaning assembly 120 preferably contains a chamber with a liquid cleaning agent which in one example can be the same preservative as contained in the liquid drug in the cartridge 135. In a preferred example, the cleaning agent is the identical same preservative containing pharmaceutical liquid drug as contained in the cartridge 135, which is filled into the chamber of the cleaning module during the initiation of the injection device. In an alternative embodiment the cleaning agent is embedded in a porous plug. In a further alternative the cleaning agent is embedded in a matrix of a solid plug.

The shield can be arranged in different positions. An initial position defined by an initial angular position and a corresponding initial axial position. A locked position defined by a locked angular position and a corresponding locked axial position. An unlocked distal position defined by an unlocked angular position and a corresponding distal unlocked axial position. The movable shield can be changed by a combined rotational and proximal movement from the initial position to the locked position, wherein the shield is axially locked. In both positions the needle tip is covered by the shield and contained in the cleaning chamber assembly. During use the shield can be further rotated and moved further in the proximal direction to the unlocked distal position, whereby the tip is uncovered. By moving the shield further in the proximal direction the shield uncovers a larger portion of the needle and an injection can be made. After injection the shield is moved back to the locked position, whereby the needle tip is cleaned.

If it for some reason should be desired to reuse the needle without cleaning the needle, the cleaning module can be left out.

Figure 1C:
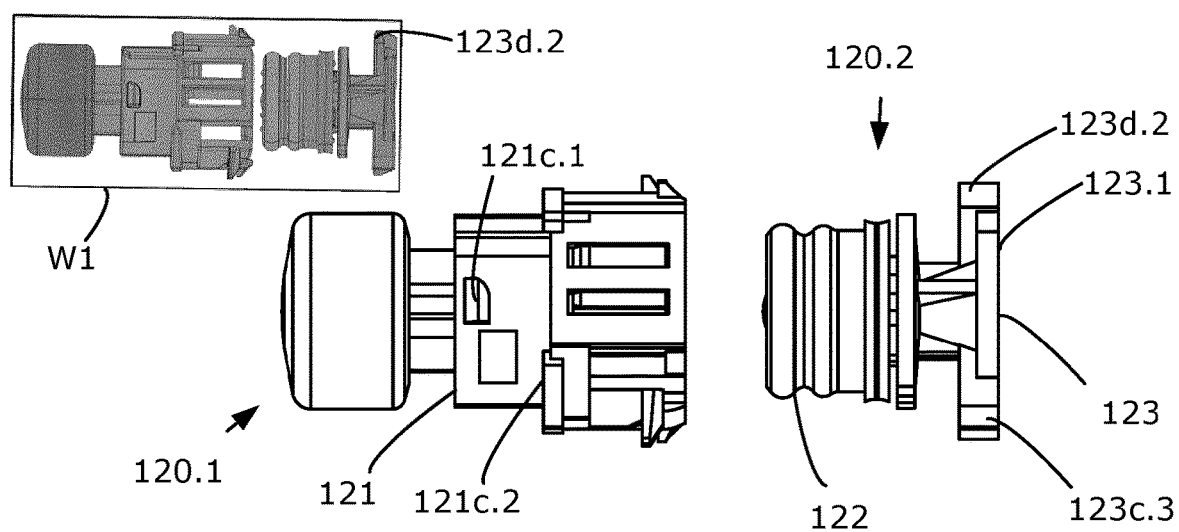
FIG. 1C illustrates details of the shield following portion and the movable portion of the cleaning assembly of the embodiment shown in FIG. 1A.

Returning to the illustrated embodiment 100. FIG. 1B illustrates a perspective view of the cartridge holder 130 with the proximally extending tab 130.1 for aligning and positioning the cartridge holder 130 relative to the housing 140, when inserted into the housing during assembly. FIG. 1C illustrates an exploded view of the cleaning module 120 comprising the shield following portion 120.1 and a movable portion 120.2 comprising a piston 122 and a piston rod 123 with radially extending arms 123.1 for cooperating with the needle hub 125 and the shield following portion 120.1. The radially extending arms 123.1 comprises a chamber housing engaging surface 123.2 for engaging the cleaning chamber 120 and a hub engaging portion 123.3 for engaging the hub 125. The needle following portion 120.1 comprises a cleaning chamber housing 121 comprising a distal tubular portion, a middle tubular portion and a proximal tubular portion. The portions are integrally connected. On the distal end of the distal tubular portion is provided a cap, capping a distal septum onto the cleaning chamber housing. On the outer surface of the middle tubular portion is provided a shield tab 121.1 for snapping to the shield tip 119, and a hub pushing tab 121.2. Window W1 of FIG. 1C illustrates the same components in grey scale to better illustrate inclined surfaces and void portions. As shown on FIG. 2B, at a proximal end of the cleaning chamber housing 121 is provided a sloped proximal surface guide 121.3 for guiding the piston rod 123 and the piston 122 in the proximal direction, in response to rotation. Window W3 in figure supports the understanding of the mechanism for guiding or pushing the piston rod in the proximal direction. Rotating piston rod 123 releases static friction, and by rotating it further and pushing it into the inclined surface 121.3 of the cleaning chamber will provide a first well defined axial movement. On FIG. 2D is shown a cleaning agent reservoir 121.4 for enclosing the distal end of the needle cannula in a sterile condition before use, and a clean condition during use.

FIG. 1D shows in perspective view the relative positioning of the needle cannula 124, the movable portion of the cleaning chamber 120.2 comprising the piston 122 and the piston rod 122, and a cartridge engaging structure comprising a rigid portion 126 and a soft inner plug (not shown on figure). The soft inner plug can be made of rubber, and adapted for enclosing the proximal end of the needle cannula in a sterile initial condition before use. The rigid portion 126 provides support for the soft inner plug and is adapted for moving the cartridge in the proximal direction, when the needle has established fluid connection with the drug in the reservoir, and in response to moving the hub 125 in a proximal direction. The soft plug can be penetrated by the proximal sharp end of the needle cannula. The rigid portion 126 comprises a radially extending hub engaging tab 126.1 and a radially extending cartridge engaging tab 126.2. The rigid portion further comprises a distally extending blocking portion 126.3 for blocking further axial movement of the hub, when the hub is in the proximal position. As seen on FIG. 2D, the blocking portion 126.3 is adapted to engage a small indent or circumferential slit 125.7 in the hub, after a small relative rotation. The rigid portion 126 comprises a proximal surface at the proximal end 126b abutting a distal surface of the cartridge, after assembly. Therefore, a proximal movement of the rigid portion 126 of the cartridge engaging structure provides a proximal movement of the cartridge.

FIG. 1E illustrates a perspective view of the needle hub 125. The hub 125 comprises a central circular disk portion 125.9 and a proximally extending skirt portion 125.11 extending from the disk portion. The skirt portion 125.11 is adapted for enclosing a distal end of the cartridge 135 and the cartridge engaging structure comprising the rigid portion 126. The needle hub 125 further comprises axially extending fingers 125.1 extending proximally from the skirt portion 125.11 and adapted for cooperating with the axially extending rib 132 of the cartridge holder to allow relative axial movement between the hub and the cartridge holder, and to prevent relative rotational movement. From a distal surface of the central disk portion 125.9 extends two axial tube portions (angular section, they are curved like a tube, but do not extend 360 degrees in the circumferential direction) or flanges 125.12 connecting a tubular portion 125.13 with the central portion 125.9. The tubular portions are adapted to surround the cleaning assembly 120. As best seen on FIG. 2D, a glue tower 125.10 for fixating the needle cannula is provided centrally on the central disk portion 125.9. The hub 125 further comprises a track provided in the skirt portion 125.11 and adapted for guiding a rotational movement of the cartridge engaging structure. The track comprises a proximal axial portion 125.2 providing an initial seat for the hub engaging tab 126.1 of the cartridge engaging structure, and a helical portion 125.3 for rotating the tab 126.1 and thereby the rigid portion 126 of the cartridge engaging structure, in response to a guided proximal movement of the needle hub 125. The track further comprises a distal axial portion 125.4 adapted to allow or guide relative axial movement or the tab 126.1 and thereby the rigid portion 126 of the cartridge engaging structure, at the end of rotation. On an inner surface of the axially extending flanges 125.12 is provided, a rib 128 protruding in the negative radial direction, i.e., towards the center of the hub 125. The rib 128 comprises an axially extending surface 128.1 flush with an edge of the flanges 125.12. The axially extending surface 128.1 provides a rotational stop for engaging the piston rod 123. At the distal end of the rib 128, is further provided a circumferentially extending surface 128.2 (see also FIG. 1F window W3 and 2D). The circumferentially extending surface 128.2 provides an axial stop for engaging the push tab 121.2 of the chamber housing.

FIG. 1F illustrates the assembly of the module shown in FIG. 1D with the hub 125 shown in FIG. 1E in the out-of-pack state, which is the initial state and before fluid connection is established between the needle cannula and the reservoir of the cartridge 135. It is noted that an axial clearance is provided between the blocking portion 126.3 and a proximal surface of the central portion 125.9, this clearance allows a relative axial movement between the hub 125 and the rigid portion 126 of the cartridge engaging structure, which is in abutment with the cartridge 135. Therefore, the clearance allows the needle cannula to be inserted into the cartridge, in response to the relative axial movement. Window W2 illustrates the entire assembly shown in black and white in grayscale. Window W3 illustrates the inner surface of the needle hub 125 and the guide 128 with the surfaces 128.1 and 128.2.

Figure 2A:
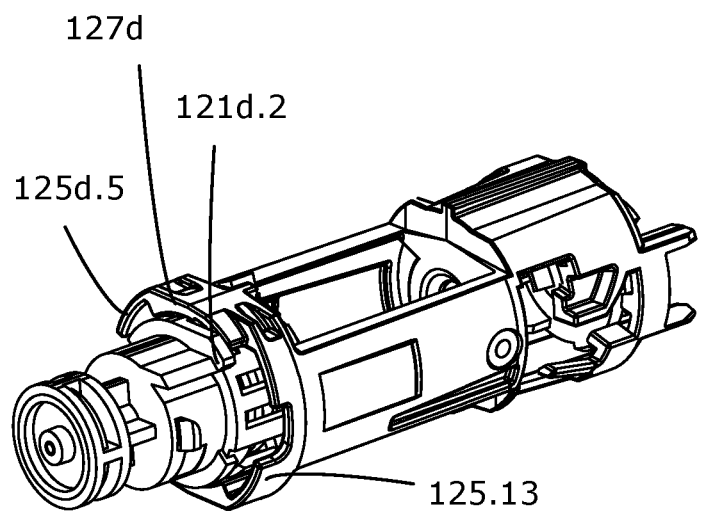
FIGS. 2A-2D illustrate further details of the cleaning assembly of the embodiment shown in FIG. 1A.
Figure 2B:
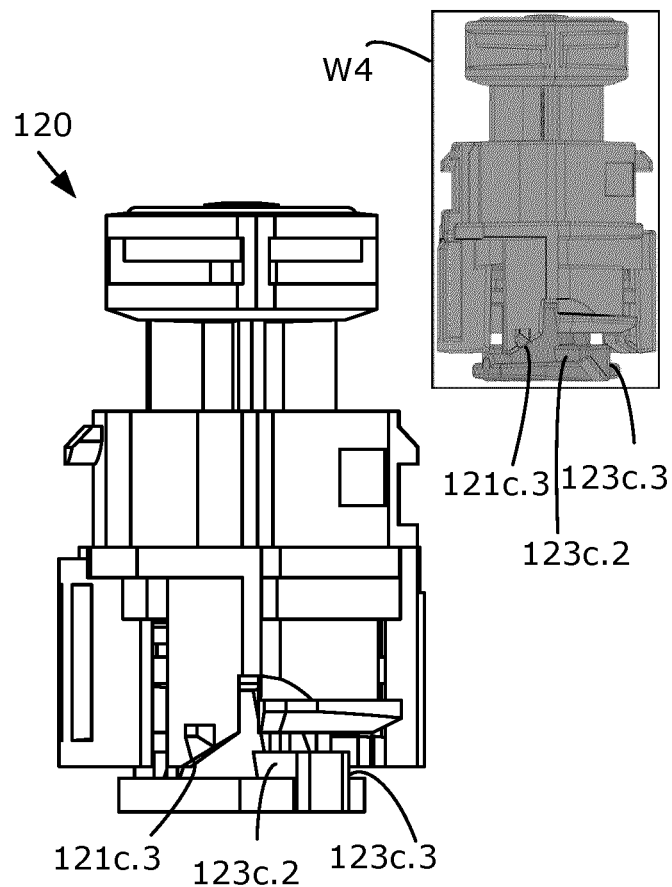
Figure 2C:
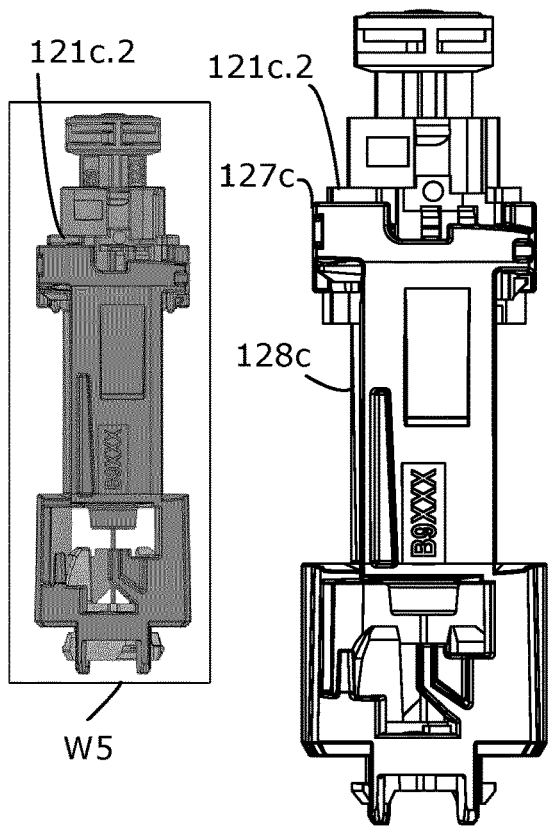
Figure 2D:
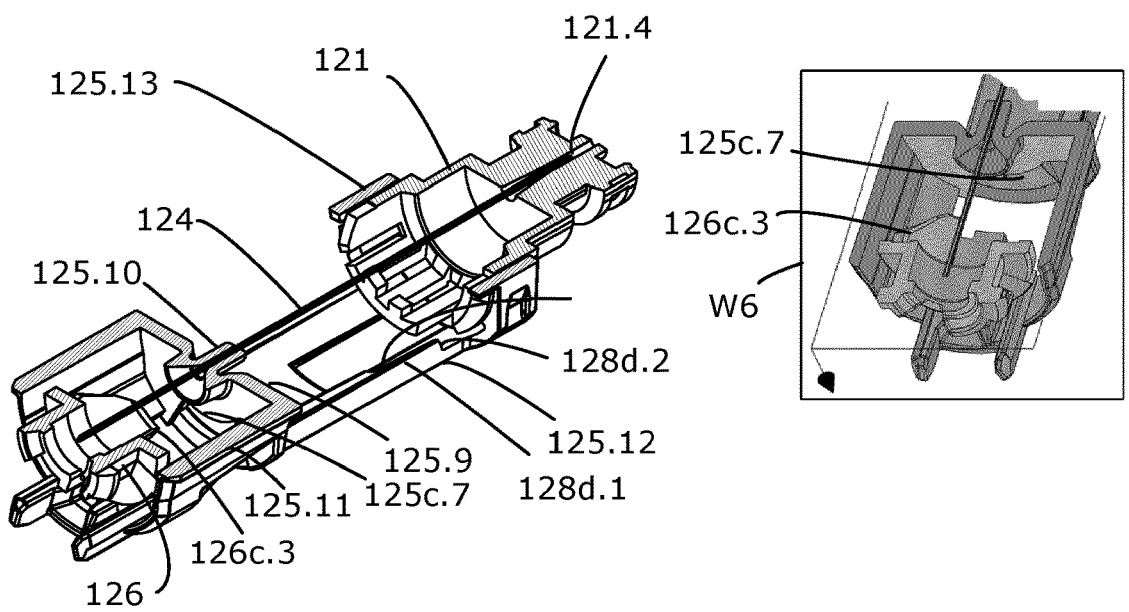

FIG. 2A illustrates a perspective view of the cleaning chamber housing 121 positioned in the needle hub 125 in the out-of-pack state. The tubular portion 125.13 surrounds the proximal portion of the cleaning chamber housing, and the radially extending hub pushing tab 121.2 rests on a distal support surface 127 of the hub, in a first angular position. As explained in detail later in the application, upon initialization the needle shield is adapted to be guided in a proximal helical movement. As the cleaning chamber housing is fixed to the needle shield, the pushing tab 121.2 performs a proximal helical movement relative to the rotationally fixed needle hub, in response to initialization. The needle hub is axially movable between a distal and a proximal position. As the needle hub is axially movably positioned on the cartridge holder 130, the pushing tab 121.2 of the chamber housing forces the needle hub from the distal to the proximal position, in response to the needle shield moving from the initial to the locked position. Furthermore, during the axial movement of the shield, the pushing tab 121.2 has also rotated from the initial to the locked angular position together with the shield. In the locked angular position, the push tab 121.2 is angularly aligned with a cut-out 125.5 in the tubular portion 125.13 of the needle hub, and it is aligned with the axial stop surface 128.2. An axial clearance is provided between the push tab 125.2 and the axial stop surface 128.2. Between the initial and the locked angular position of the shield, the hub has been moved a proximal distance to connect the proximal end of the needle cannula 124 with the reservoir of the cartridge 135. The proximal movement of the hub has further provided a rotation of the cartridge engaging structure, whereby the tabs 126.2, having cam surfaces, has been rotated and forced into the axial clearance between the distal surface of the distal end of the cartridge and the proximal surface of the circumferentially extending flange 134 (see FIG. 1A). Hereby, the axial clearance between the cartridge and the circumferential flange 134, has been made larger and the cartridge has been pushed in the proximal direction relative to the cartridge, and the neck engaging arms 133 has been deflected. In the locked position of the shield, corresponding to the proximal position of the hub 125, contact has been established between the blocking portion 126.3 of the cartridge engaging structure and the central hub portion 125.9. In this position, the cleaning chamber housing can move proximally until it abuts the stop surface 128.2. For the shield and the shield following portion 120.1 being in the locked position, the shield following portion is adapted to be moved in a further proximal helical movement together with the shield to the distal unlocked position. For the shield and the shield following portion 120.1 being in the distal unlocked position, the shield and the shield following portion can further moved in a strict proximal direction to deliver a dose through the needle.

FIG. 2B illustrates a perspective view of the cleaning chamber piston rod 123 arranged in the cleaning chamber housing 121. As illustrated, the sloped surface 121.3, at a proximal surface of the chamber housing 121, is axially aligned with the axially extending surface 123.2 of the piston rod. In this initial position, the surface 123.3 of the piston rod is arranged in abutment with the rotational stop 128.1 of the hub 125, and can therefore not be moved in the counterclockwise direction relative to the hub. A circumferential clearance is initially provided between the sloped surface 121.3 and the chamber housing engaging surface 123.2, and in response to the proximal helical movement of the chamber housing, the sloped surface 121.3 and the engaging surface 123.2 will approach and engage each other to make contact. Hereby, any static or sticking friction between the plunger 122 and the chamber housing 123 is overcome by the relative rotation. In response to further rotation until the locked position of the shield, the sloped surface will induce a proximally directed force on the piston rod 123, whereby the piston rod 123 and the plunger will be pulled out of the cleaning chamber housing.

As the plunger 136 in the cartridge 130 is positioned in abutment with the piston rod 109, a proximal movement of the cartridge relative to the cartridge holder (which is a part of the housing assembly) will induce an overpressure in the cartridge. If the reservoir is in fluid contact with the needle cannular, the liquid will flow into the cleaning chamber. The additional feature of pulling the plunger 122 out of the cleaning chamber housing 121, is provided to overcome stick friction between plunger and chamber housing 121, but the pulling will also add to the flow between reservoir and chamber housing 121, when fluid connection has been established.

Housing Structure

Figure 3A:
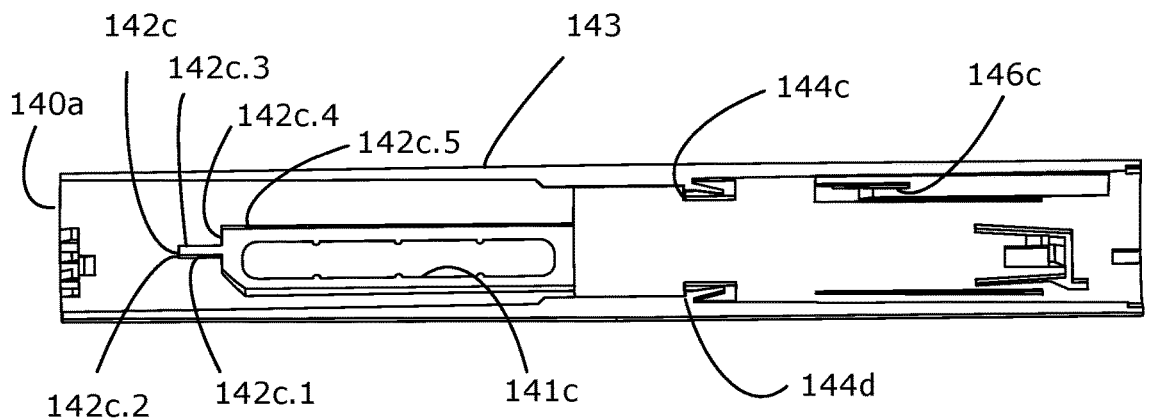
FIGS. 3A-3F illustrate details of the guiding structures of the elongate housing structure of the embodiment shown in FIG. 1A.
Figure 3B:
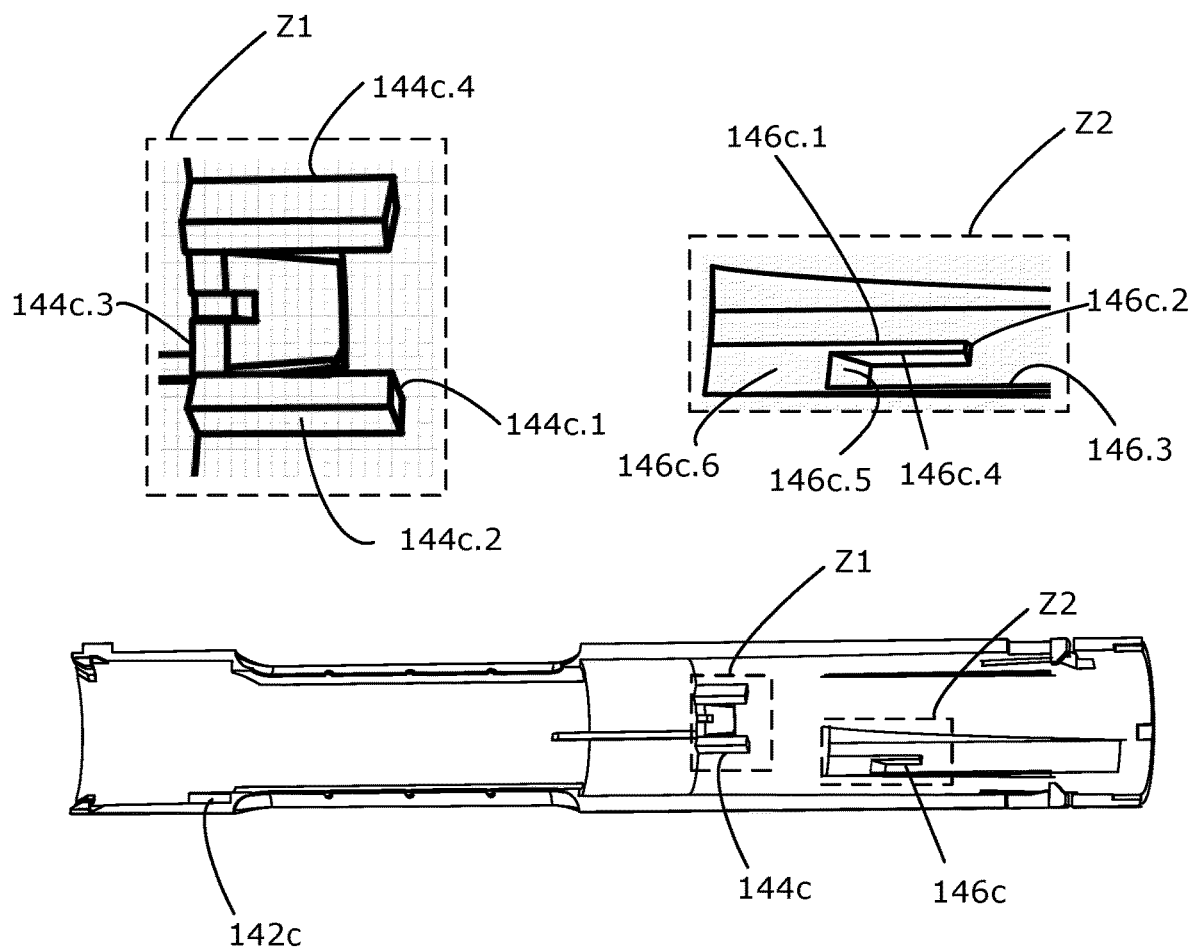

FIGS. 3A and 3B illustrate a perspective view of features arranged at the inner surface of the tubular housing structure 140 in an axial cut of the housing. In FIG. 3B the axial cut is provided in a plane containing a central axial line of the windows 141, and in FIG. 3A the injection has been rotated 90 degrees about the central axis, whereby one of the windows 141c is visible behind the cutting plane. As seen in FIG. 3C to 3F the tubular housing structure 140 comprises an outer tubular portion 143 and an inner tubular portion 154. In the illustrated example, the inner tubular portion 154 is integrally connected to the outer tubular portion. The outer tubular portion comprises an outer surface with an outer diameter and an inner surface with an inner diameter. Similarly, the inner tubular portion comprises an outer surface with an outer diameter and an inner surface with an inner diameter In FIGS. 3A and 3B, the inner tubular portion 154 has been removed to get a clear view of the structures between the outer tubular portion 143 and the inner tubular portion 154. The figures illustrate a distal guide structure of the housing 142 protruding from the inner surface. The distal guide structure 142 is adapted for guiding the shield structure 110. The figures further illustrate a middle guide structure of the housing 144c and a proximal guide structure of the housing 146c. The middle guide structure 144d, which is positioned 180 degrees from 144c in rotational symmetry is also shown on FIG. 3D. The middle guide structure 144 also protrudes from the inner surface and provides the integral connection between the outer tubular portion 143 and the inner tubular portion 154. The middle guide structure is further adapted for guiding the connector 170 and the shield structure 110. The proximal guide structure 146c forms a recess into the surface, and is adapted for guiding the connector 170. The distal, the middle and the proximal guides 142c, 144c and 146c all have a corresponding guide positioned in rotational symmetry, although not all of them are shown or indicated. However, when e.g. referring to a distal guide 142 it can be any of the distal guides positioned in rotational symmetry, and in the illustrated example 142 can refer to either or both of distal guides 142c and 142d.

The distal guide 142 comprises a first axial portion 142.1, a first transverse portion 142.2, a second axial portion 142.3, a second transverse portion 142.4 and a third axial portion 142.5 providing a rotational stop. The middle guide comprises a proximal transverse portion 144.1, a first axial portion 144.2, a distal transverse portion 144.3 and a second axial portion 144.4. The proximal guide comprises a first axial portion 146.1, a first transverse portion 146.2, a second axial portion 146.3, a third axial portion 146.4, a ramp portion 146.5, a flush portion 146.6. Collectively, the guide surfaces provide a closed track allowing a cyclic guiding of the connector. The surface of the transverse portions extends in the radial and circumferential direction, the surface of the axial portion extends in the axial and radial direction, the surface of the ramp portion 146.4 extends from the bottom of the recess towards the surface of the flush portion 446.5. The flush portion extends in the axial and circumferential direction and is flush with the inner surface.

Figure 3C:
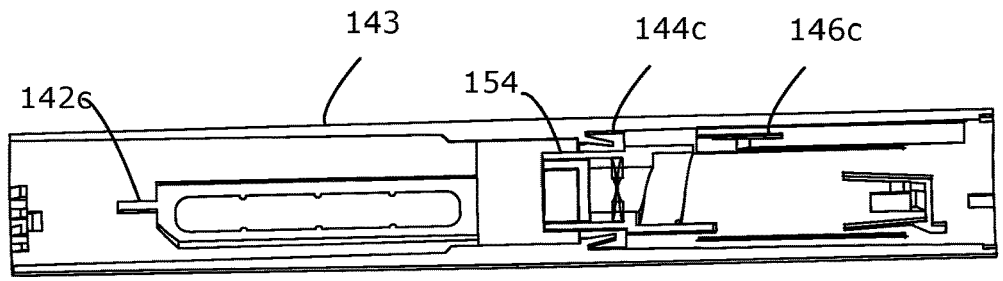
Figure 3D:
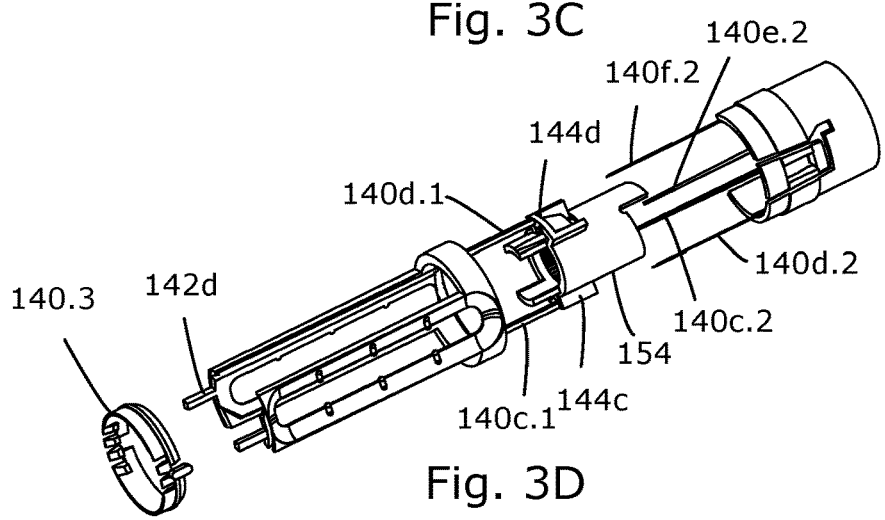
Figure 3E:
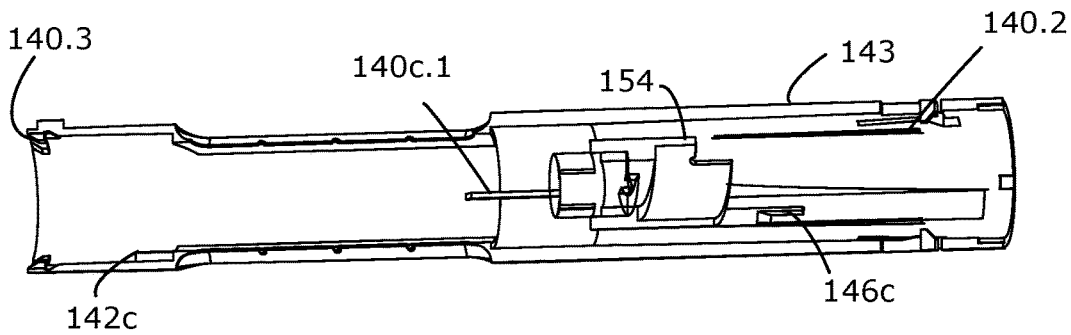
Figure 3F:
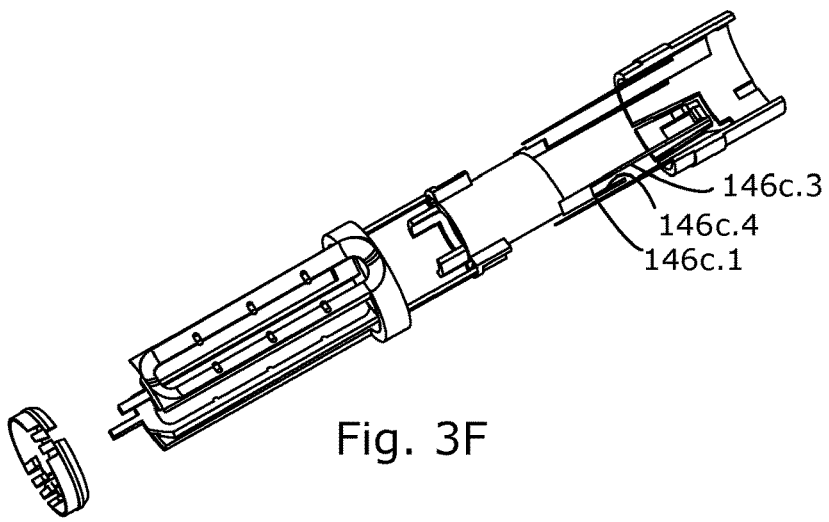

FIG. 3C corresponds to the cut shown in FIG. 3A, wherein the inner tubular portion 154 is left in. It is noted that the middle guide 144 is positioned in the annular space between the outer tubular portion 143 and the inner tubular portion 154. FIG. 3D illustrate in perspective view the housing structure 140, wherein a tubular cut has been made. The tubular cut is made in a plane containing the inner surface of the housing structure and the cut removes structures on the outside of that plane. Thereby only structures on the inner surface is visible. FIG. 3D shows the internal connecting structures 140.3 for connecting with the housing insert portion 160. The connecting structures 140.3 are adapted for angular positioning the insert portion with respect to the housing structure 140. FIG. 3D further shows ribs 140.1 which together with the radial surfaces of guides 142 support the radial center position of the shield structure 110. The proximally positioned ribs 140.2 support the radial position of the return spring 107. At the proximal end, proximal to the ribs 140.2, is shown a portion of the elongate housing structure 140. FIG. 3E corresponds to the cut shown in FIG. 3B, wherein the inner tubular portion 154 is left in, like in 3C. FIG. 3F shows a perspective view as in 3D, but the structures are seen from a different angle revealing details of the proximal guide 146c. Proximal guide 146c is seen as the edge about the recess although the edge is positioned in the plane with the inner surface. As seen the guides 142, 144, 146 are provided in two-fold rotational symmetry. For the proximal guide 146c, the other rotationally shifted guide is not visible due to the angle of the perspective view.

Therefore, FIG. 3A through 3F collectively show the technical details of the housing structure 140 according to the first embodiment. The distal guide 142 of the housing is adapted for guiding the shield in the rotational and the axial direction along a connected guide surface comprising the first axial portion 142.1, the first transverse portion 142.2, the second axial portion 142.3, and the second transverse portion 142.4. The middle guide is adapted for guiding the connector in the rotational and the axial direction and comprises the proximal transverse portion 144.1, the first axial portion 144.2, the distal transverse portion 144.3 and the second axial portion 144.4. As explained later the first axial portion 144.2 of the middle guide 144 further provides a rotational stop for the shield 110 during injection. The proximal guide is adapted for guiding the connector through a work cycle in the axial and the rotational direction and comprises the first axial portion 143.1 providing a rotational stop and adapted for guiding a proximal axial movement, a first transverse portion 146.2 for guiding a rotational counterclockwise movement, the second axial portion 146.2 providing a rotational stop and adapted for guiding a distal axial movement together with the third axial portion 146.3. The proximal guide further comprises the ramp portion 146.5 and the flush portion for guiding the connector back to the beginning of the working or dosing cycle.

Zero-Point-Adjustment Mechanism

FIGS. 4A and 4B show a perspective view of a zero-point-adjustment nut 106, according to an alternative embodiment of the present disclosure. As shown, the distal face is visible at the distal end 106a in FIG. 3A and the proximal face in FIG. 3B is visible at the proximal end 106b. The adjustment nut 106 comprises an internal thread 106.1 for engaging an outer thread 109.1 of the piston rod 109 and an outer thread portion 106.2 for engaging an inner thread 154.2 of the housing. The outer thread 106.2 is in the illustrated embodiment shown as two outer thread portions provided proximally on the nut 106 and protruding from the outer surface. The outer thread 106.2 can be made from any number of outer thread portions. Alternatively, the thread connection 106.2, 154.2 between the nut 106 and the housing can be substituted by a pure rotational guide.

Furthermore, on the outer surface of the adjustment nut 106 is provided a ratchet arm 106.3. In the disclosed embodiment, two ratchet arms 106.3c and 106.3d are positioned in two-fold rotational symmetry at the distal end 106a of the adjustment nut 106. Any suitable number of ratchet arms 106.3 can be provided. However, to increase rotational stability of the adjustment nut 106 at least two ratchet arms in rotational symmetry is preferred. Two-fold rotational symmetry implies that rotation by a 180-degree angle about a central axis of the nut 106, does not change the appearance of the nut 106.

FIG. 5 shows in perspective view the elongate housing structure 140 cut in a half, whereby an inner surface of the structure is visible. The elongate housing structure defines a distal end 140a and a proximal end 140b. As also seen on the figure, on the inner surface of the elongate housing structure 140 is provided the inner tubular portion 154 adapted to support the adjustment nut 106. The inner tubular portion 154 is also illustrated as a half tube due to the cut. The illustrated embodiment is provided with an axial toothing 154.3 adapted to engage with a ratchet arm 106.3 of the nut, which allows the adjustment nut 106 to rotate in one direction only. The allowed rotational direction being clockwise, which means that the ratchet arm 106.3 and the toothing 154.3 interface prevents counterclockwise rotation of the nut relative to the housing. The prevented or blocked direction of the adjustment nut 106, is the same direction as the direction of rotation of the piston rod, as it advances in the distal direction during dosing. In this way, the adjustment nut cannot be accidentally displaced during dosing.

In some embodiments, the inner tubular portion 154 is further provided with the internal thread 154.2 having a direction such that the adjustment nut 106 is helically screwed in the proximal direction when rotated in the allowed clockwise direction. Thereby, the thread connection 106.2, 154.2 between the nut and the housing provides an additional gearing between rotation of the adjustment nut 106 and the axial displacement of the rotationally fixed piston rod 109, which for example can be useful to compensate for a relatively large pitch thread connection between the adjustment nut 106 and the piston rod 109.

During assembly of the injection device it is desirable to ensure that the distance or air gap between the piston rod 109 and the piston 136 inside the cartridge 135 is minimized. Minimization of the air gap ensures that the drug is expelled from the reservoir, in response to moving the piston rod 109 in the distal direction. If a washer 104 is attached to the piston rod 109 as disclosed in a preferred embodiment shown in FIG. 6, the object is to minimize the air gap between the distal surface of the washer 104 and the proximal surface of the piston 136 such that the washer 104 and the piston 136 abut each other, when the injection device is arranged in a state allowing storage, and wherein the device is ready for being delivered to the end user. In the following, air gap elimination will be described with reference to the piston rod abutting the piston, but the same considerations apply when the air gap is to be eliminated between the piston and the washer.

When the adjustment nut is rotated relatively to the housing structure during final assembly, the piston rod 109 is advanced helically in the distal direction until the piston rod 109 or the washer 104 abut the piston 136 inside the cartridge 135. In embodiments comprising the thread connection 106.2, 154.2 between the nut and the housing, the advancement of the piston rod relative to the housing is compensated or counteracted by the proximal movement of the adjustment nut relative to the housing.

The rotation of the adjustment nut is preferably done by using a special tool in the production line which is adapted to engage the adjustment nut and transfer a rotation to the adjustment nut. In one preferred example, the piston rod 109 is arranged in engagement with the adjustment nut to provide a subassembly, and the subassembly is then arranged in the inner tubular portion 154 of the housing. Hereafter, electronic computerized equipment is used to detect the relative position of the piston 136 in the cartridge 135 to be used for that specific injection device. When the position of the piston 136 and the position of the piston rod 109 has been obtained, the computer can determine the required angular displacement of the arranged adjustment nut 106 to position the piston rod in abutment with the piston 136, when the injection device is assembled.

During assembly, the position of the proximal end of the piston rod 104 is thus adjusted by rotating the adjustment nut in the one-way interface with the inner tubular portion 154. It is here important that the adjustment nut can rotate in the direction, which advances the piston rod 109 into contact with the piston 136.

After assembly, the piston rod 109 or washer 104 abuts the piston 136 it is not possible to rotate the adjustment nut further in the clockwise direction. Furthermore in any of the assembled states, there are no external interfaces between the nut 106 and the external surroundings. Therefore, there are no possibilities of contacting the external surfaces with an external tool, and applying an external torque to the nut.

The result of the above is that the adjustment nut 106 is self-locking in relation to the housing structure and it is not necessary to physically secure the nut 106 to the housing. It is henceforth not necessary to weld or glue the nut member 11 to the housing.

Drive Mechanism

Figure 6:
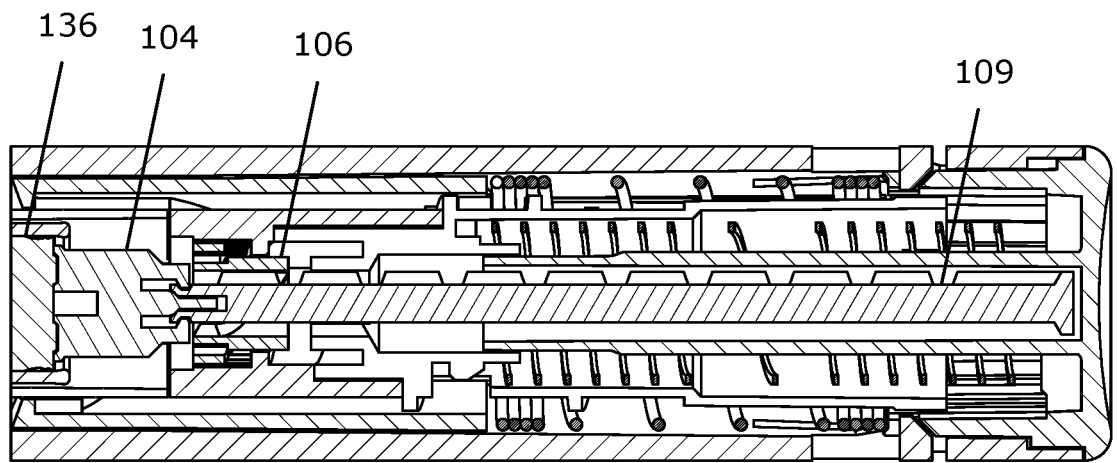
FIG. 6 illustrates a cross sectional view of the proximal portion of the injection device of the embodiment of FIG. 1A. The illustrated injection device comprises a piston washer.
Figure 7:
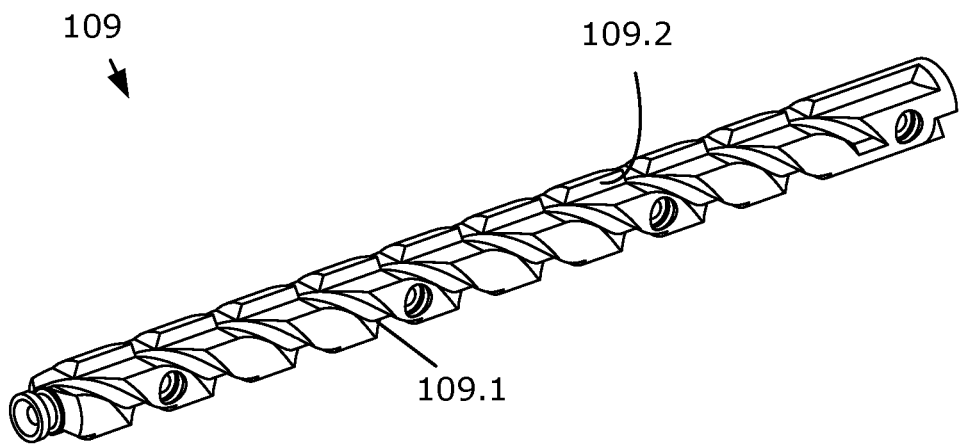
FIG. 7 shows details of the piston rod of the embodiment shown in FIG. 1A.
Figure 8A:
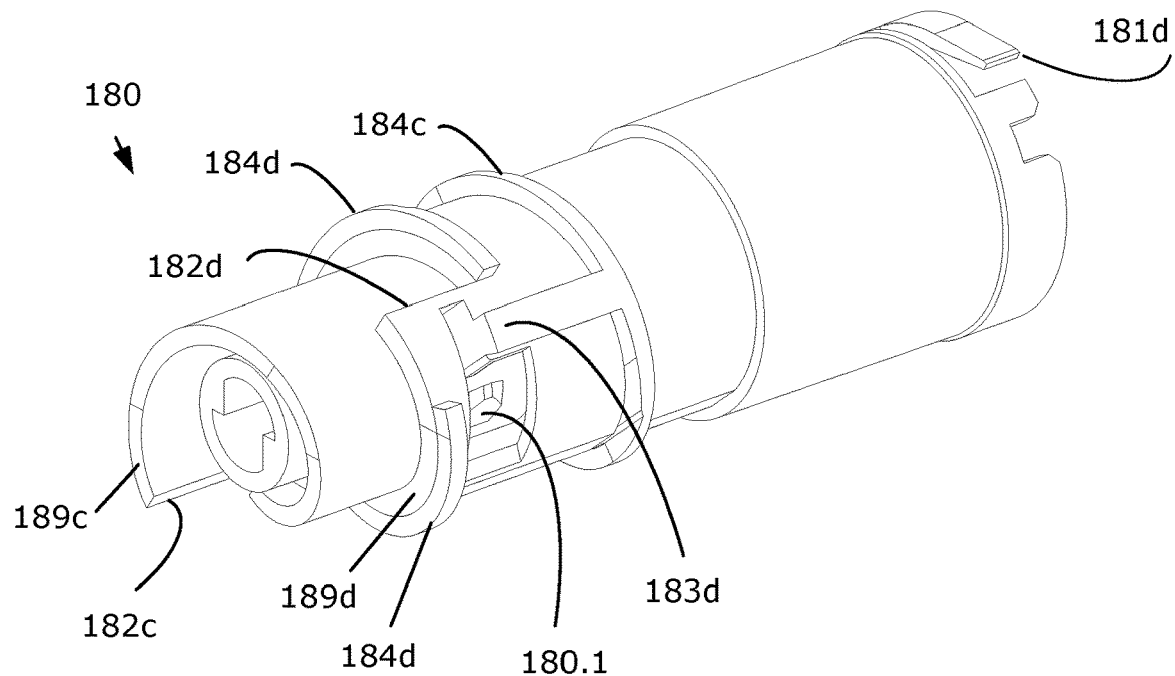
FIGS. 8A-8B show details of the drive tube of the embodiment shown in FIG. 1A.
Figure 8B:
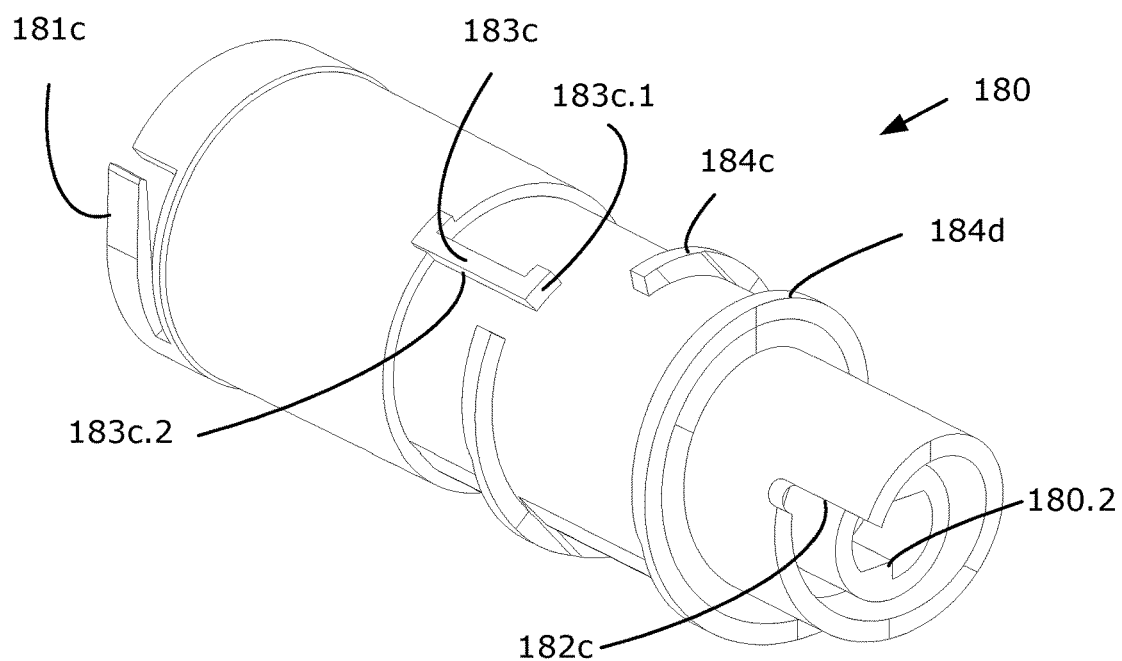

FIG. 6 shows a cross sectional view of a proximal portion of the injection device, after zero-point adjustment between the piston 136 and the washer 104. The piston rod 109 is positioned at a proximal position indicating that a first dose has not been expelled. FIG. 7 shows a perspective view of the piston rod 109 and illustrates in detail the outer thread 109.1 and an axial track 109.2. FIGS. 8A and 8B illustrate the drive tube 180 in perspective views from different angles. The figures show a tab 183c protruding from an outer surface and providing a structure for cooperating with the connector 170 during activation of the drive tube 180 and for relocking of the shield structure 110 after a dose has been expelled. The tab 183 comprises a distally oriented surface 183.1 (a distal surface or a distally oriented surface means that at least a component of the normal vector is oriented in the distal direction) and an axial portion 183.2 providing a surface oriented in the angular direction for cooperating with the connector 170. The figure also shows a helical structure 184c protruding from the outer surface and being adapted for axially blocking the connector during dosing, in response to an immature attempt of stopping a dose. The tab 183 is positioned proximally to a transverse opening provided in the helical structure 184. The figure further illustrates an axial surface 182c adapted for cooperating with the housing during activation and for providing a rotational stop defining the end of a dose. Features 182, 183 and 184 will be explained in detail later in the application.

The drive tube 180 is provided with inward protrusions 180.2 protruding from an inner surface and adapted to engage the axial track 109.2 of the piston rod 109. The piston rod 109 is adapted to be slidably arranged in the drive tube, whereby relative axial displacement is allowed, but relative rotation is prevented. The drive tube 180 is provided with a ratchet arm 181c for engaging a toothing 165.1 inside the tubular spring base 165, and thereby forming a one-way ratchet interface such that the drive tube 180 is only rotational in one direction, which in the disclosed example is the counterclockwise direction for dispensing a dose. The ratchet arm 181c thus prevents rotation of the piston rod 109 in the clockwise direction. In the illustrated example the drive tube comprises two ratchet arms 181c, 181d arranged in 2-fold rotational symmetry. The ratchets arms 181 provides a dose clicking sound during expelling, in response to the drive tube 180 and the piston rod 135 rotating in the counter clockwise direction.

The engagement between the piston rod 109 and the drive tube 180 prevents relative rotation. Therefore, as the adjustment nut 106 during zero-point adjustment is rotated in the clockwise direction, the nut induces a distal translation of the piston rod 109, since the drive tube is locked against rotation in the clockwise direction.

The torque delivering drive spring 108, shown in FIG. 1, is in an embodiment according to the disclosure arranged inside the drive tube 180, and at each end fixedly attached to the drive tube and the spring base 165. The distal end comprises distal attachment means 108.1 fixedly attached to the drive tube 180, and proximal attachment means 108.2 fixedly attached to the spring base 165. The drive spring is winded up or strained during assembly, and thereby stores energy to rotate the drive tube with a sufficient torque and thereby deliver the plurality of doses without further straining.

Incorporating a torsion spring in the drive mechanism provides several advantages. The inventors of the present invention realized that for an embodiment constructed with a compression spring, the compression spring advances into the cartridge as it releases energy. If the injection device is designed without allowing the compression spring advancing into the cartridge, the overall length of the device will increase. Therefore, in a construction of limited length the diameter of the spring is limited by the diameter of the cartridge. The inventors of the present invention found that as a torsional spring does not have to extend into the cartridge in order to limit the overall length of the device. Therefore, the torsional drive spring is not limited by the diameter of the cartridge or the piston rod and is advantageous in a construction of limited length.

The torsional drive spring according to an embodiment of the present disclosure is arranged proximal to the cartridge and on the outside of the piston rod 109. Thereby, the torsional drive spring allows the spring to enclose a larger volume, and thereby increase the mass, i.e., the amount of spring material (e.g. steel). In other words, as the used material or mass can be increased, the performance relating to long term storage and dosing can be improved. With increased mass, internal stress of the spring can be reduced, and/or the spring profile can be flatter thus minimizing the variation in dose time between the first and last dose of the device. The inventors of the present invention also found that if the maximum internal stress of the spring is reduced, the stress induced in the plastic components supporting the spring is also reduced, which is necessary in order to allow long term storage.

The inventors of the present invention further found that in an embodiment, wherein the torsional drive spring is arranged inside the drive tube, the drive tube can be adapted to provide dose clicks and allows an increase of the number of dose clicks by increasing the diameter. Therefore, the number of dose clicks can be increased without extending the axial length of the device.

According to an embodiment of the present disclosure, the outer surface of the drive tube comprises a dose click providing structure adapted to provide dose clicks, e.g., a ratchet arm riding over teeth provided on a surrounding structure. Alternatively, the ratchet arm is provided on the surrounding structure and the teeth on the drive tube. As the circumference of the outer surface of the drive tube 180 increases with the diameter of the drive tube, so does the number of dose clicks. In the case of a rotational drive tube, the number of dose clicks is determined as the relation between the circumference of the drive tube and the distance between the dose click providing structures, e.g., distance between the teeth (number of dose clicks=2*pi*radius/distance between teeth). Therefore, the number of dose clicks can be increased by increasing the radius, but without increasing the length of the spring and thereby the device. In contrast, in order to increase the number of dose clicks for a piston driven by a compression spring arranged in the piston, the length of the compression spring has to be increased. In the case of a compression spring, the number of dose clicks is determined by the axial extension of the spring divided by the distance between the teeth (number of dose clicks=axial extension/distance between teeth).

Furthermore, the inventors of the present invention found, that the required energy to release a triggering mechanism, i.e., the activation energy, is a function of the internal stress of the drive spring. Therefore, activation of the dose engine enabled with a torsional drive spring requires less force than a similar design based on a compression spring.

In addition, the inventors found that an embodiment comprising a drive mechanism based on a torsional drive spring is easier to assemble than an embodiment based on an equivalent compression drive spring. Compared to the compression spring, the torsional spring is relatively short and is thus easier to handle.

The rotating drive tube is easily adapted to function with an electronic dose capturing device, which register a rotating structure during dosing, as described in WO 2019/110494, titled "Drug delivery system with multipolar magnet and sensor system".

Housing Insert Portion

Figure 9A:
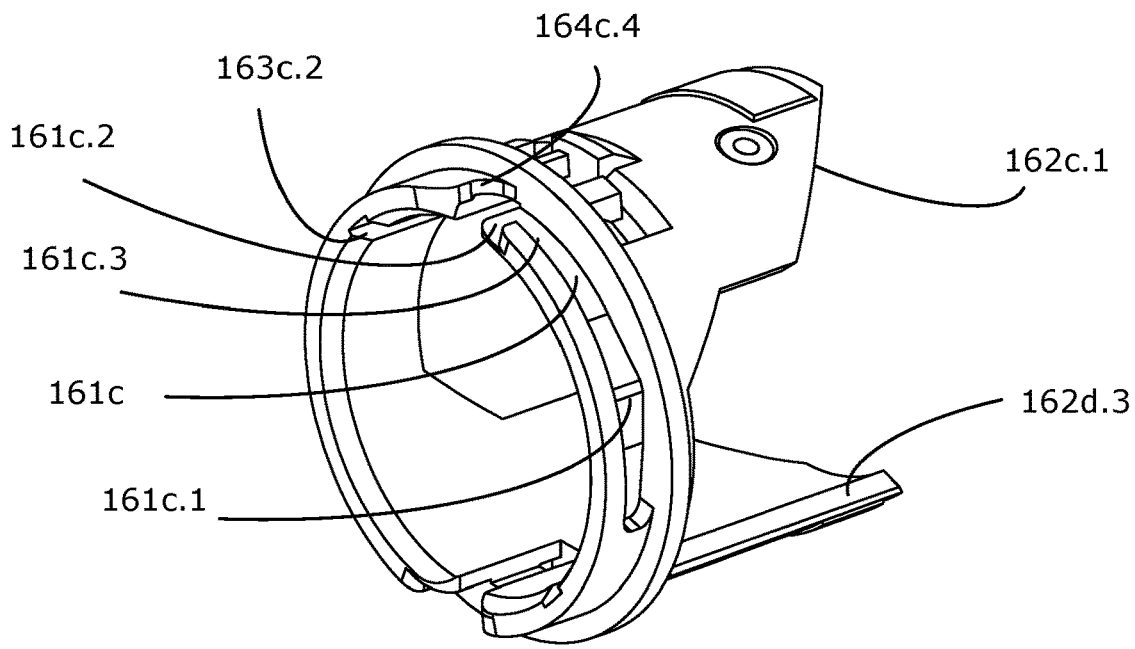
FIGS. 9A-9B show details of the housing insert portion of the embodiment shown in FIG. 1A.
Figure 9B:
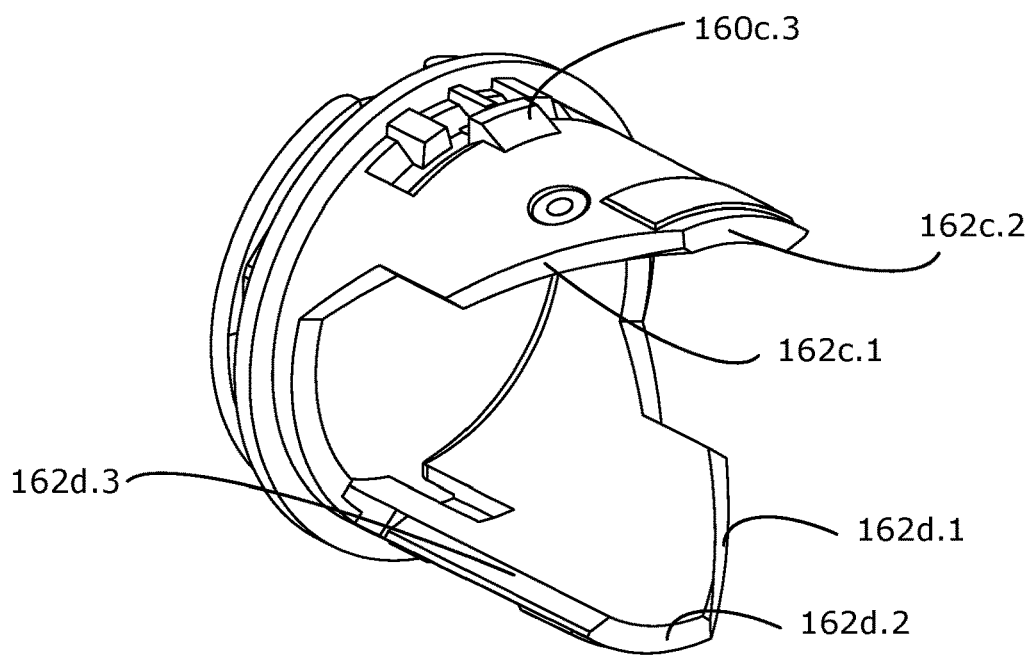

FIGS. 9A and 9B illustrate two different perspective views of the housing insert portion 160 to be fixedly mounted at the distal end of the elongate housing structure 110, via alignment structures and snap structure 160c.3. The housing insert portion comprises a cap mount track 161. As seen, the cap mount track 161c comprises an axially extending track portion 161c.2 with a proximal and a distal end, and a circumferentially extending track portion 161c.3 with a first end and a second end. At the first end of the circumferential track is positioned a snap lock 161c.1, and the second end is connected to the proximal end of the axially extending track 161c.2, whereby the track portions form a track for a bayonet coupling for cooperating with an inner protrusion of the cap 105. At the second end of the track 161c is also provided a rotational stop 161c.4. The housing insert portion 160 further comprises an axially extending slit 163c, on an inner surface for cooperating with an axially extending rib 116c on an outer surface of the shield (see FIG. 10A), as will be explained later. The inner housing portion 160 further comprises a proximal guide 162 for guiding the shield 110. The illustrated proximal guide 162d extends in the circumferential direction, and in a counter clockwise direction the guide comprises a helical portion 162d.1, a transverse portion 162d.2 with zero pitch and an axial portion 162d.3. Alternatively, to a bayonet coupling a thread coupling can be used.

Elongate Shield Structure

FIGS. 10A and 10B show perspective views of the cylindrical elongate shield structure 110 to be arranged inside the tubular housing 140. On FIG. 10A the distal face of the shield structure 110 can be seen, and on FIG. 10B the proximal face can be seen. FIG. 10C shows a portion of the shield structure in perspective side view. The elongate shield structure 110 comprises a tubular portion comprising an outer surface with an outer diameter and an inner surface with an inner diameter. The axially extending rib 116c is arranged at the distal end ant protrudes from the outer surface. The rib is adapted for cooperating with the internal rib of the cap 105, and for cooperating with the slit 163 on the inner surface of the housing insert portion 165.

The shield structure 110 further comprises a step-wise helical guide 112 arranged on the outer surface and adapted for cooperating with the proximal guide 162 of the housing insert portion and the distal guide 142 of the housing. The step-wise helical guide 112 is provided in the annular space between the outer surface of the tubular portion of the shield structure 110 and the inner surface of the outer tubular portion 143 of the housing. The step-wise helical guide comprises a continuous protruding structure extending in the axial and circumferential direction and comprises a proximal transverse protruding portion, a proximal left-handed helical protruding portion, a middle transverse protruding portion, a distal left-handed helical protruding portion, a distal transverse protruding portion. The continuous protruding structure comprises a plurality of axially and circumferentially oriented surface portions providing the guide surfaces (a circumferential surface or a circumferentially oriented surface means that at least a component of the normal vector is oriented in the circumferential direction). The surface portions can be seen on FIG. 10 and are referred to with the following terms and reference numbers. A proximal axial guide portion 112.1, a first proximal transverse guide portion 112.2, a second proximal transverse guide portion 112.3, a first proximal helical guide portion 112.4, a second proximal helical guide portion 112.5, a first middle transverse guide portion 112.6, a second middle transverse guide portion 112.7, a first distal helical guide portion 112.8, a second distal helical guide portion 112.9, a first distal transverse guide portion 112.10, a second distal transverse guide portion 112.11 and a distal axial guide portion 112.12. In this way the guide portions 112.2, 112.4, 112.6, 112.8 and 112.10 provides a distal face of the stepwise helical guide 112, and the guide portions 112.3, 112.5, 112.7, 112.9 and 112.11 provides a proximal face.

The elongate shield structure 110 further comprises a proximal guide 114 positioned at the proximal end of the shield structure 110. On FIG. 10A the distal face can be seen, and on FIG. 10B the proximal face can be seen. The proximal guide 114 is adapted to cooperate with the connector 170 and the middle guide 144 of the housing. The proximal guide 114 extends in the axial and circumferential direction and comprises a first left-handed helical portion 114.1, a first right-handed helical portion 114.2, a second right-handed helical portion 114.3, a second left-handed helical portion 114.4, a first axial portion 114.5, a first transverse portion 114.6, a second axial portion 114.7, a third axial portion 114.8 and a second transverse portion 114.9.

The guide portions 114.1-114.9 are all surface portions and the guide portions 114.1, 114.2, 114.3, 114.4 and 114.9 provides a proximal face of the proximal guide 114, and the surface portion 114.6 provides a distal face, i.e., viewable from proximal and distal position, respectively. The guide portions 114.1, 114.2, 114.3 and 114.4 of the proximal face are adapted for cooperating with the connector during activation operations.

The guide portion 114.6 of the distal face of the proximal guide is adapted for cooperating with the connector during dosing, in response to premature release of pressure on the shield, which will be explained in detail later in the application.

The third axial portion 114.8 is adapted for cooperating with the middle guide 144 of the housing and provides a rotational stop, preventing further counterclockwise rotation of the shield, with respect to the housing and during dosing. Similar, the second transverse portion 114.9 provides an axial stop cooperating with the middle guide 144 and prevents further proximal movement of the shield during dosing.

The proximal guide 114 comprises a locking structure 115 comprising the guide portions 114.4 and 114.5, in the illustrated embodiment the locking structure 115 is a part of a hook resembling structure. As will be explained in detail later, the locking structure 115 is adapted for releasably locking to a corresponding hook resembling structure of the connector 170 during dosing.

The shield further comprises a click-arm 113, with an axial surface portion 113.1 providing a rotational stop. In an initial state the click-arm is radially compressed by an inner surface of the housing insert portion 160.

Connector

Figure 11A:
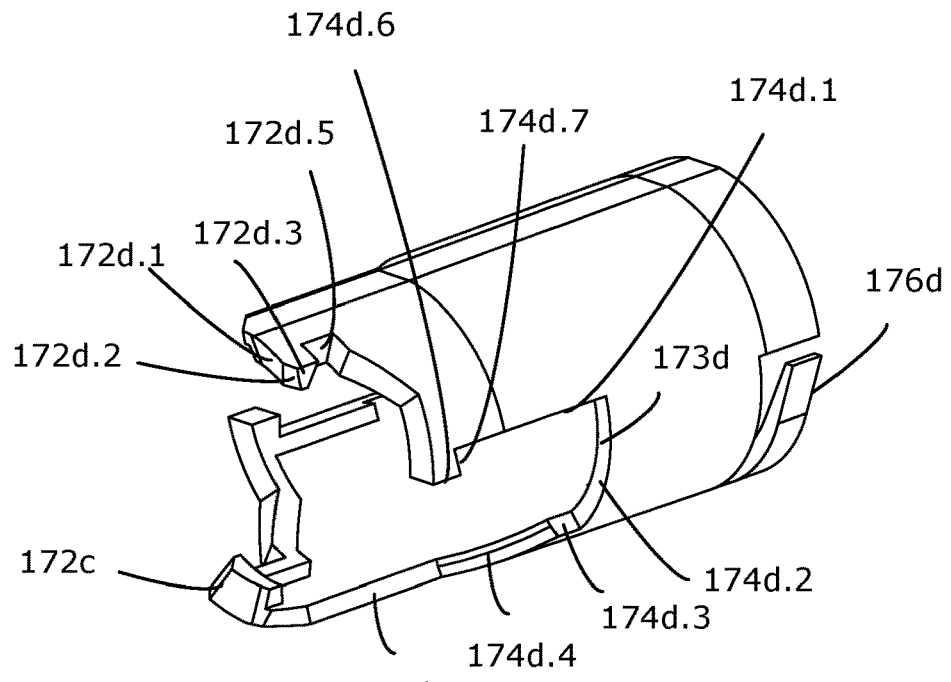
FIGS. 11A-11B show details of the connector of the embodiment shown in FIG. 1A.
Figure 11B:
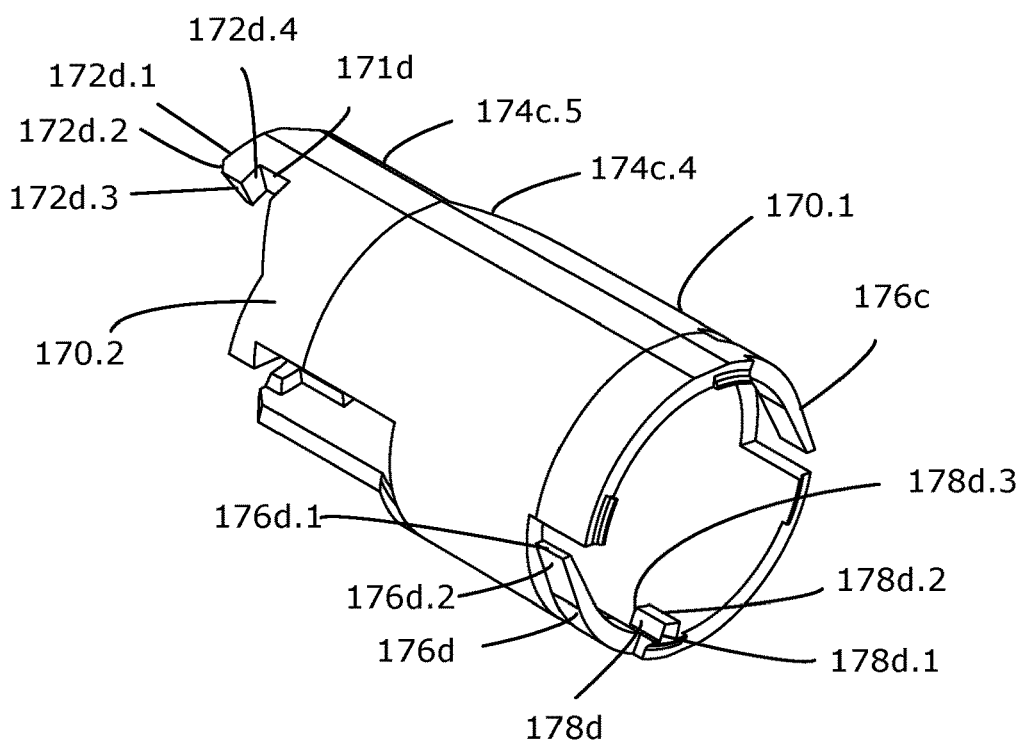

FIGS. 11A and 11B show perspective views of the connector 170 to be arranged inside the tubular housing 140 and between the elongate shield structure 110 and the drive tube. The connector 170 is adapted for establishing a connection between the shield and the drive tube, and for activating the drive tube 180. The connector 170 is further operatively connected in a an automatic relock mechanism adapted for automatically relocking the shield at the end of a dose. The connector 170 comprises a distal guide 172 adapted to cooperate with the proximal guide 114 of the shield. The distal guide 172 is extending in the circumferential and the axial direction and comprises a left-handed helical portion 172.1, a right-handed helical portion 172.2, a first axial portion 172.3, a transverse portion 172.4 and a second axial portion 172.5.

The guide portions 172.1-114.5 are all surface portions and the guide portions 114.1 and 114.2 provides a distal face of the distal guide 172, and the surface portion 172.4 provides a proximal face. The guide portions 172.1 and 172.2 of the distal face are adapted for cooperating with the proximal guide of the shield during activation operations. The guide portion 172.4 of the proximal face is adapted for cooperating with the guide portion 114.6 of the proximal guide of the shield during dosing, in response to premature release of pressure on the shield, which will be explained in detail later in the application.

The return spring 107 urges the connector in the distal direction. Therefore, the left-handed helical portion urges the connector in a clockwise direction and the shield in a counterclockwise direction, in response to establishing an engagement between the left-handed helical portion 172.1 and the first left handed helical portion 114.1 of the proximal guide of the shield, or in response to establishing an engagement between the left-handed helical portion 172.1 and the second left handed helical portion 114.1 of the proximal guide of the shield.

The distal guide 172 comprises a locking structure 171 comprising the left-handed helical portion 172.1 and the first axial portion 172.3. The locking structure 171 is a part of the hook resembling structure adapted for releasably locking to the corresponding hook resembling structure of the proximal guide 114 of the shield. The releasable lock between the hook resembling structures is established, in response to the second left-handed helical portion 114.4 of the locking structure 115 of the shield is brought into abutment with the left-handed helical portion 172.1 of the locking structure 171 of the connector under axial compression from the return spring 107. Hereby, the shield is urged in the counterclockwise direction and the connector is urged toward the counterclockwise direction, and abutment is established between the first axial portion 172.3 of the connector and the first axial portion 114.5 of the shield. In order to release the lock, the friction established in the abutment between the two left-handed helical portions 114.4 and 172.1 has to be exceeded, in response to a counter clockwise rotation of the connector.

The connector 170 comprises a tubular portion 170.1 with a full 360 degree circumference, and two axially extending tube portions 170.2 formed by two cut-outs in the tube and thereby only providing a fraction of the circumference. The connector 170 is having an outer surface with an outer diameter and an inner surface with an inner diameter. As illustrated on FIGS. 12A and 12B, which are cross sectional views of a proximal end of the injection device, the outer surface of the connector is arranged in close proximity with the inner surface of the outer tubular portion 143 of the housing. The connector surrounds the inner tubular portion 154 of the housing and the drive tube 180. The inner diameter of the connector is larger than the outer diameter of the tubular portion of the shield structure 110, therefore the guide portions 172.1-172.4 are provided with a shoulder projecting in the negative radial direction for enabling the contact between the proximal guide 114 of the shield and the distal guide 172 of the connector.

The connector further comprises a middle guide 174 adapted to cooperate with the middle guide 144 of the housing and thereby control the position of the connector relative to the housing. The middle guide of the connector extends in the axial and circumferential direction and comprises: a first axial portion 174.1 providing a rotational stop, a first transverse portion 174.2, a second axial portion 174.3, a left-handed helical portion 174.4, a third axial portion 174.5., a fourth axial portion 174.6, and a second transverse portion 174.7.

The middle guide 174 of the connector defines a blocking structure comprising the second transverse portion 174.7 adapted to prevent unintended axial movement of the connector and thereby unintended activation of the drive tube 180.

The middle guide 174 further defines a seat or locking structure 173 comprising the first transverse portion 174.2 and the second axial portion 174.3, wherein the locking structure is adapted to provide a rotational lock to prevent rotation and distal movement of the connector in an initial position. In the initial position the connector 170 is in its distal most position.

The connector 170 further comprises an activation tab 178 arranged on and extending radially from the inner surface in a negative radial direction. The activation tab 178 comprises a first transverse portion 178.1 providing a proximal contact surface adapted for activating the drive tube 180. The activation tab further comprises an axial portion 178.2 adapted for releasing the automatic relock mechanism, in response to an impact in the clockwise direction from the drive tube 180, and a second transverse portion 178.3 providing a retention portion preventing a split-dose in response to premature release of pressure on the shield.

The connector further comprises a proximal guide in the form of a click arm 176 adapted to cooperate with the proximal guide 146 of the housing. A circle circumscribing the two-fold symmetrically arranged click arms 176c and 176d in their relaxed state defines a diameter larger than the outer diameter of the connector and larger than the inner diameter of the housing. Therefore, in response to arranging the connector 170 inside the outer tubular portion 143 of the housing with the click arms 176 contacting the inner surface, deflects the click arm in the negative radial direction. In this position, the click arms 176 exerts a radial force in the radial direction on the inner surface of the housing. The click arm comprises a first axial portion 176.1 for cooperating with the axial guide portions 146.1 and 146.3 of the proximal guide of the housing, and an outer surface portion 176.2 extending in the axial and circumferential direction adapted for cooperating with the axial portion 146.4, the ramp portion 146.5 and the flush portion 146.6.

Proximal Portion of Injection Device

Figure 12A:
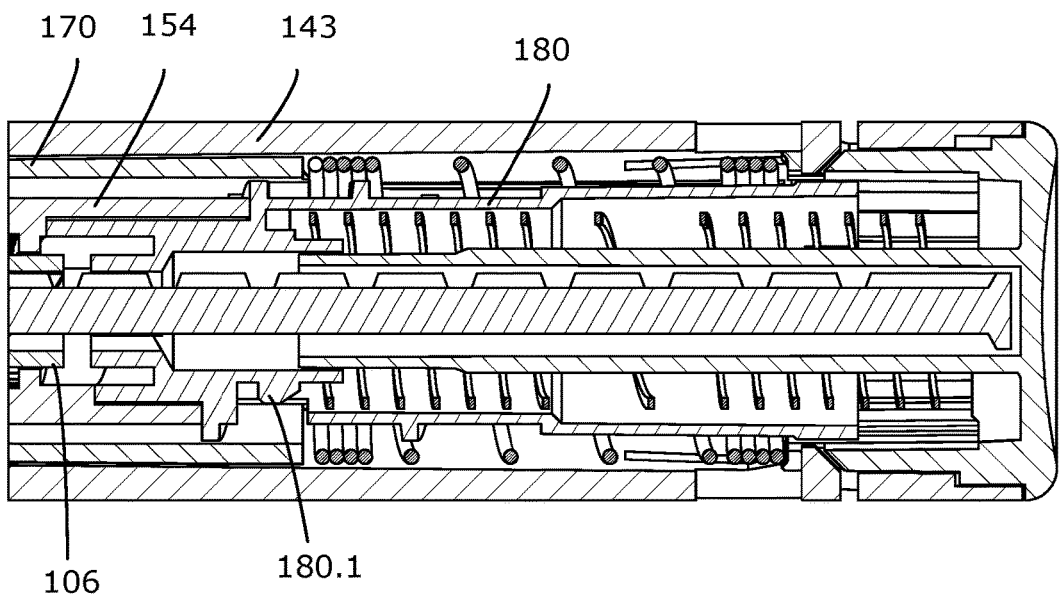
FIGS. 12A-12B show cross sectional views of the proximal end of the injection device from two different angles. The illustrated device is the same as the embodiment shown in FIG. 1A.
Figure 12B:
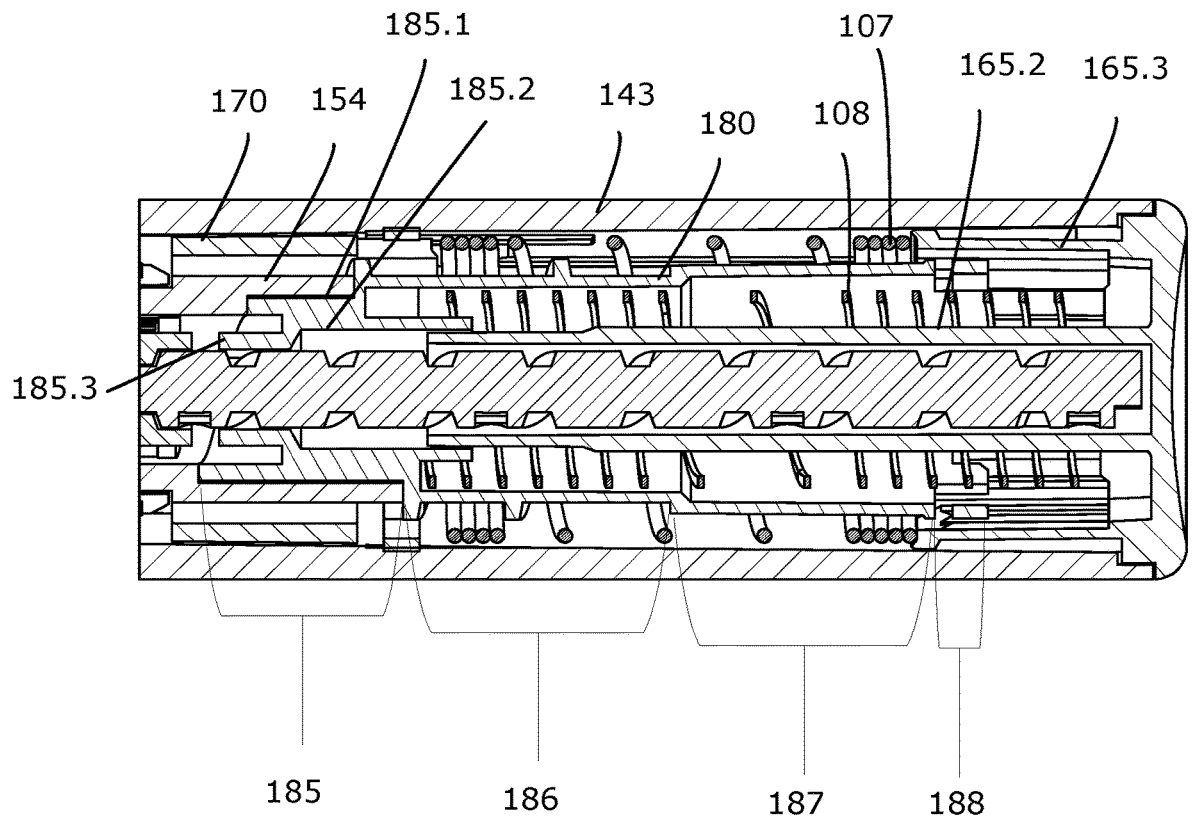

Returning to FIGS. 12A and 12B. FIGS. 12A and 12B illustrates cross sections of a proximal end of the device. FIG. 12A illustrates a central cross section comprising the windows 141 (although they are positioned on the distal portion of the device which is not visible in FIG. 12). FIG. 12B illustrates a central cross section rotated 90 degrees relative to FIG. 12A. The drive tube 180 comprises 4 tubular portions, as indicated on FIG. 12B. A first tubular portion 185, a second tubular portion 186, a third tubular portion 187 and a fourth tubular portion 188.

The first tubular portion 185 is also the distal tubular portion and is arranged inside the inner tubular portion 154 of the housing. The distal tubular portion comprises an outer tubular portion 185.1 in contact with the inner tubular portion 154. The outer tubular portion 185.1 is connected to the second tubular portion 186 and further comprises the axial surface portion 182c adapted for cooperating with the housing during activation and for defining the end of the dose. The outer tubular portion 185.1 further comprises a distal helical surface portion 189c adapted for cooperating with a proximal helical surface portion of the inner tubular portion 154 of the housing during dosing (see also FIG. 8A).

The distal tubular portion 185 further comprises an intermediate tubular portion 185.2 extending in the proximal direction. The proximal portion of the intermediate tubular portion 185.2 is surrounded by the second tubular portion 186, and thereby defines an annular spring accommodating space providing a distal base for the drive spring 108. The outer surface of the proximal portion of the intermediate tubular portion 185.2 defines a spring snap 180.2 for axially snapping to the drive spring 108, in response to an axial insertion of the drive spring into the annular spring accommodating space. The distal tubular portion 185 further comprises an inner tubular portion 185.3 extending distally from the intermediate tubular portion and comprises the inward protrusions 180.2 adapted to engage the axial track 109.2 of the piston rod 109.

The second tubular portion 186 comprises the protruding helical structures 184c and 184d on the outer surface. The second tubular portion 186 further comprises the axial surface portion 182d, arranged in two-fold rotational symmetry with axial surface portion 182c, adapted for cooperating with the housing during activation and for defining the end of the dose. The second tubular portion 186 further comprises a distal helical surface portion 189d, arranged in two-fold rotational symmetry with distal helical surface portion 189c, adapted for cooperating with a proximal helical surface portion 157d of the inner tubular portion 154 of the housing during dosing (see also FIGS. 8A, and 13A). The protruding helical structures 184 protrudes from the outer surface of the second tubular portion 186 and extends to the inner surface of the connector 170. The helical structures 184 are adapted for axially blocking the connector during dosing, in response to immature release of the pressure on the connector, whereby the helical structures 184 will block the axial movement of the activation tab 178 protruding inwardly from the inner surface of the connector 170.

The second tubular portion 186 and the third tubular portion 187 is surrounded by the return spring 107. Together with an inner tubular portion 165.2 of the spring base 165, the second and third tubular portions 186, 187 defines an annular space accommodating a portion of the drive spring 108. The fourth tubular portion 188 of the drive tube 180 is also the proximal tubular portion and comprises ratchet arm 181c for engaging the toothing 165.1 inside an outer tubular portion 165.3 of the spring base.

Activation Mechanism

FIG. 13A illustrates a perspective view of the inner tubular portion 154 of the housing and the drive tube 180, wherein the distal tubular portion 185 has been inserted into the inner tubular portion 154, and is therefore not visible on the figure, here the drive tube 180 is in a home position. Before the first dose the home position is also referred to as a starting position. After a first dose, the home position is also referred to as an end of dose position. FIG. 13B illustrates a cross section along the indicated line C-C and viewed from the proximal end. FIG. 13C illustrates the cross section C-C viewed from the distal end.

FIG. 13A further illustrate the activation tab 178 of the inner surface of the connector 170 (only the tab and not the rest of the connector is shown on FIG. 13A). The connector with the activation tab 178 is arranged in a position where it contacts the protruding tab 183, and is thereby ready to transfer a proximal movement to the drive tube, whereby the drive tube can be activated. The drive tube 180 is biased by the drive spring in a distal and counterclockwise direction. In FIG. 13A, the drive tube is illustrated in a rest position, wherein the axial surface portion 182 abuts an axial surface portion 156 of the inner tubular portion 154 of the housing, and thereby prevents counterclockwise rotation of the drive tube 180. In the rest position the distal helical surface portion 182 also abuts the proximal helical surface portion 157 of the inner tubular portion 154 of the housing, and thereby prevents distal movement of the drive tube 180.

FIG. 13D illustrates in details a proximal end of the helical surface portion 157d.1 defining a starting point of a helical dosing track and a distal end of the helical surface portion 157d.2 defining an ending point of the helical dosing track. Similarly, the distal helical surface portion 189d defines a front point or edge 189d.1 and a trailing point or edge 189d.2. In response to moving the connector in the proximal direction the activation tab 178, when arranged in in abutment with the protruding tab 183, induces a proximal movement of the drive tube 180. Thereby, the front edge 189d.1 is moved proximally along the axial surface portion 182d until it passes a proximal end of the axial surface portion and reaches the starting point 157d.1 of the helical dosing track. Due to the counterclockwise bias of the drive tube 189, the drive tube 189 rotates in the counterclockwise direction, and due the distal bias the front edge 189d.1 is forced into contact with the helical dose track of the inner tubular portion 154. Hereafter, the drive tube with the front edge 189d.1 travels along the helical dose track in a distal helical movement until it reaches the ending point 157d.2. A small dimple is noted at the end point 157d.2 of the helical dose track. However, as the dimple is smaller than the extension of the helical surface portion 189d, it will not influence the helical movement of the front edge 189d.1. The same effects are obtained by the angularly shifted surface portion 182c and distal helical surface portion 189c.

Cross Sections of Injection Device in Initiated State

FIGS. 14A and 14B illustrate cross sections of the injection device 100. FIG. 14A corresponds to FIG. 12A and illustrates a central cross section comprising the windows 141. FIG. 14B illustrates a central cross section of the device after a 90 degrees rotation relative to the view of FIG. 14A. The drive tube 180 comprises 4 tubular portions, as indicated on FIG. 12B.

FIG. 14 illustrates the device 100 in an initiated state, wherein the shield has been rotated to initiate the device. The shield has moved proximally in a helical movement together with the needle assembly 120. The proximal movement of the shield has induced a proximal movement of the needle hub 125, whereby the needle 124 has established fluid connection with the reservoir in the cartridge 135. The cartridge 135 and the plunger 136 has also been moved in the proximal direction, and due to the abutment with the washer 104, the plunger has been stopped in the proximal movement, whereby the chamber of the cleaning assembly 120 has been filled (washer 104 is shown in FIG. 6, but not in FIG. 14).

Operation of the Device

FIG. 15 is used to describe the working principles of an embodiment of the disclosure from a user perspective, and a more detailed description of the working principle will be described later and with reference to FIG. 16. FIG. 15A shows the user operations of the injection device 100, for taking a first dose, and FIG. 15B shows the operations, for taking a subsequent dose, wherein the subsequent dose can be any of the fixed doses in the sequence between the first and the last dose of the plurality of fixed doses. The injection device can be stored and delivered in a secondary packaging, and in the out-of-pack state (A1) the injection device has been unpacked from the secondary packaging.

As illustrated in FIG. 15A, when the user desires to take a first fixed dose, the injection device is unpacked and thereby provided in the out-of-pack state (A1). Thereafter the injection device is initiated by the user. Initiation can be done by grapping a main portion 102 of the device with the right hand and the cap 105 with the left hand. Hereafter, the user turns the cap in the counterclockwise direction (for the illustrated example). Hereby, the cap snaps off the cap snap 161.1 of the housing assembly and engages the needle shield, whereby the needle shield follows the rotation of the cap 105 until the cap 105 has been turned to the rotational stop 161.4. Due to the step-wise helical guide 112 of the shield and the proximal guide 162 of the housing assembly, the needle shield is subject to a combined proximal and rotational movement, in response to the user turning the cap. Furthermore, by this initial rotation of the cap and the combined rotational and proximal movement of the needle shield, the needle cannula 124 pierces the septum of the cartridge 135, and thereby establishes fluid communication with a drug reservoir in the cartridge 135. Furthermore, in this operation the cartridge 135 is proximally displaced and pushed against the piston rod 109 or the piston washer 104. As the cannula has established fluid connection, and as the piston is arranged in abutment with the piston rod, the integrated needle is primed, as will be explained in detail later. As the cap reaches the rotational stop, the injection device is positioned in the cap unlocked and initiated state (B1), wherein the cap is unlocked and positioned to be taken off. The initiated state is also shown in cross section in FIG. 15.

In the following step the user pulls the cap 105 of, whereby the injection device is arranged in the cap-off state (C1), and wherein the shield is locked against axial translation.

Hereafter, the user manually turns the shield in the counterclockwise direction, whereby the device is arranged in a shield unlocked state (D1), the shield is arranged in an unlocked position and can be pressed proximally into the housing. Due to the guides between the shield and the housing 112, 162, the shield is subject to a combined proximal and rotational movement when operated between the cap-of state and the shield unlocked state. During the rotational unlocking movement of the needle shield, the needle shield uncovers the cartridge inspection window 141 in the housing, whereby the drug in the cartridge can be inspected. In addition, the piston 136 is also visible in the inspection window 141, and the position of the piston 136 relative to a fixed dose scale on the housing indicates the progression of the piston during use, and thereby indicates the remaining number of fixed doses in the reservoir. In FIG. 15A, in the shield unlocked state (D1), the piston 136 is arranged in the initial position and 4 doses are remaining in the reservoir. During the proximal movement of the needle shield, the distal end of the needle tip protrudes through the septum at the distal end of the cleaning assembly 120, whereby any excess pressure in the needle is released.

Hereafter, the user presses the needle shield against the injection site, whereby the shield and the connector 170 is proximally displaced against the force of the shield return spring 107. Hereby, the needle is inserted into the skin or subcutaneous layer of a patient. By this operation, the axial movement of the shield triggers the drive mechanism, and a fixed dose is delivered through the needle cannula in a dosing state (E1). At the end of dose, the piston 136 has moved to the next position, which is indicated by the fixed dose residual scale on the housing, and the injection device can be removed from the injection site. The cut-out window of the residual scale shows the piston in the next position. As the piston 136 progresses under the dosing state it can be useful to define to substates for a respective dosing state: an initial dosing state (E2.1) and a final dosing state (E2.2), wherein the piston is in a pressurized proximal position and a relaxes distal position, respectively.

After the dose has been completed, the user removes the device from the skin, and the pressure is thereby released from the shield. Consequently, the shield moves in the distal direction due to the action of a return spring 107. Due to guides 112, 162 between the shield and the housing, and guides 114, 142 between the shield and the connector 170, the shield is subject to a distal movement followed by a combined distal and rotational movement, whereby the shield automatically returns to a relocked state (F1).

Hereafter, the user puts on the cap 105 by an axial movement to put the device in a capon state (G1), which is the last state shown in the sequence shown in FIG. 15A. The cap unlocked state and the cap on state, within the same sequence, differs technically in that the cartridge comprises a dose less in the cap on state.

Finally, the cap is turned, and thereby snap locked to the housing assembly to enter a cap locked state (A2), which is illustrated in FIG. 15B.

The cap locked state (A2) differs from the out-of-box state (A1) in that the device has been initiated. This is illustrated in FIGS. 15A and 15B, as the shield in state (A2) is proximally and rotationally shifted in comparison with the position of the shield in state (A1). Furthermore, in state (A2) the cartridge contains a dosage less than in state (A1).

As the user turns the cap to take a subsequent dose, the cap is turned to the cap unlocked position without rotating the shield, as the shield is already turned to the initiated but axially locked position. The cap unlocked state (B2) differs from the cap unlocked state (B1) in that in state (B2) the cartridge contains a dosage less than in state (B1), and a corresponding difference can be observed between C1-C2, D1-D2 . . . G1-G2, A2-A3, B2-B3 . . . and so forth. This pattern of operation can be continued until the final dose has been delivered, wherein it will not be possible to trigger the drive mechanism again.

Detailed Description of the Operation of the Device

Figure 16A:
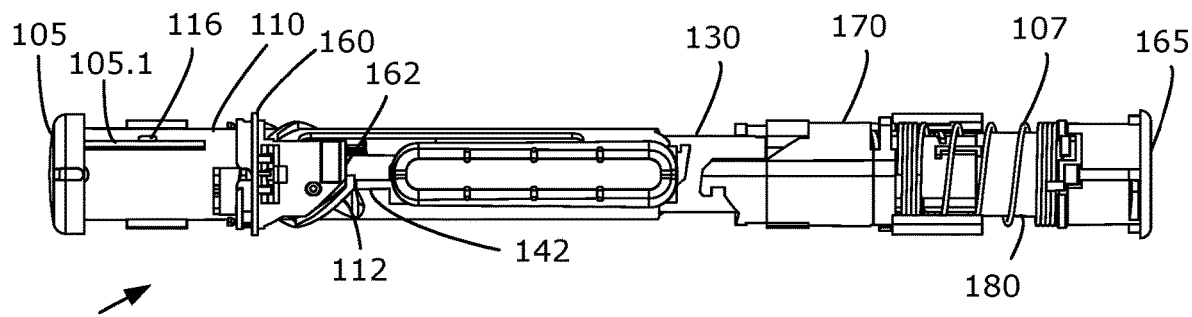
FIGS. 16A-16T show the injection device of FIG. 1A in different states and intermediate arrangement, and thereby provide a detailed illustration of the operation of the device.
Figure 16B:
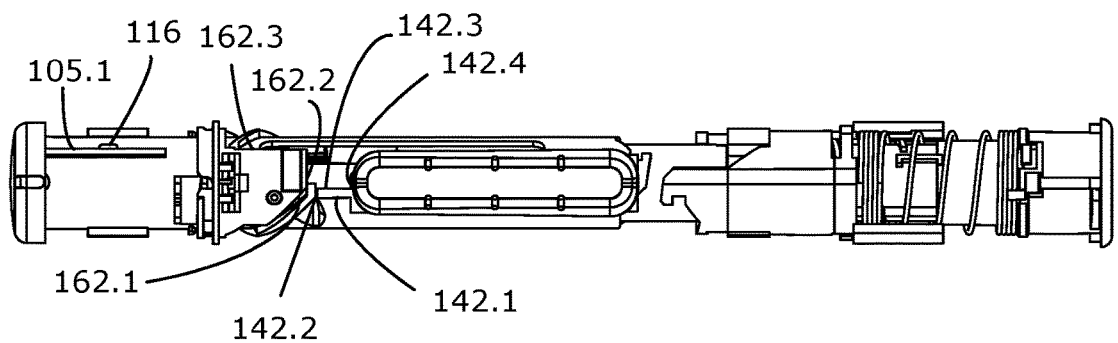
Figure 16C:
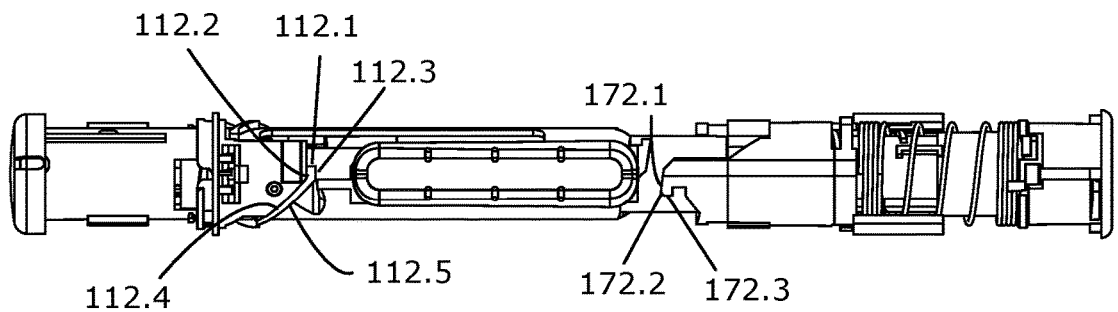
Figure 16D:
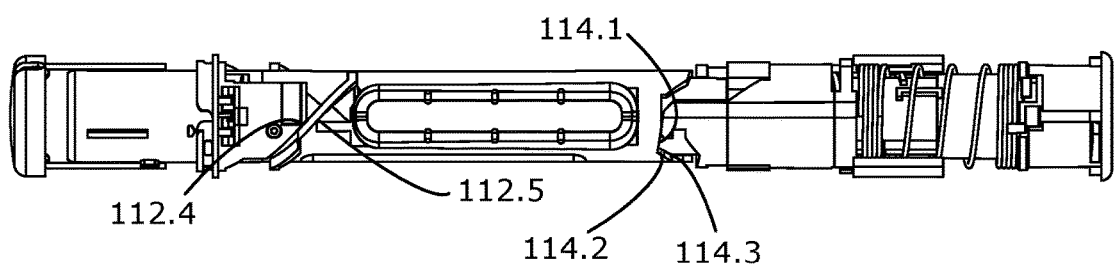
Figure 16E:
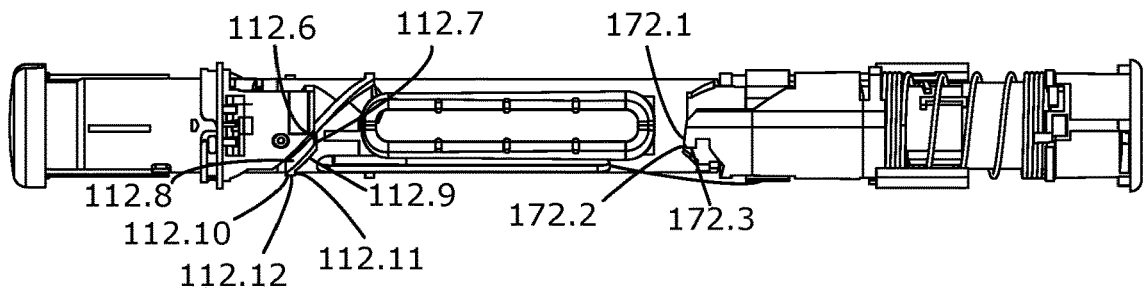
Figure 16F:
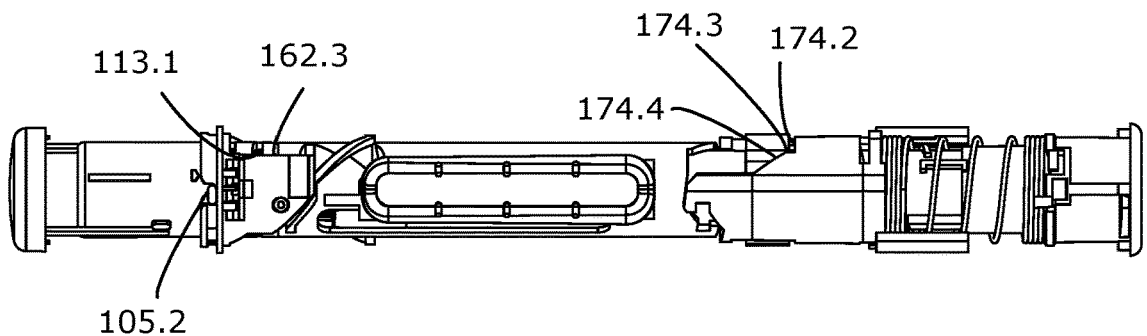
Figure 16G:
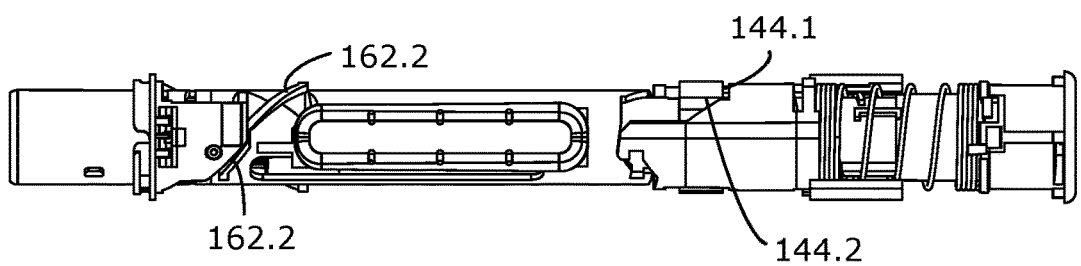
Figure 16H:
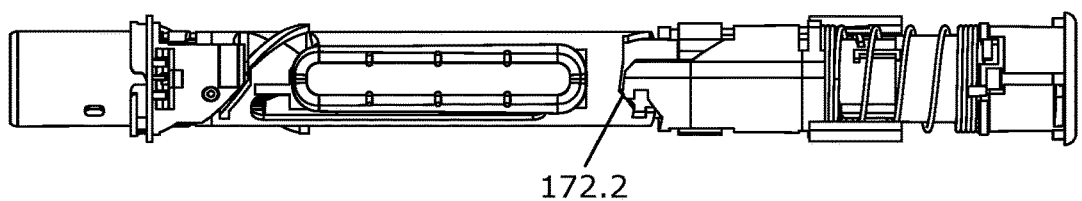
Figure 16Q:
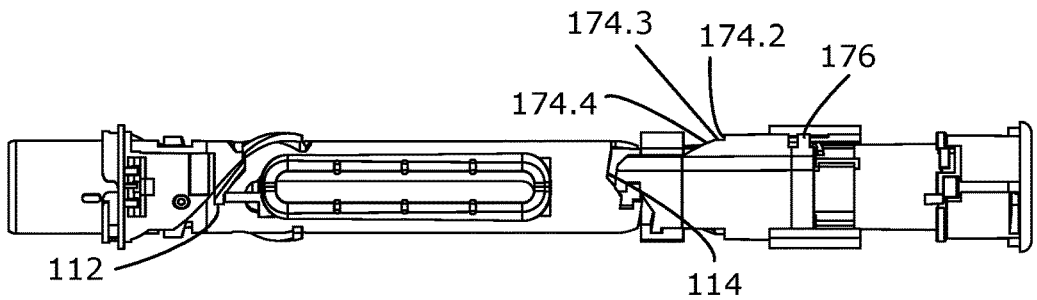
Figure 16R:
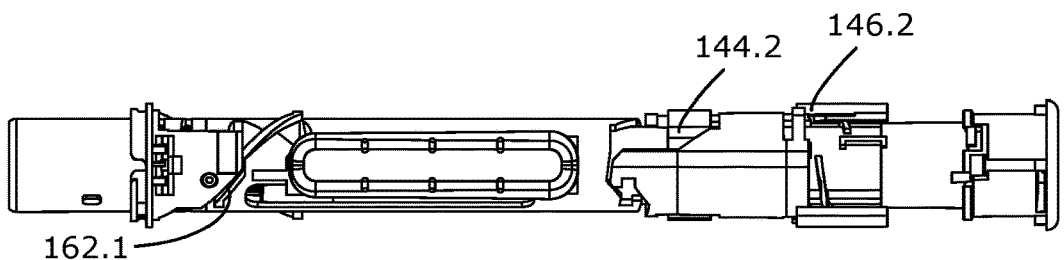
Figure 16S:
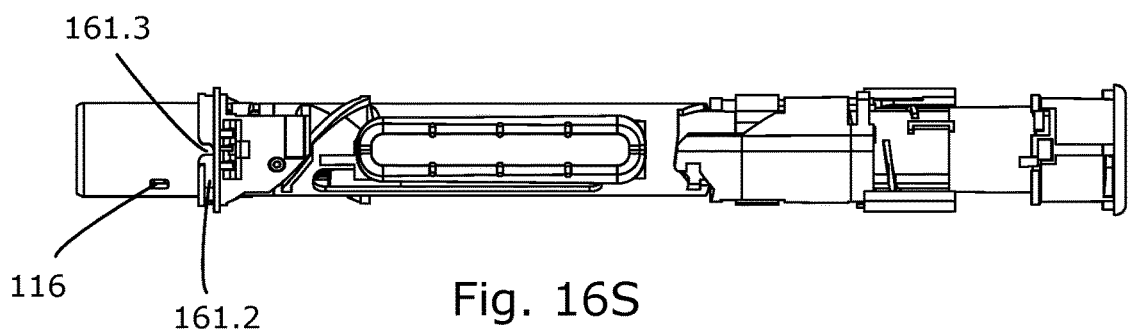
Figure 16T:
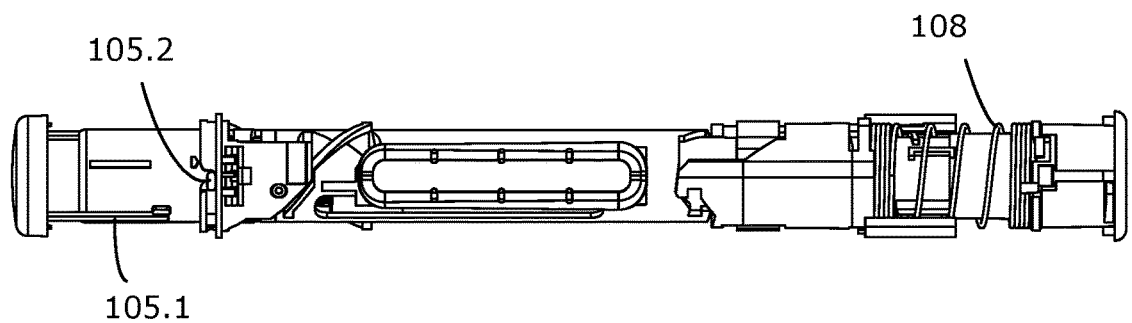

FIG. 16A to 16T collectively illustrate the relative and functional arrangement of the different structures during the sequence of states of the injection device 100, and thereby illustrate the operation of the device in details.

In an embodiment of the present disclosure, the injection device 100 for sequentially delivering a plurality of fixed dosses comprises: a housing comprising an elongate housing structure 140, a cartridge holder 130, and a housing insert portion 160, an internal thread, a shield comprising the elongate shield structure 110 and the needle tip 119, a needle hub 125 comprising the fixedly attached needle cannula 104, a cap 105 removably mounted on the housing and adapted for covering a distal end of the shield, a cartridge 135 with a movably arranged cartridge plunger 136 and a drive mechanism comprising a torsional drive spring 108, a drive tube 180 and a piston rod 109 with an outer thread for cooperating with the internal thread of the housing, the piston rod is arranged in connection with the plunger 136, and wherein the torsional spring is adapted to provide a torque for rotating the drive tube 180 relative to the housing. The drive tube comprises a ratchet mechanism ensuring rotation in a dosing direction and blocking in a non-dosing direction. The drive tube is axially splined with the piston rod, whereby relative axial movement is allowed, and relative rotation is prevented. The drive tube is adapted to advance the piston rod, in response to rotating the drive tube in the dosing direction, and due to the threaded connection with the housing, the piston rod is adapted to advance the plunger 136 in the cartridge 135 to expel a fixed dose. The drive mechanism is adapted to be activated, by changing the drive tube from a distal position, wherein the drive mechanism is in a stationary mode, to a proximal position, wherein the drive mechanism is in a dosing mode. In the distal position, the drive tube is rotationally locked to the housing. In the proximal position, the drive tube is rotationally unlocked from the housing, and the provided torque can rotate the drive tube a predetermined angel to expel the fixed dose. In the stationary mode of the drive mechanism, the piston rod is rotationally and axially locked, and the piston rod is rotationally locked to the housing through the splined connection with the drive tube 180, and axially locked through the threaded connection with the housing.

The torsion spring is pre-strained to deliver the plurality of doses without restraining during use. The drive mechanism is adapted to change mode upon activation, and as explained later the drive mechanism is adapted to be repeatably activated until the last dose has been expelled.

The cap can be arranged in an axially locked position and an axially unlocked position. The cap can be changed between the positions by turning the cap relative to the housing. For the cap being in the axially unlocked position, the cap can be removed from the housing.

The needle hub 125 is movably arranged on the housing and can be moved between the distal position and the proximal position relative to the housing. The needle hub 125 is arranged in connection with the cartridge and is rotationally locked relative to the housing. For the needle hub being in the distal position the proximal end of the needle cannula is arranged distally to a pierceable septum of the cartridge. For the needle hub 125, being in the proximal position, the needle cannula extends through the septum and is positioned in fluid communication with the reservoir of the cartridge. I response to moving the needle hub from the distal to the proximal position, the needle cannula pierces the septum of the cartridge, and moves the cartridge a proximal distance relative to the housing and the axially locked piston rod.

The shield can be arranged in different positions. An initial position defined by an initial angular position and a corresponding initial axial position. A locked position defined by a locked angular position and a corresponding locked axial position. An unlocked distal position defined by an unlocked angular position and a corresponding distal unlocked axial position. An unlocked proximal position defined by the unlocked angular position and a corresponding proximal unlocked axial position. In the initial position, the shield is adapted to prevent an axial and clockwise movement, and adapted to allow a counterclockwise movement. In the locked position, the shield is adapted to prevent clockwise and axial movement. In this position, the shield is further adapted to allow a counterclockwise rotation. In the unlocked distal position, the shield is adapted to prevent counterclockwise and distal movement of the shield, and further adapted to allow proximal movement. In the unlocked distal position, the shield is further adapted to allow a clockwise rotation, if the applied torque exceeds a predefined threshold. For the shield being in the initial position and the locked position the needle tip is covered by the shield. In the unlocked position, the shield is adapted to be moved from the unlocked distal position, wherein the needle tip is uncovered by the shield and wherein pressure in the reservoir can be released, and proximally to the unlocked proximal position, wherein the needle tip extends further from the shield and can be inserted into the subcutaneous layer of a subject. The shield can be manually operated between the different positions by the user. As appears for the shield being in the initial position, the locked position, the distal unlocked position and the proximal unlocked position, defines four different sets of angular and axial positions: three different angular position and four different axial positions.

The connector can be arranged in an initial position initial position defined by an initial angular and initial axial position, wherein it is positioned rotationally locked to the middle guide 144 of the housing, wherein the middle guide 144 also prevents a distal movement of the connector. The connector is biased in the distal direction by return spring 107.

FIG. 16A to 16T collectively illustrate the injection device 100 arranged in different states and intermediate arrangements, wherein an outer portion of the housing and an outer portion of the cap has been cut away to illustrate some of the internal structures.

FIG. 16A illustrates the injection device in the out-of-pack state, and shows the cap 105, the shield structure 110 the housing insertion portion 160, the cartridge holder 130, the connector 170, the drive tube 180 and the return spring 107, and the spring base 165. In FIG. 16A reference numbers are also provided for the proximal guide 162 of the housing insert portion, the stepwise helical guide 112 of the shield and the distal guide 142 of the housing. The user receives the device from the pharmacy and unpacks the device from the secondary packaging. By unpacking the user has provided the injection device in the out-of-pack state.

FIG. 16B to 16E collectively illustrate the intermediate arrangements between the out-of-pack illustrated in FIG. 16A, and the cap unlocked state, illustrated in FIG. 16F. In FIG. 16B reference numbers are shown for details of the proximal guide 162 and the distal guide 142. The details are: the helical portion 162.1, the transverse portion 162.2, the axial portion 162.3, the first axial portion 142.1, the first transverse portion 142.2, the second axial portion 142.3 and the second transverse portion 142.4. Reference numbers for details of the stepwise helical guide 112 are shown in FIGS. 16C and 16E. The details are: the proximal axial guide portion 112.1, the first proximal transverse guide portion 112.2, the second proximal transverse guide portion 112.3, the first proximal helical guide portion 112.4, the second proximal helical guide portion 112.5, the first middle transverse guide portion 112.6, the second middle transverse guide portion 112.7, a first distal helical guide portion 112.8, the second distal helical guide portion 112.9, the first distal transverse guide portion 112.10, the second distal transverse guide portion 112.11 and the distal axial guide portion 112.12. Reference numbers for details of the proximal guide 114 of the shield are shown in FIG. 16DC. The details are: the first left-handed helical portion 114.1, the first right-handed helical portion 114.2, the second right-handed helical portion 114.3. Reference numbers for details of the distal guide 172 of the connector is shown in FIG. 16C. The details are: the left-handed helical portion 172.1, the right-handed helical portion 172.2, the first axial portion 172.3.

Out-of-Pack State

The first user operation is to turn the cap counterclockwise until it reaches the cap axially unlocked position, whereby the shield is changed from the initial position to the locked position, and whereby the device is changed from the out-of-pack state through a number of intermediate arrangements to the cap unlocked state, also referred to as the shield initiated state.

In more details, FIG. 16A illustrates the arrangement of the injection device provided in the out-of-pack state. The cap 105 is arranged in the axially locked position, and the shield is arranged in the initial position. A small circumferential clearance is provided between the axially extending rib 116 protruding from the inner surface of the cap and the axially extending rib 105.1 protruding from the outer surface of the shield. The protrusion on the inner surface of the cap 105.2, is releasably retained in the cap mount track 161 by the snap lock 161.1.

FIG. 16B illustrates a first intermediate arrangement of the injection device. The circumferential clearance has been eliminated by the rotation, and an abutment has been provided between the axially extending rib 116 of the cap and the axially extending rib 105.1 of the shield. By further rotation, a torque will be transferred from the cap to the shield. In the first intermediate arrangement a circumferential clearance is provided between the first proximal helical guide 112.4 of the shield and the helical portion 162.1 of the housing insert portion, allowing a relative counterclockwise rotation between shield and housing. Furthermore, only a small axial clearance is provided between the first proximal transverse guide portion 112.2 of the shield and the transverse portion 162.2 of the housing, preventing distal movement of the shield which exceeds the axial clearance. Similarly, only a small axial clearance is provided between the second proximal transverse guide portion 112.3 of the shield and the first transverse portion 142.2 of the housing, preventing a proximal movement, which exceeds the axial clearance.

In a second intermediate arrangement of the injection device illustrated in FIG. 16C, the circumferential clearance between the step wise helical guide 112 and the proximal guide 162 of the housing has been eliminated to provide abutment between the first proximal helical guide 112.4 of the shield and the helical portion 162.1 of the housing. In this position is further provided a circumferential clearance between the second proximal transverse guide portion 112.3 of the shield and the first transverse portion 142.2 of the housing, whereby the transverse portion 142.2 does not block against axial movement.

In a third intermediate arrangement of the injection device illustrated in FIG. 16D, the shield has been further rotated. In response to a rotation, the abutment between helical guide portions of the shield and the housing provides a combined rotational and proximal movement relative to the housing. Therefore, the step-wise helical guide 112 has been moved proximally along the helical guide portion 162.1. The stepwise helical guide portion comprises a front edge and a trailing edge defined according to the direction of the relative movement between shield and housing. Due to the relative movement, the area of the abutment becomes progressively smaller until the trailing edge of the first proximal helical guide portion 112.4 reaches the proximal edge of the helical portion 162.1. At this position of minimum abutment, the abutment between the step-wise helical guide and the housing is shifted from abutment between helical portions to abutment between transverse portions, whereby the shield is guided in a pure rotation, in response to further counterclockwise rotation. In FIG. 16D the abutment between the first proximal helical guide portion 112.4 of the shield and the helical portion 162.1 of the housing is provided between a distal portion of the first proximal helical guide portion 112.4 (close to the trailing edge) and the trailing edge. Furthermore, as illustrated in FIG. 16D, the connector is arranged in the initial angular and axial position, wherein it is rotationally locked to the housing, and prevented from distal movement, the connector is biased in the distal direction by the return spring 107. Due to the proximal helical movement of the shield an abutment in a rest position has been established between the first left-handed helical portion 114.1 of the proximal guide of the shield and the left-handed helical portion 172.1 of the connector. In this position of the shield, a small axial clearance is provided between the second proximal helical guide portion 112.5 and the the first transverse portion 142.2, whereby pure axial movement in the proximal direction exceeding the clearance is prevented.

In a fourth intermediate arrangement of the injection device illustrated in FIG. 16E, the shield has been further rotated. The abutment between the transverse portions of the stepwise helical guide 112 and the housing, provides a pure rotation. Therefore, the step-wise helical guide 112 has been moved in the counterclockwise direction along the transverse portion 162.2. The transverse guide portion 162.1 defines a first and a second edge, wherein the second edge is position counterclockwise to the first edge. The first middle transverse portion 112.6 comprises a front and a trailing edge defined according to the direction of the relative movement between shield and housing. Due to the relative movement, the area of the abutment becomes progressively smaller until the trailing edge of the first middle transverse guide portion 112.6 reaches the second edge of the transverse portion 162.2. At this position of minimal abutment, the abutment between the step-wise helical guide and the housing is shifted from abutment between transverse portions to abutment between helical portions, whereby the shield is guided in a helical movement, in response to further counterclockwise rotation. In FIG. 16E the abutment between the first middle transverse guide portion 112.6 of the shield and the transverse portion 162.2 of the housing is provided between the middle of the guide portion and the trailing edge. In the illustrated arrangement, a small axial clearance is provided between the second middle transverse guide portion 112.7 and the first transverse portion 142.2 of the housing, whereby proximal movement is limited.

Cap Unlocked, Shield Initiated and Locked State

In the cap unlocked and shield locked state, as illustrated in FIG. 16F, the cap 105 is arranged in the axially unlocked position, and the shield is arranged in the locked position.

The cap is positioned with the protrusion 105.2 on the inner surface of the cap at the second end of the circumferential track portion 161.3, whereby the protrusion 105.1 is angularly aligned with the axial track portion 161.2, and can be moved in the distal direction. The shield is arranged in the locked position, wherein abutment is established between the step-wise helical guide 112 and both the transverse portion 162.2 and the helical portion 162.1. In addition to the abutment between the first left-handed helical portion 114.1 of the proximal guide of the shield and the first left-handed helical portion 172.1 of the connector, an additional abutment has been provided between the first right-handed helical portion 114.2 and the right-handed helical portion 172.2. Due to the proximal movement of the shield the connector has been moved proximally relative to the initial axial position and against the biasing force of the spring 107. The connector is still rotationally locked. To prevent clockwise rotation towards the out-of-pack state, the axial surface portion 113.1 of the click-arm abuts the axial portion 162.3 of the housing. The click 113 has deflected in a radial direction from a compressed state behind the housing insert portion 162.

Cap-Off State

The second user operation is to pull the cap in a distal direction, whereby the device is changed from the cap unlocked state to the cap-off state.

In the cap of state, as illustrated in FIG. 16G, the cap has been removed from the main portion 102 of the injection device shown in FIG. 16F. The position of the shield is unchanged in relation to the arrangement in FIG. 16F, and is still in the locked position. The shield is axially locked, but allowed to perform a proximal helical movement guided by the abutment between the step-wise helical guide 112 and the helical portion 162.1 of the housing.

Shield Unlocked State

The third user operation is to turn the shield, being in the locked position, in the counterclockwise direction until it reaches the unlocked position, and whereby the device has been changed from the cap-off state through a number of intermediate arrangements to the shield unlocked state.

FIG. 16H illustrates the first intermediate arrangement, wherein the shield has been rotated. In response to the rotation, the abutment between the helical guide portions of the shield and the housing provides a combined rotational and proximal movement relative to the housing. Therefore, the step-wise helical guide 112 has been moved proximally along the helical guide portion 162.1. The step-wise helical guide portion comprises a front edge and a trailing edge defined according to the direction of the relative movement between shield and housing. Due to the relative movement, the area of the abutment becomes progressively smaller until the trailing edge of the first distal helical guide portion 112.8 reaches the proximal edge of the helical portion 162.1. At this position of minimum abutment, the abutment between the step-wise helical guide and the housing is shifted from abutment between helical portions to abutment between transverse portions, whereby the shield is guided in a pure rotation, in response to further counterclockwise rotation. In FIG. 16H the abutment between the first distal helical guide portion 112.8 of the shield and the helical portion 162.1 of the housing is provided between a proximal portion of the first distal helical guide portion 112.8 (close to the front edge), and the trailing edge. Furthermore, in the position of the shield illustrated on FIG. 16H, abutment has been established between the first left-handed helical portion 114.1 of the proximal guide of the shield and the first left-handed helical portion 172.1 of the connector. In this position of the shield, a small axial clearance is provided between the second proximal helical guide portion 112.5 and the the first transverse portion 142.2, whereby pure axial movement in the proximal direction exceeding the clearance is prevented. Due to the proximal helical movement of the shield, the connector in abutment with the shield has been moved further in the proximal direction. Due to the rotational movement of the shield and the connector being rotationally locked by the middle guide 144 of the housing, the shield 110 rotates relative to the connector 170 whereby the right-handed helical portion 172.2 slides along the first right-handed helical portion 114.2, and whereby the first left-handed helical portion 172.1 is brought out of abutment with the first left-handed helical portion 114.1 of the proximal guide of the shield.

From the first intermediate arrangement shown in FIG. 16H to the shield unlocked position shown in FIG. 16K1, the shield rotates in a proximal helical movement guided by the first distal helical portion 112.8 followed by a pure rotational movement guided by the first transverse portion 112.10. The arrangement for guiding pure rotational movement is illustrated in FIG. 16J. By the proximal rotational movement of the shield 110 relative the housing 140, the shield 110 is moved relative to the connector 170, and the shield moves the connector relative to the housing. The right-handed helical portion 172.2 slides from the first right-handed helical portion 114.2 (FIG. 16H) along the second right-handed helical portion, until the trailing edge of the helical portion 172.2 reaches the proximal edge of the second right-handed helical portion (FIG. 16J). As the trailing edge is passed, a new abutment is established between the second left-handed helical portion 114.4 and the left-handed helical portion 172.1 of the connector, as the locking structure 171 of the distal guide of the connector moves into engagement with the locking structure 115 of the proximal guide of the shield (FIG. 16K1). As the left-handed helical portions 114.4, 172.1 of the locking structures 115, 171 are in abutment under the biasing force of the return spring 107, the shield is urged in the counterclockwise direction, whereby the distal axial guide portion 112.12 is brought in contact with the third axial portion 142.5 of the housing and rotationally stopped. Due to the biasing force and the helical engagement, a releasable locking mechanism is provided. To release the lock, a torque exceeding a release threshold torque is required. As earlier mentioned the connector 170, has contemporaneously moved relative to the housing. The connector 170 has been pushed out of the rotational lock with the middle guide 144 of the housing (FIG. 16H). Hereby has a trailing edge of the second axial guide portion 174.3, passed the distal edge of the first axial portion 144.2 of the middle guide, whereby the first axial portion 144.2 has shifted from abutment with the second axial guide portion 174.3 to abutment with the left-handed helical portion 174.4. The connector 170 is guided along the left-handed helical guide portion 174.4 until the click arm 176 of the connectors abuts, the first axial portion 146.1 of the proximal guide of the housing, as shown in FIG. 16K1. 16K2 illustrates the connector's 170 relative arrangement to the drive tube 180, wherein an angular portion of the connector has been removed. The remaining portion comprises the activation tab. The position of the activation tab 178 is indicated by the transverse portion 178.1 and the axial portion 178.2. As shown, the transverse portion 178.1 is in abutment with the transverse portion 183.1 of the protruding tab 183 of the drive tube. Thereby, the connector 170 is arranged in a position for transferring a force and a proximal movement to the drive tube. FIGS. 16K3 and K4 shows the arrangement of FIG. K2, from the opposite side (180 degrees rotation about the central axial axis). As also shown in FIG. 16K3, in arranging the shield in the shield locked state, the connector has translated the drive tube a small distance in the proximal direction relative to the initial position of the drive tube, whereby proximal helical surface portion 157 is revealed (see FIG. 16K3).The initial position of the drive tube 180 is shown in FIG. 13A. FIG. 16K4 illustrates the injection device in grey scale to provide a better impression of the orientation of the surfaces and the extension of the different structures.

Dosing State

The fourth user operation is to push the shield, being in the unlocked distal position, in a proximal direction until it reaches the unlocked proximal position, and whereby the device has been changed from the shield unlocked state through a number of intermediate arrangements to the dosing state.

From the shield unlocked state shown in FIG. 16K1 to the first arrangement of the injection device in the dosing state shown in FIG. 16L1, the shield has been pushed in the axial direction from the unlocked distal position to the unlocked proximal position, whereby the activation tab 178 has been pushed though the transverse opening in the outer helical structure 184. By the proximal movement of the shield, the shield has moved the interlocked connector 170. The connector abutting the drive tube 180, has moved the drive tube 180 from a distal stationary position, wherein the drive tube is rotationally locked by the housing, to a proximal rotational position, wherein the drive tube will rotate relative to the housing. By the proximal movement the torsionally strained drive spring 109 has been compressed and brought into a compressed state. From the first arrangement of the device in the dosing state (FIG. 16L1) to the last illustrated arrangement in the dosing state (FIG. 16N1), the drive tube has turned 360 degrees during a distal helical movement, i.e., a full rotation, and returned to the initial position in the housing (FIGS. 13A and 13N3), wherein the drive tube is rotationally locked to the housing, and whereby a fixed dose has been expelled. By the rotational movement of the drive tube, the drive tube with the front edge of the distal helical surface portion 189 has traveled from a start dosing position illustrated in FIG. 16L3, in the counterclockwise direction along the proximal helical surface portion 157 of the inner tubular portion 154 of the housing, to an intermediate shield unlocking position illustrated in FIG. 16M3 and 16M4, wherein the axial portion 183.2 hits and abuts the axial portion 178.2 of the tab 178, as indicated on FIG. 16M2. The drive tube with the front edge of the distal helical surface portion 189 continues the distal helical movement along surface portion 157, until it reaches the axial surface portion 156 of the inner tubular portion 154 of the housing. The drive spring is rotated by the torsionally pre-strained drive spring 108, and the helical surface portion of the drive tube is kept in contact with the helical surface portion 157 of the housing, as the compressed drive spring 108 expands during unwinding. Hereby, the drive tube has returned to the initial position, which corresponds to that the drive tube has reached a stop dosing position, and further counterclockwise rotation has been prevented, as illustrated in FIGS. 13A and N3. In this position the activation tab 178 can be moved proximally through the transverse opening in the outer helical structure 184, in response to the release of the axial and proximally oriented force on the shield, i.e, the pressure on the shield tip 119 is released as the device is lifted from the skin. As appears for the drive tube being in the start dosing position, the intermediate shield unlocking position and the stop dosing position, defines three different sets of angular and axial positions: three different angular coordinates and three different axial coordinates.

Initialization of Automatic Relock Mechanism

During the rotation of the drive tube 189 from the intermediate shield unlocking position to the stop dosing position the drive tube has provided a torque to the connector, which exceeds the release threshold torque. Hereby, the locking structure 171 of the connector has been released from the locking structure 115 of the shield, and the connector has been rotated until abutment with a rotational stop provided in the housing. By releasing the locking structures from each other the automatic shield relocking mechanism has been initiated.

During the counterclockwise rotation, a trailing edge of the left-handed helical portion 172.1 moves slightly in the proximal direction along the second left-handed helical portion until a proximal edge of the second left-handed helical portion 114.1 has been exceeded. Thereby, the connector has shifted from abutment with the left-handed helical portion 114.4 of the shield to abutment with the right-handed helical portion 114.3 of the shield, i.e., the abutment between the right-handed helical portion 172.2 of the connector and the second right-handed helical portion 114.3 of the shield has been reestablished. Due to the right-handed helical abutment, the connector is urged in the counterclockwise direction under the distally oriented biasing force of the return spring 107. However, during the rotation of the connector, the connector arm 176 rotates along the first transverse portion 146.2 of the proximal guide of the housing and until an angular position of abutment between the axial surface 176.1 of the connector arm and second axial portion 143.3 of the proximal guide of the housing. Optionally and additional abutment is provided between the third axial portion 174.5 of the middle guide of the connector the first axial portion 144.2 of the middle guide of the housing. Hereby, further counterclockwise rotation of the connector 170 is prevented. As the shield 110, in this unlocked proximal position, is prevented from clockwise rotation due to the abutment between the distal axial guide portion 112.12 of the step-wise helical guide of the shield and the second axial portion 142.3 of the distal guide of the housing, and possibly also due to an optional abutment between the third axial portion 114.8 of the proximal guide of the shield and the second axial portion 144.4 of the middle guide of the housing, the connector can only move the shield in the axial direction in a pure axial movement.

Split-Dose-Prevention

During activation of the drive tube 180, the connector has been moved in a pure proximal axial direction, until the activation tab 178 has reached the position indicated with the patterned rectangle in FIG. 16L3. As previously described, by this movement of the connector, the drive tube 180 is consequently moved between the distal stationary position, wherein the drive tube is rotationally locked by the housing, to the proximal rotational position, wherein the drive tube will rotate relative to the housing due to the torsion provided by the drive spring 108. By this axial movement the activation tab has been moved through the transverse opening in the helical structure 184, and as the drive tube reaches the proximal rotational position the drive tube starts to rotate, and the outer helical structure 184 protruding from the outer surface of the drive tube rotates into a transverse overlap with the activation tab 178, whereby the activation tab and the connector is retained in a position proximal to the helical structure 184. During the rotational movement of the connector from the start dosing position, as seen in FIG. 16L3 to the stop dosing position seen in FIG. 16N3, the activation tab 178 is retained on the proximal side of the helical structure 184 of the drive tube, whereby a split-dose has been prevented. If the pressure is released premature, i.e., before the stop dosing position is reached, the connector and the shield is moved in the distal direction until axial abutment between the distally oriented retention portion 178.3 of the activation tab 178 and the helical structure 184. Hereafter, if the axial proximal force on the shield is not reestablished, the activation tab will slide along the helical structure 184 as the drive tube rotates to the stop dosing position, whereby the activation tab will be moved in a pure distal axial direction through the transverse opening in the helical structure 184.

FIG. 16M1-M3 illustrate the same arrangement of the injection device 100. FIG. 16M2 illustrates the device from the same angle as in FIG. 16M1, but an angular portion of the connector has been cut away. FIGS. 16M2 and M3 are seen from opposite sites (180 degrees rotation about the central axial axis). FIG. 16M4 illustrates the arrangement of FIG. 16M3 in gray scale.

FIG. 16N1-N3 illustrate the same arrangement of the injection device 100. FIG. 16N2 illustrates the device from the same angle as in FIG. 16N1, but an angular portion of the connector has been cut away. FIGS. 16N2 and N3 are seen from opposite sites (180 degrees rotation about the central axial axis).

Relocked State

The fifth user operation is to release the axially oriented force on the shield, by lifting the needle tip 119 from the skin, whereby the shield being in the unlocked proximal position, is moved in the distal direction until it reaches the locked position, and whereby the device has been changed from the dosing state through a number of intermediate arrangements to the relocked state.

From the last arrangement in the dosing state shown in FIG. 16N1 to the intermediate arrangement shown in FIG. 16P, the shield 110 has been moved by the connector 170 in the axial direction from the unlocked proximal position to the unlocked distal position, whereby the activation tab 178 has been moved though the transverse opening in the outer helical structure 184. From the intermediate arrangement shown in FIG. 16P to the intermediate arrangement shown in FIG. 16Q the connector has rotated the shield in the clockwise direction. From the intermediate arrangement shown in FIG. 16Q to the relocked state shown in FIG. 16S, the shield has been moved by the connector 170 in the distal direction during clockwise rotation.

During the distal movement the right-handed helical portion 172.2 of the connector abuts the second right-handed helical portion 114.2 of the shield. Due to the helical abutment between connector and shield the shield is urged in the clockwise direction, whereby the distal axial portion 112.12 is urged towards the second axial portion 142.3 of the housing. Therefore, the shield is axially guided along the distal guide of the housing until a trailing edge of the helical portion 172.2 has reached a distal edge of the second axial portion 142.2, whereby the shield can rotate in the clockwise direction, in response to further distal movement, as illustrated in the intermediate arrangement shown in FIG. 16P. During the clockwise rotation, illustrated by the intermediate arrangements shown in FIGS. 16P to 16Q, the step-wise helical guide 112 slides between first transverse portion 142.2 and the transverse portion 162.2, while the connector biases the shield 110 and slides along the proximal guide 114 of the shield. As a trailing edge of the first distal transverse guide portion 112.10 reaches the edge between the transverse portion 162.2 and the helical portion 162.1 (FIG. 16Q), the shield can move in a combined distal and rotational movement guided by the connector moving along the second-right handed helical portion 114.3 to the rest position in abutment with the first left-handed helical portion 114.1 of the proximal guide (FIG. 16S).

During the distal movement of the shield, the connector 170 has moved in the distal direction guided by the first axial portion 144.2 of the middle guide of the housing preventing counterclockwise rotation, as illustrated in the last arrangement in the dosing state (FIG. 16N1) and the intermediate arrangements in FIGS. 16P and 16Q. As the front edge of the left-handed helical portion 174.4 reaches the proximal edge of the first axial portion 144.2, a clockwise rotation of the connector is initiated. During the distal movement, the connector arm or click arm 176 has traveled along the axial guide portions 146.3 and 146.4 and along the ramp portion 146.4 to the flush surface portion 146.5, whereby the click arm 176 has been radially compressed, as indicated in FIG. 16Q. As the connector 170 is moved further in the distal direction, the left-handed helical portion 174.4 slides along the middle guide 144 of the housing, which induces a clockwise rotation until the trailing edge of the helical portion 174.4 reaches the proximal edge of the first axial portion 144.2. At this position connector has almost reached the rest position with the proximal guide of the shield, wherein the left-handed helical portion 172.1 abut the first left-handed helical portion 114.1, and the connector arm has returned to the abutment with the first axial portion 146.1 of the proximal guide, as illustrated in FIG. 16R. Thereby, the connector arm has been reset, in its initial position and is ready to guide the connector during a new activation and dosing cycle. From the intermediate arrangement in FIG. 16R to the relocked state in FIG. 16S the connector is moved distally into a seat, wherein the first transverse portion 144.1 abuts the first axial portion 174.2, and wherein the axial portions 144.1, 144.2, 174.1 and 174.3 prevents rotation.

Cap-On State Cap Locked State

The fifth user operation is to put the cap on as illustrated in FIG. 16T, hereby the protrusion 105.2 is inserted into the axial track portion 161.2, whereby it can be turned in order to arrange the device in the cap locked state, which was shown in FIG. 15B (cap locked state not shown in connection with detailed description of the operation). As seen on FIG. 16T, the axially extending rib is position for moving away from the protrusion 116, when the cap is turned into the locked position. Therefore, there is no interaction between the cap 105 and the shield 110, when the cap is locked.

Second Embodiment

FIG. 17-26 illustrate a second embodiment of an injection device 200 for delivering a plurality of fixed dosses according to the present disclosure. FIG. 17 shows an exploded view of injection device, and FIG. 18 a cross sectional view. FIG. 18-23 show further details of the individual structures and mechanism. FIG. 25-26 illustrate in details the interrelation of the mechanical structures during operation.

FIG. 17 shows a cap 205, a shield tip 219, a shield following portion 220.1 of a cleaning module also comprising a movable portion, corresponding to the movable portion 120.2 in the first embodiment 1. FIG. 17 further shows a needle hub 225 with a needle cannula 224, a tubular elongate housing structure 240, and a housing cap portion 260 to be connected at a distal end of the housing structure 240. The figure further shows a tubular elongate needle shield structure 210, a cartridge holder 230, a cartridge 235, a connector 270, a shield return spring 207, a drive tube 280, a dose drive spring 208, a piston rod 209, and a spring base 265. The figure further shows a piston washer 204 comprising a ratchet arm and an outer thread for engaging a toothed ring and an inner thread at the inner surface of the piston rod 209, respectively, whereby a zero point adjustment with respect to the piston in the cartridge 235 can be performed. FIG. 18 illustrates a cross sectional view of the injection device 200, wherein the injection device is in an out-of-pack state. The cross-sectional plane cuts through the windows 211 of the shield.

Housing Assembly

The injection device comprises a housing assembly, providing a rigid frame with guides and connectors for guiding and connecting the other components of the device. The housing assembly comprises the housing cap portion 260, the tubular elongate housing structure 240, the cartridge holder 230 with a window 231 and the spring base 265. After final assembly these structures are fixedly connected, and the housing assembly can provide a frame of reference for describing the relative movement and position of the other structures. The elongate housing structure 140 comprises an internal thread 254.3 for engaging an outer thread of the piston rod.

The injection device 200 comprises a drive mechanism and a triggering or activation mechanism. The drive mechanism comprises the piston rod 209, the drive spring 208, and the drive tube 280, and for expelling a dose the structures are operationally arranged in the housing. The triggering mechanism comprises the elongate shield structure 210 and the connector 280, and for triggering the dose expelling mechanism the structures are operationally arranged in the housing.

The tubular portion 254 comprises a middle guide 244 comprising an outer axial portion 244.1 arranged symmetrically around the longitudinal axis at a first radial position and thereby defining a first diameter and an inner axial portion 244.2 arranged symmetrically around the longitudinal axis a second radial position, and thereby defining a second diameter.

Needle Shield Assembly

The injection device further comprises a needle shield assembly comprising the shield tip 219 and the elongate shield structure 210. The elongate shield structure 110 comprises a window 211 for inspection of the drug, the elongate shield can be arranged in a first position of overlapping with the cartridge holder window 231, and in a second position with no overlap, wherein a solid portion of the elongate shield structure covers the window 231 in the second position.

Cartridge and Cartridge Holder

The cartridge holder 230 is adapted for receiving the cartridge 235. The cartridge holder comprises the window 231 for inspecting the drug in the cartridge 235. The cartridge 135 and the cartridge holder 230 is structurally and functionally similar to the cartridge 135 and cartridge holder 130 of the first embodiment, respectively.

Needle Assembly

The needle assembly comprising needle hub 225 and needle 224 are structurally and functionally similar to the needle assembly of the first embodiment.

Cap

The cap 205 is adapted for releasable mounting to the housing cap portion 260. The cap comprises an inner surface with a protrusion adapted to couple with a bayonet coupling track. The inner surface of the cap 105 further comprises an axially extending rib (not shown) protruding from the inner surface and adapted for transferring a torque to the shield structure 110 through an axially extending rib 216 on the outer surface of the shield. The cap 205 is structurally and functionally similar to the cap 105 of the first embodiment, with an exception that the cap 205 also encloses a main portion of the shield and the cartridge.

Spring Base

The spring base 265 is fixedly mounted to the housing structure 240 at the proximal end and is adapted to receive and support a compressible torsional drive spring 108.

Drive Spring

The drive spring 208 is pre-strained or winded up and positioned between the spring base and the drive tube 280. The drive spring is further adapted to induce a torque on the drive tube, whereby the medicament can be expelled. The drive spring comprises torsional and compressible sections. The ability to drive the drive tube in an axial direction enables an end of dose mechanism, and to enable a resetting of the drive tube.

Return Spring

The connector return spring 207 is positioned between the spring base 265 and the relock tube 279 and is adapted to urge the relock tube in the distal direction. In a return arrangement, the relock tube 279 abuts the shield 210, and the shield engages the connector, whereby the shield 210 and the connector 270 can be returned together with the relock tube 279.

Cleaning Assembly

The cleaning assembly is structurally and functionally similar to the cleaning assembly of the first embodiment.

Housing Structure

Figure 19:
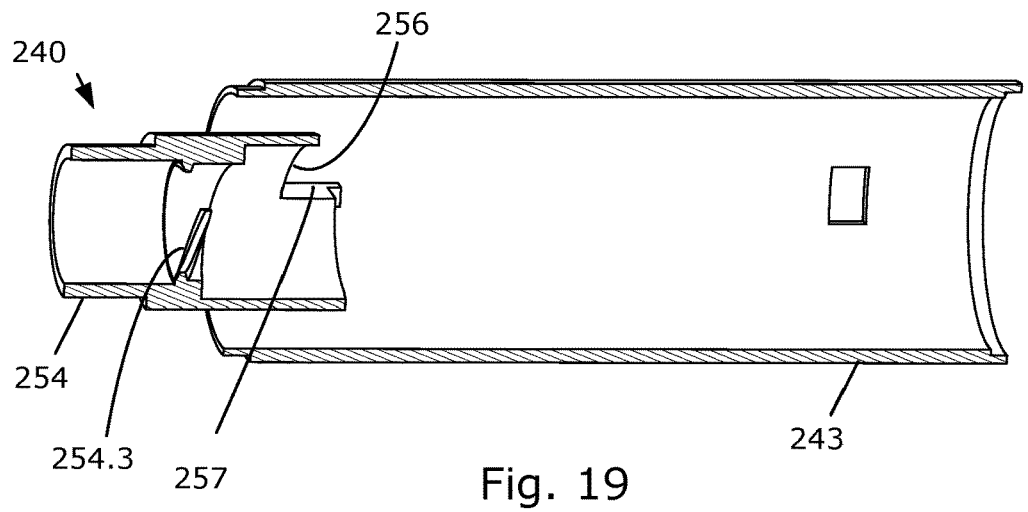
FIG. 19 illustrates details of the housing of the embodiment shown in FIG. 17.

FIG. 19 illustrates a perspective view of features arranged at the inner surface of the tubular housing structure 240 in an axial cut of the housing. As seen in FIG. 19 the tubular housing structure 240 comprises an outer tubular portion 243 and an inner tubular portion 254. In the illustrated example, the inner tubular portion 254 is integrally connected to the outer tubular portion. The outer tubular portion comprises an outer surface with an outer diameter and an inner surface with an inner diameter, wherein the outer tubular portion is adapted for accommodating the drive mechanism assembly and the relock tube 279.

The housing structure 240 comprises a guide structure comprising an axial surface portion 256 providing a sliding surface and a rotational stop, and a helical surface portion 257 providing a sliding surface adapted for guiding the drive tube 280 during dosing.

Figure 20:
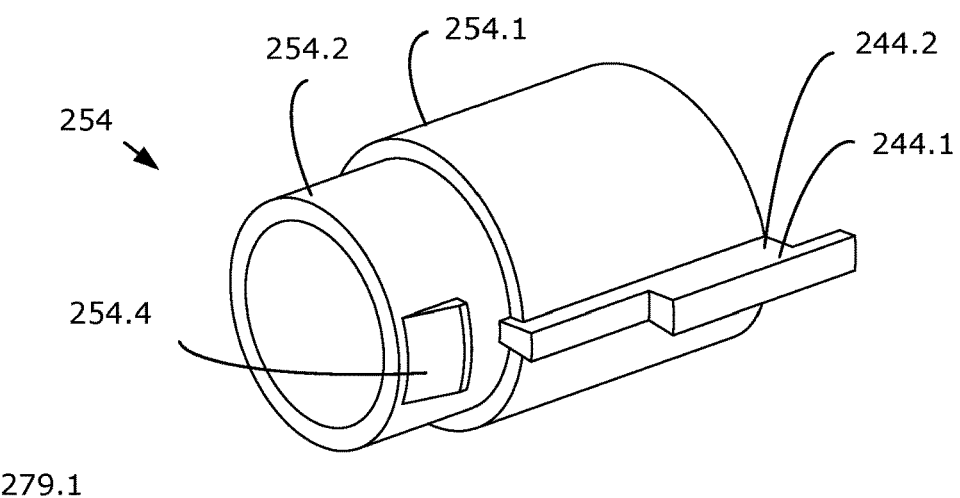
FIG. 20 illustrates details of the inner tubular portion of the housing of the embodiment shown in FIG. 17.
Figure 21:
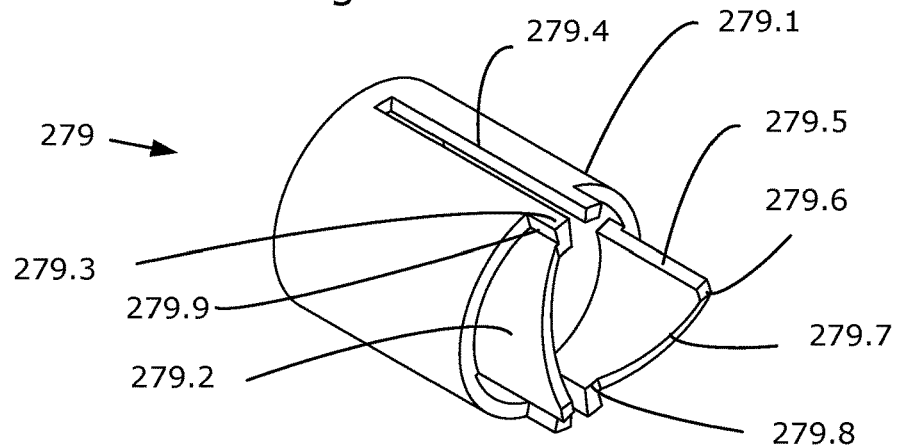
FIG. 21 illustrates details of the relock tube of the embodiment shown in FIG. 17.

FIG. 20 illustrate in detail the inner tubular portion 254 in a perspective view, wherein the outer tubular portion 243 has been cut away. The inner tubular portion comprises a tubular drive tube engaging portion 254.1 for accommodating a distal portion of the drive tube, and a tubular drive piston rod engaging portion 254.2 comprising a thread 254.3 for threadably engaging the piston rod 209. The piston rod engaging portion further comprises a connector 254.4 for making a snap connection with the cartridge holder 230.

Zero-Point Adjustment Mechanism

As seen in FIG. 17, the piston washer comprises an outer thread and a rachet arm for cooperating with a thread and a toothed ring on the inner surface of the piston, whereby zero-point-adjustment is enabled, in analogy with the method described for the first embodiment.

Drive Mechanism

The construction and functionality of the drive mechanism of the second embodiment is similar to the first embodiment. In particular, the drive tube 280 is axially splined to the piston rod. FIGS. 23A and 23B illustrate the drive tube 280 in perspective views from different angles. As seen in FIG. 23, as a deviation to the first embodiment, the drive tube 280 of the second embodiment comprises a closed guide track 284 comprising a first transverse portion 284.1, a right-handed helical portion 284.2, a left-handed helical portion 284.3. The transverse guide portion 284.1 comprises a proximally oriented surface providing a connector seat, wherein the connector is seated before and after activation of the drive tube. The transverse portion further comprises an abutment structure 283 comprising a distally oriented surface portion 283.1 providing an abutment surface for abutting the connector during activation. The right-handed helical portion 284.2 comprises a distal surface providing an abutment surface for the connector, in response to immature release of shield pressure, i.e., a split dose prevention feature. The left-handed helical portion 284.3 provides a ramp surface for rotating the connector at the end of dose, whereby resetting of the shield is initiated. As for the first embodiment 100, the drive tube of the injection device 200 comprises a guide structure comprising an axial surface portion 282 adapted for slidably engaging the axial surface portion 256 of the housing in a rotationally locked arrangement, and a helical surface portion 289 for slidably engaging the helical surface portion 257 of the housing during dosing.

The same considerations for incorporating a torsion spring in the drive mechanism in the second embodiment provides the same advantages as mentioned for the first embodiment.

Elongate Shield Structure

FIG. 24 shows a perspective view of the cylindrical elongate shield structure 210. The proximal portion of the shield is to be arranged inside the connector 270 which again is to be arranged inside the housing portions 240, 260. The elongate shield structure 210 comprises a tubular portion comprising an outer surface with an outer diameter and an inner surface with an inner diameter. The axially extending rib 216 is positioned at the distal end ant protrudes from the outer surface. The rib is adapted for cooperating with the internal rib of the cap 205.

The shield structure 210 further comprises a radial guide 212 arranged at the proximal end and extending radially, whereby the shield is adapted for cooperating with the connector 270.

The elongate shield structure 210 further comprises a proximal guide 214 positioned at the proximal end of the shield structure 210. On FIG. 24 the proximal face being the proximal guide can be seen. The proximal guide 214 is adapted to cooperate with the connector 270, and the relock tube 279. The proximal guide 214 extends in the axial and circumferential direction and comprises a first transverse portion 214.1, an axial portion 214.2, a right-handed helical portion 214.3, and a second transverse portion 214.4. The proximal guide 214 further comprises a cut-out 214.5 providing a rotational lock, for locking the shield in a shield initiated state, wherein it cannot be returned to an out-of-pack state. The cut-out provides a right-handed helical guide portion 214.6. The guide portions 214.1-214.4 are all surface portions providing a proximal face of the proximal guide 214.

Connector

FIG. 22 shows a perspective view of the connector 270 to be arranged inside the tubular housing portions 240, 260 and between the elongate shield structure 110 and the drive tube. The connector 270 is adapted for establishing a connection between the shield 210 and the drive tube 280, and for activating the drive tube 280. The connector 270 comprises a distal guide 272 adapted to cooperate with the proximal guide 114 of the shield. The distal guide 272 is extending in the circumferential direction and comprises a transverse surface portion 272.1 being distally oriented surface.

The connector further comprises a step-wise helical track 274 for cooperating with the radial guide 212 of the shield. The step-wise helical track comprises a distal transverse portion 274.1, a distal helical portion 274.2, a middle transverse portion 274.3, a proximal helical portion 274.4 and a proximal transverse portion 274.5. Due to the helical portions of the step-wise helical track, a rotational movement of the shield 210 can be transferred into a proximal movement of the shield, and due to the transverse portions of the step-wise helical track 274, a distally oriented force on the shield can be transferred to the connector 270, whereby the shield can move distally. If the shield exerts a distal force on the helical portions of the step-wise helical track 244, the connector may move distally or both distally and rotationally.

The connector 270 comprises a first tubular portion 270.1 with a full 360 degree circumference, and a second tubular portion 270.2 with two cut-outs, whereby the remaining portions of the second tubular portion forms two axially extending tube portions 276. The first tubular portion comprises the step-wise helical track 274, and the two axially extending tube portions 276 comprises a distal transverse surface 272.1 forming the distal guide 272, a first axial surface providing a first axial guide 276.1, and a second axial surface, positioned clockwise to the first surface, providing a second axial guide 276.2. The shield can be arranged within, the first tubular portion 270.1 with the radial guide 212 extending through the step-wise helical track 274. The axially extending tube portions 276 extends in the proximal direction from the inner surface of the first tubular portion 270.1, and therefore has a smaller diameter. The transverse surface portion 272.1 is provided on the distally oriented surface of the axially extending tube portions 276, and as the diameter of the tube portions 276 corresponds to the diameter of the shield 210, the proximal guide 214 having a proximally oriented surface is adapted to cooperate with the transverse guide portion 272.1. The diameter of the axially extending tube portions 276 further corresponds to the diameter of the inner axial portion 244.2 of the middle guide, whereby the axially extending tube portions 276 can cooperate with the inner axial portion 244.2. The connector 270 is having an outer surface with an outer diameter and an inner surface with an inner diameter. As illustrated on FIG. 18, which is a cross sectional view of the injection device 200, the outer surface of the first tubular potion 270.1 of the connector is arranged in close proximity with the inner surface of the tubular housing cap portion 260. The axially extending tube portions 276 surrounds the inner tubular portion 254 of the housing and the drive tube 280. The axially extending arms 276 are further adapted to cooperate with the middle guide 244.1 of the housing and thereby guide the movement of the connector relative to the housing.

The connector 270 further comprises an activation tab 278 arranged at the proximal end of the axially extending tube portions 270.2, and extending radially from the inner surface in a negative radial direction, i.e., towards the centre of the tubular portion. The activation tab 278 extends into the closed guide track 284 of the drive tube. The activation tab 278 comprises a first transverse portion 278.1 providing a proximally oriented contact surface adapted for engaging the distally oriented surface 283.1 of the abutment structure in the transverse portion 284.1 of the closed guide track, and thereby enabling a proximal movement and activation of the drive tube 280. The activation tab 278 further comprises a proximally oriented surface portion 278.2 adapted to engage a distally oriented surface of the closed guide track 284, whereby the connector can be guided during a dose cycle, and whereby a split dose can be prevented in response to immature release of the proximal pressure on the shield. In response to guiding the proximal portion 278.2 of the activation tab along the left-handed helical guide portion 284.3, a shield relock mechanism is initiated.

Relock Tube

The relock tube 279 comprises a first tubular portion 279.1, and a second tubular portion with two cut-outs, whereby the remaining portions of the second tubular portion forms two axially extending tube portions 279.2. The relock tube comprises an axially extending guide track 279.4 extending from a relatively small distance from the proximal end (e.g. 1/10 of the length of the relock tube) to the distal end. The two axially extending tube portions 279.2 comprises an axial guide portion 279.5, a first transverse guide portion 279.6, a right-handed helical portion 279.7, and a second transverse portion 279.8. The axially extending tube portions 279.2 further comprises an axial portion 279.9 providing a rotational stop and axial guide for the connector. The axially extending tube portions 279.2 extends in the proximal direction from the inner surface of the first tubular portion 279.1, and therefore has a smaller diameter. The helical and transverse guide portions 279.6-279.8 is provided on the distally oriented surface of the axially extending tube portions 279.2, and as the diameter of the tube portions 279.2 corresponds to the diameter of the shield 210, the proximal guide 214 having a proximally oriented surface is adapted to cooperate with the helical and transverse guide portion 279.8-279.8. The diameter of the axially extending tube portions 279.2 further corresponds to the diameter of the inner axial portion 244.2 of the middle guide. The diameter of the first tubular portion corresponds to the diameter of the outer axial portion 244.1 of the middle guide. The axially extending guide track 279.4 is adapted to cooperate with the outer portion 244.1 of the middle guide, whereby the relock tube 279 is rotationally locked and axially guided between a distal position defined by the proximal end of the guide track 279.4 and a proximal position (FIG. 18 shows that they may be an axial play between the outer portion 244.1 and the proximal end of the track). The relock tube 279 is having an outer surface with an outer diameter and an inner surface with an inner diameter. As illustrated on FIG. 18, the outer surface of the first tubular potion 279.1 of the relock tube is arranged in close proximity with the inner surface of the outer tubular portion 243 of the housing, and the return spring is position between the spring base 265 and a proximal edge of the relock tube 279, whereby the relock tube can be distally biased, in response to a proximal movement. The axially extending tube portions 279.2 surrounds the inner tubular portion 254 of the housing, and can cooperate with the axially extending tube portions 270.2 of the connector.

Detailed Description of the Operation of the Device

FIG. 25A to 26B collectively illustrate the relative and functional arrangement of the different structures during the sequence of states of the injection device 200, and thereby illustrate the operation of the device in details.

In an embodiment of the present disclosure, the injection device 200 for sequentially delivering a plurality of fixed dosses comprises: a housing comprising an elongate housing structure 240, a cartridge holder 230, and a housing cap portion 260, an internal thread, a shield comprising the elongate shield structure 210 and the needle tip 219, a needle hub 225 comprising the fixedly attached needle cannula 204, a cap 205 removably mounted on the housing and adapted for covering a main portion of the shield, a cartridge 235 with a movably arranged cartridge plunger or piston 236 and a drive mechanism comprising a torsional drive spring 208, a drive tube 280 and a piston rod 209 with an outer thread for cooperating with the internal thread of the housing, the piston rod is arranged in connection with the piston 236, and wherein the torsional spring is adapted to provide a torque for rotating the drive tube 280 relative to the housing. The drive tube comprises a ratchet mechanism 281, 265.1 ensuring rotation in a dosing direction and blocking in a non-dosing direction. The drive tube is axially splined with the piston rod, whereby relative axial movement is allowed, and relative rotation is prevented. The drive tube is adapted to advance the piston rod, in response to rotating the drive tube in the dosing direction, and due to the threaded connection with the housing, the piston rod is adapted to advance the piston 236 in the cartridge 235 to expel a fixed dose. The drive mechanism is adapted to be activated, by changing the drive tube from a distal position, wherein the drive mechanism is in a stationary mode, to a proximal position, wherein the drive mechanism is in a dosing mode. In the distal position, the drive tube is rotationally locked to the housing. In the proximal position, the drive tube is rotationally unlocked from the housing, and the provided torque can rotate the drive tube a predetermined angel to expel the fixed dose. In the stationary mode of the drive mechanism, the piston rod is rotationally and axially locked, and the piston rod is rotationally locked to the housing through the splined connection with the drive tube 280, and axially locked through the threaded connection with the housing.

The torsion spring 208 is pre-strained to deliver the plurality of doses without restraining during use. The drive mechanism is adapted to change mode upon activation, and as explained later the drive mechanism is adapted to be repeatably activated until the last dose has been expelled.

The cap can be arranged in an axially locked position and an axially unlocked position. The cap can be changed between the positions by turning the cap relative to the housing. For the cap being in the axially unlocked position, the cap can be removed from the housing.

The shield can be arranged in different positions. An initial position defined by an initial angular position and a corresponding initial axial position. An unengaged position defined by an unengaged angular position and a corresponding unengaged axial position. An engaged distal position defined by an engaged angular position and a corresponding distal engaged axial position. An engaged proximal position defined by the engaged angular position and a corresponding proximal engaged axial position. In the initial position, the shield is adapted to allow a counterclockwise movement. In the unengaged position, the shield is adapted to prevent clockwise movement and to allow clockwise movement. The shield is not engaged with the connector, in the sense that a proximal movement of the shield is not transferred to a proximal movement of the connector, whereby the shield cannot activate the drive tube in this position. In the engaged distal position, the shield is adapted to prevent counterclockwise and distal movement of the shield, and further adapted to allow proximal movement. In the engaged distal position, the shield is further adapted to allow a clockwise rotation, if the applied torque exceeds a predefined threshold. For the shield being in the initial position and the unengaged position the needle tip is covered by the shield. In the engaged position, the shield is adapted to be moved from the engaged distal position, wherein the needle tip is uncovered by the shield and wherein pressure in the reservoir can be released, and proximally to the engaged proximal position, wherein the needle tip extends further from the shield and can be inserted into the subcutaneous layer of a subject. In this position further proximal movement may be prevented by the shield tip 119 being blocked against the needle hub 125. The shield can be manually operated between the different positions by the user. As appears for the shield being in the initial position, the unengaged position, the distal engaged position and the proximal engaged position, defines four different sets of angular and axial positions: three different angular position and four different axial positions.

The connector can be arranged in an initial or first position defined by a first angular and a corresponding distal position, wherein the connector is allowed to move to a proximal position, guided along the rotationally locked relock tube 279 until the connector 270 meets an axial stop on the housing or the shield tip 219 abuts the hub 225. The connector can therefore further be arranged in a second position defined by the first angular position and the proximal position. Even further, the connector can be arranged in a third position defined by a second angular position and a corresponding distal position, wherein the first and the third positions are defined by the same axial positions.

FIG. 25A to 26B collectively illustrate a portion of the injection device 200 arranged in different states and intermediate arrangements, wherein an outer portion of the housing and the entire cap has been cut away to illustrate some of the internal structures. Each illustrated state is illustrated with a figure wherein some of the internal components are hidden by the connector and the relock tube, e.g., 25B1, and each illustrated state is illustrated with a figure, wherein the outer portion of the relock tube and a portion of the outer portion of the connector has been removed, e.g., 25B3. Some illustrated states are also provided grayscale illustrations, e.g., 25B2 corresponding to 25B1 and 25B4 corresponding to 25B3.

Out-of-Pack State

FIG. 25A illustrates a portion of the injection device 200 in the out-of-pack state, and shows the shield structure 210, the cartridge holder 230, the connector 270, the drive tube 280 and the return spring 207, the relock tube 279, and the spring base 265. FIG. 25A1 illustrates the portion of the injection device in black and white, and FIG. 25A2 illustrates the same in grayscale to better illustrate the different components of the construction.

Cap Unlocked State

The first user operation is to turn the cap counterclockwise until it reaches the cap axially unlocked position, whereby the shield is changed from the initial position to the unengaged position, and whereby the device is changed from the out-of-pack state to the cap unlocked state, as shown in FIGS. 25B1 and B2. In the cap unlocked state, the cap can be moved axially. The cap unlocked state is also referred to as the shield-initiated state, as the shield has initiated the device, or the shield unengaged state, as the shield is not engaged with the connector to activate the device or the non-activation state as the shield cannot activate the drive mechanism. In contrast to the embodiment 100, the shield 210 in the embodiment 200 is not necessarily axially locked to the housing in this state, but as the shield does not engage the connector, an axial movement cannot be transferred from the shield to the connector, and the connector cannot be moved to activate the drive tube 280. As the radial guide 212 of the shield engages the step-wise helical track 274 of the connector 270, during the proximal helical movement of the shield from the initial to the unengaged position, the radial guide 212 abuts a proximal surface of the distal helical guide portion 274.2 of the step-wise helical track. In the unengaged position the radial guide rests on the middle transverse portion 273.4, wherein there are no proximal sides on the track 274. During the proximal helical movement of the shield, the shield has moved the relock tube 279 proximally against the biasing force of the return spring 208, and in the unengaged position the axially extending portions 279.2 of the relock tube has moved into the cut-out 214.5 whereby a rotational lock is provided. For the shield being in the unengaged position, the right-handed helical portion 279.7 of the relock tube abuts the right-handed helical guide portion 214.6 of the cut-out, and the right-handed helical portion 214.3 of the proximal guide, and thereby urges the shield in the distal direction. The distal force is transferred from the shield to the connector, through the abutment between the radial guide 212 and the track 274, whereby the connector is also biased in the distal direction. Therefore, in the following states the relock tube 279, the shield 210 and the connector are distally biased. On FIG. 25B it appears that the shield does not extend to the spring base and therefore not is compressed. However, even though the illustrated embodiment is a little imprecise, the shield is at least slightly compressed in this state. Otherwise, the components would rattle inside the device when turned from up to down or vice versa.

Cap-Off State

The second user operation is to pull the cap in a distal direction, whereby the device is changed from the cap unlocked state to the cap-off state.

As the cap is not shown on the FIGS. 25A-26B, FIGS. 25B1 and B2 also illustrate the cap-off state.

Shield Engaged State or Activation State

The third user operation is to turn the shield, being in the unengaged position or non-activation position (as it cannot activate the drive mechanism), in the counterclockwise direction until it reaches the engaged distal position or activation position, and whereby the device has been changed from the cap-off state to the shield unlocked state.

From the shield unengaged position to the shield engaged distal position shown in FIGS. 25C1 and C2, the shield rotates in a proximal helical movement guided by the distal helical portion 274.4 followed by a pure rotational movement guided by the proximal transverse portion 274.5. During the proximal helical movement of the shield along the distal helical portion 274.4, the right-handed helical guide portion 214.6 of the cut-out and the right-handed helical portion 214.3 of the shield slides in abutment with the right-handed helical portion 279.7 of the relock tube, whereby the rotationally locked relock tube 279 is forced in the proximal direction. During the pure rotational movement of the shield, the abutment between the helical portion 279.7 of the relock tube and the helical portions 214.7, 214.3 of the shield, shifts to an abutment between the right-handed helical portions 214.3, 279.7 only and then to an abutment between the second transverse portion 214.4 of the proximal guide and the first transverse guide portion 279.6 of the relock tube. As the abutment surface between the second transverse portion 214.4 of the shield and the first transverse portion 279.6 of the relock tube extends in a direction normal to the biasing force of the return spring, the abutment provides a static position of the relock tube 279 and the shield 210. Due to the biasing force and the abutment between the transverse portions 214.4, 279.6, a releasable locking mechanism is provided between the shield 210 and the relock tube 279. To release the lock, a torque exceeding a release threshold torque is required. During the helical movement of the shield, the first transverse surface portion 214.1 of the proximal guide of the shield and the transverse surface portion 272.1 are brought into abutment, and during the pure rotational movement the shield slides relative to the connector until abutment between the axial portion 276.1 of the axially extending portion 276 and the axial portion 214.2 of the proximal guide. Therefore, releasing the lock and thereby establishing an abutment between the helical portions 214.3, 279.7 of the shield and the relock tube will also disengage the transverse portions 214.1, 272.1 of the shield and the connector. Another axial portion 276.2 of the axially extending tube portions 276 of the connector is rotationally locked in the counterclockwise direction against the axial portion 279.9 of the rotationally locked relock tube, which is slidably arranged with the middle guide 244 engaged in the axial track 279.4. The activation tab 278 of the connector is seated in the transverse portion 284.1 of the closed guide track in the drive tube. In the engaged distal position, the shield is adapted to move the connector in the proximal direction to activate the drive tube.

Dosing State

The fourth user operation is to push the shield, being in the engaged distal position, in a proximal direction until it reaches the engaged proximal position, and whereby the device has been changed from the shield unlocked state to the dosing state. The dosing state is illustrated by the arrangements shown in FIG. 25D to 25E.

From the shield engaged distal position to the shield engaged proximal position shown in FIGS. 25D1 and D2, the shield moves in a proximal and pure axial movement guided by the relock tube traveling along the middle guide 144. During the proximal movement of the shield, the, by the shield, engaged relock tube 179 translates proximally to compress the return spring 208 even further, and the, by the shield, engaged connector translates proximally, whereby the activation tab 278 engages a proximal surface of the transverse portion 284.1 of the closed guide track, and wherein the drive tube also is translated proximally. Thereby, the drive tube has been moved from the distal position, wherein the drive tube is rotationally locked to the housing to the proximal position, wherein the drive tube is rotationally unlocked from the housing. As illustrated in FIG. 25D2, the torque provided by the drive spring 207 has rotated the drive tube, whereby the activation tab has slided out of the transverse portion 284.1 and into the right-handed helical portion 284.2 of the closed guide track. FIG. 25D also reveals the axial portion 282 for abutting the axial portion 257 (see FIG. 19) of the inner tubular portion 254 of the housing, and the helical portion 256 of the housing for abutting the helical portion 289 (see FIG. 23) of the drive tube.

FIG. 25E illustrates another arrangement in the dosing state, following the arrangement in 25D, wherein the drive tube 180 has rotated further during dosing, and whereby the activation tab 278 is arranged at a proximal end of the right-handed helical portion 284.2, wherein the abutment is about to change from the right-handed helical portion 284.2 to the left-handed helical portion 284.3. As in the previous state, the connector abuts the axial portion 114.2 of the proximal guide of the shield, and the first transverse guide portion 279.6 of the relock tube abuts the second transverse portion 214.4 of the proximal guide of the shield to transfer an axial distal force from the relock tube 279, through the shield 210 and to the connector 270.

Initialization of Automatic Relock Mechanism

As the drive tube stops rotating by reaching an end of dose, the proximal portion 278.2 of the activation tab 278 is brought out of abutment with the right-handed helical track, whereby the connector is no more prevented in moving in a distal direction. As axial movement of the connector is not prevented by the drive tube, the connector will move axially in a distal direction and rotate, in response to releasing the pressure from the shield, whereby the connector will move into engagement with the left-handed helical portion 184.3 of the drive-tube. Hereby, the automatic relock mechanism has been initiated.

Split Dose Prevention

During a dosing cycle the activation tab 278 is engaged in the closed guide track 284. Therefore, in response to lifting the shield from the skin, before the dose is completed, the activation tab will be blocked by the first transverse portion 284.1, or the right-handed helical portion 284.2, of the guide track 284 and the drive tube will continue to rotate until the dose has been completed. At completion of rotation, the connector will push the connector with the activation tab and the shield distally, but a split or interrupted dose has been prevented, whereby it is ensured that the next dose can be taken correctly. If the shield was extended to a distal position, the needle tip would be placed in the cleaning chamber, whereby an overpressure could be generated in the cleaning chamber. The overpressure could unintentionally stop the dosing.

Relocked State

The fifth user operation is to release the axially oriented force on the shield, by lifting the needle tip 219 from the skin, whereby the shield being in the engaged proximal position, is moved in the distal direction until it reaches the unengaged position, and whereby the device has been changed from the dosing state through an intermediate arrangement shown in FIG. 25F to the unengaged state or non-actuation state shown in FIG. 25G.

Automatic Relock Mechanism

FIG. 25F illustrates an intermediate arrangement between the dosing state and the unengaged state shown in FIG. 25G, wherein the drive tube has rotated into abutment with the axial portion 257, whereby the dose is completed. During the rotation of the drive tube, and in response to releasing the pressure from the shield, the activation tab 278 has shifted to abutment with the left-handed helical portion 284.3 and due to the compression from the return spring 207, the activation tab 278 has been forced to move along the left-handed helical track and thereby rotate and axially move the connector 270 to the second angular and distal position. The force from the compression spring is transferred from the relock tube through the shield and to the connector. During the rotation of the connector, the shield has been rotated due to the abutment between the connector and the axial portion 214.2 of the proximal guide of the shield. Due to the rotation of the shield, and as the relock tube is rotationally locked, the abutment between the shield and the relock tube has shifted to abutment between the right-handed helical portion 214.3 of the shield and the right-handed helical guide 274.7 of the relock tube. The helical abutment surface allows an axial movement of the relock tube 279 to be transferred into a rotational movement of the shield, and as the relock tube is distally biased, the relock tube is moved distally and the shield is rotated into the unengaged position, whereby the first transverse portion 214.1 of the locking structure 215 of the shield is brought out of abutment with transverse portion 272.1 of the distally oriented transverse guide portion 272 of the connector. As the two transverse portions 214.1, 272.1 are transverse, they can be forced to slide apart in response to the application of relative rotation.

Cap-On State Cap Locked State

The fifth user operation is to put the cap on, which is not illustrated for the injection device 200, hereby the protrusion on the inner surface of the cap is inserted into an axial track portion on the housing, whereby it can be turned in order to arrange the device in the cap locked state. The cap locked state for injection device 200 is not illustrated. The cap 205 does not engage the shield, when rotated back to the locked state, and the shield is therefore not pushed toward the initial position.

FIGS. 26A and 26B illustrate two arrangement in taking the second or higher number of dose, in case the connector does not rotate back to its first position. As the relock tube moves to its distal position, the connector 270 can either be left in the third position with a second angular position as shown in FIG. 25G2, or it can be forced by the shield 210 to rotate to the first position with the first angular position, as the radial guide slides distally along the proximal helical guide 274.4. In the latter case, a new dose will start from the arrangement shown in FIG. 25B. In the first case, a new dose will start from the arrangement shown in FIG. 25G2, and continue to the arrangement shown in FIG. 26A, wherein the shield urges the relock tube in the proximal direction until the axial portion 214.2 of the shield abuts the axially extending portions 270.2 of the connector. In response to further rotation, the connector is pushed back to the first position with the first angular position as shown in FIG. 26. From here the next dose continues as described from FIG. 25C.

Additional Embodiments

The described additional alternative embodiments are not individually illustrated and are not provided with reference numbers. However, features of the alternative embodiments correspond to features of the illustrated embodiments, whereby the features of the alternative embodiments provide one or more functions that are similar or equal to the features of the illustrated embodiments.

In an alternative embodiment is provided, a drug delivery device for delivering a predefined fixed dose, wherein the drug delivery device comprises:
  a housing assembly,
  a drug reservoir with a piston
  a drive mechanism comprising a piston rod for advancing the piston to expel a drug, and a drive tube, wherein the drive mechanism is adapted to deliver the predefined fixed dose in response to activation;
  an activation mechanism for activating the drive mechanism, in response to moving the drive tube in an axial direction,
wherein the housing assembly comprises a guide structure for guiding the drive tube during activation and delivery of a dose, wherein the guide structure comprises an axial portion providing a sliding surface for guiding the drive tube during activation, and for providing a rotational stop defining an end of dose, and a helical portion providing a sliding surface adapted for guiding the drive tube during dosing; wherein the drive tube comprises a guide structure comprising an axial portion adapted for slidably engaging the axial portion of the housing assembly for activation, and a helical portion for slidably engaging the helical portion of the housing assembly during dosing during dosing.

Hereby, is provided a drug delivery device, wherein the drive mechanism comprises helical and axial guide portions to provide a fixed dose upon activation.

The helical portion of the housing assembly corresponds to the helical portion 157, 257 of the housing of first and second embodiment, and the axial portion of the housing assembly corresponds to the axial portion 156, 256 of the housing of the first and second embodiment. The drive tube, the torsional drive spring and the piston rod corresponds to the drive tube 180, 280, the torsional drive spring 108, 208, and the piston rod 109, 209. The axial portion of the drive tube corresponds to the axial portion 182, 282 of the drive tube of the first and second embodiment, and the helical portion of the drive tube corresponds to the helical portion 189, 289 of the drive tube of the first and second embodiment.

In an alternative embodiment, the guide structure of the housing assembly is a closed guide providing a work cycle for the drive tube, and wherein a starting position and an end of dose position of the drive tube is the same.

In an alternative embodiment, the housing assembly further comprises an inner tread, wherein the piston rod comprises an outer thread engaging the inner thread of the housing assembly.

In an alternative embodiment, the drive tube is axially splined to the piston rod.

In an alternative embodiment, the drive mechanism further comprises a motor mechanism for imparting rotation of the drive tube for delivering a dose, in response to activation of the drive mechanism. The drive tube is axially splined to the piston rod, whereby the drive tube is rotationally locked relative to the piston rod. The drive mechanism further comprises a return mechanism for moving the drive tube in an axial direction, and thereby returning the drive tube after activation. Hereby, the drive tube is reset in the initial position after activation.

In an alternative embodiment, the triggering mechanism comprises a movably arranged connector, wherein the connector comprises an activation tab, and wherein the activation tab is adapted for engaging a surface portion of the drive tube, in response to moving the connector in an axial direction, whereby the connector is operatively connected to the drive mechanism and adapted for triggering the drive mechanism, wherein the surface portion is oriented in a direction towards the activation tab.

The connector and the activation tab correspond to the connector 170, 270 and the activation tab 178, 278 of the first and second embodiment. The surface portion correspond to distally oriented surface 183.1, 283.1 of the first embodiment and second embodiment.

In an alternative embodiment, the drug delivery device comprises:
  a stationary state, wherein the drive tube is arranged in a
    first axial position and a first angular position, wherein
    the drive tube is locked to the housing, wherein the
    guide structure of the drive tube abuts the axial portion of the housing assembly and the helical portion of the guide structure of the housing assembly,
a first dosing state, wherein the drive tube is arranged in a second axial position and the first angular position, whereby the drive mechanism is activated and
a second dosing state, wherein the helical portion of the guide structure is slidably arranged along the helical portion of the guide structure of the housing assembly, whereby a dose can be expelled.

In an alternative embodiment, the connector is adapted to move the drive tube between the first axial and the second axial position, whereby the drug delivery device is changed from the stationary state to the first dosing state, in response to moving the connector from a first axial to a second axial position, and wherein the drive mechanism is adapted to rotate the drive tube, and thereby change the injection device from the first dosing state, through the second dosing state and to the stationary state, in response to setting the injection device in the first dosing state.

Wherein the first and second position of the connector is different from the first and second position of the drive tube, wherein the axial distance between the first and second position of the connector is larger than or equal to the axial distance between the first and second position of the drive tube.

In an alternative embodiment, the motor mechanism comprises a torsional drive spring for rotating the drive tube by unwinding, wherein the drive spring is fixed between the housing assembly and the drive tube, wherein the drive spring further is compressible for distally moving the drive tube axially during rotation, whereby the drive spring provides the returning mechanism for returning the drive tube after activation.

In an alternative embodiment the drive spring comprises a compressible section, wherein the compressible section corresponds to the compressible section 108.4 of the first and second embodiment.

In an alternative embodiment, the activation tab comprises a transverse surface portion, and wherein the engageable surface portion of the drive tube is transverse, whereby initiation of dosing is provided by a rotational movement induced by the torsional drive spring.

In an alternative embodiment, the drug delivery device comprises a spring base rotationally arranged relative to the housing assembly, wherein a one-way ratchet mechanism is provided between the rotationally arranged spring base and the housing assembly, whereby the spring can be strained by rotating the spring base. Hereby, the torsional spring can be winded up instead of or in addition to being pre-strained.

In an alternative embodiment, the motor mechanism comprises a compression drive spring, wherein the activation tab comprises a helical surface portion, wherein the engageable surface portion of the drive tube for activating the drive tube comprises a helical surface portion, wherein the activation tab is adapted to impart an initial rotation of the drive tube in the dosing direction, in response to engaging the tab and moving the drive tube against the biasing force of the compression spring and between the distal and the proximal position, and wherein the helical portion of the housing assembly and the compression spring is adapted to provide further rotation of the drive tube, in response to the initial rotation, whereby a complete fixed dose can be delivered.

The tab corresponds to the tab 183, 283 of the first and second illustrated embodiment.

In an alternative embodiment, the piston rod comprises an axially extending track wherein the drive tube comprises inward protrusions adapted to slidably engage the axial track, whereby the drive tube is rotationally locked relative to the piston rod.

In an alternative embodiment, the axial portion and the helical portion of the guide structure of the housing is an axial surface portion and a helical surface portion, respectively, and wherein the axial portion and the helical portion of the guide structure of the drive tube is an axial surface portion and a helical surface portion, respectively.

In an alternative embodiment, the movement of the connector from the first axial to the second axial position is a pure axial movement.

In an alternative, embodiment, the first axial position is a distal position, and the second axial position is a proximal position.

In an alternative embodiment, the drug delivery device is an injection device.

In an alternative embodiment, the injection device comprises a shield for operating the connector, wherein the shield is adapted to cover a portion of a needle cannula in a distal position, and for exposing the needle cannula in a proximal position, wherein, for the shield being in the proximal position, the needle can be inserted into a subject, and wherein the shield is adapted to move the connector between the first and the second axial position, in response to moving the shield from the distal to the proximal position, wherein the first and the second position of the connector is a distal and a proximal position.

The shield and the needle cannular correspond to the shield 110, 210 and the needle cannula 124, 224 of the first and second embodiment.

In an alternative embodiment a drug delivery device 100, 200 for delivering a fixed dose, wherein the drug delivery device comprises:
  a housing assembly,
  a drug reservoir with a piston
  a drive mechanism comprising a piston rod 109, 209 operationally arranged in the housing assembly and adapted for advancing the piston to expel a drug during dosing, and a drive tube 180, 280 operationally arranged with the piston rod 109, 209, wherein the drive tube 180, 280 is adapted to be axially movable relative to the housing assembly and rotationally blocked in a stationary state, and adapted to be axially movable and rotatable relative to the housing in a dosing state, wherein the drive mechanism is adapted for axial movement and rotation of the drive tube 180, 280 in the dosing state and thereby advance the piston rod 109, 209 to deliver the fixed dose in response to activation;
  an activation mechanism for activating the drive mechanism, in response to moving the drive tube in an axial direction,
wherein the housing assembly comprises a guide structure for guiding the drive tube during activation and delivery of a dose, wherein the guide structure comprises an axial portion 156, 256 providing a sliding surface for guiding the drive tube during activation, and for providing a rotational stop defining an end of dose position, and a helical portion 157, 257 providing a sliding surface adapted for guiding the drive tube 180, 280 during dosing;
wherein the drive tube 180, 280 comprises a guide structure comprising an axial portion 182, 282 adapted for slidably engaging the axial portion of the housing assembly for activation, and a helical portion 189, 289 for slidably engaging the helical portion of the housing assembly during dosing, whereby the drive tube 180, 280 can be guided along the axial portion 156, 256 without rotation and thereby changed from the stationary state to the dosing state during activation, whereby the drive tube 180, 280 can be moved axially and rotated by the drive mechanism in the dosing state, and whereby the drive tube 180, 280 can be guided along the helical portion 189, 289 until the end of dose position and thereby changed from the dosing state to the stationary state, in response to activation of the drive mechanism.

In an alternative embodiment, the housing assembly further comprises an inner tread, wherein the piston rod 109, 209 comprises an outer thread engaging the inner thread of the housing assembly, whereby the piston rod is operationally arranged with the housing.

In an alternative embodiment, the drive tube 180, 280 is axially splined to the piston rod, whereby relative axial movement is allowed and relative rotation is prevented, and whereby the piston rod 109, 209 is advanced in response to rotation of the drive tube (180, 280), whereby the drive tube is operationally arranged with the piston rod.

In an alternative embodiment, the piston rod is axially splined to the housing assembly, whereby the piston rod is axially movable and rotationally locked relative to the housing assembly, wherein the drive tube further comprises an inner thread, wherein the piston rod further comprises an outer thread for threadably engaging the inner thread of the drive tube, whereby the piston rod is operationally arranged with the housing assembly and the drive tube and wherein the piston rod is advanced during rotation of the drive tube, wherein the drive mechanism comprises a motor mechanism comprising a compressional drive spring for axially moving the drive tube and the piston,
wherein the drug delivery device further comprises a connector with an inclined activation tab adapted to engage an inclined surface of the drive tube and impart an initial rotation of the drive tube in the dosing direction, in response to engagement between the activation tab and the drive tube against the biasing force of the compressional drive spring, wherein the stationary state comprises the drive tube can be arranged in a home position, wherein the drive tube can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the guide structure of the drive tube abuts the axial portion of the housing assembly and the helical portion of the guide structure of the housing assembly;
wherein the dosing state comprises:
the drive tube can be arranged in a first dosing position, wherein the drive tube can be arranged in a second axial position and the first angular position, wherein the activation tab engages the drive tube against the biasing force of the compressional drive spring, whereby the drive mechanism is activated, and
a second dosing position, wherein the drive tube can be arranged in an axial position between the first and the second axial position, and an angular position different from the first angular position, wherein the helical portion (189, 289) of the guide structure is slidably arranged at any position along the helical portion (157, 257) of the guide structure of the housing assembly, whereby a dose can be expelled
wherein the drive tube and the piston moves together, when the position of the drive tube is changed from the home position to the first dosing position,
wherein the drive tube can rotate relative to the piston rod, in response to the angular position of the drive tube is changed from the first dosing position to the second dosing position, wherein the change of angular position relative to the housing is induced by the helical guide surface of the housing and the compressional drive spring,
wherein the drive tube at the same time can move together with the piston rod, in response to the axial position of the drive tube is changed from the first dosing position to the home position, wherein the change of axial position relative to the housing is induced by the helical guide surface of the housing and the compressional drive spring,
whereby a fixed dose has been delivered when the drive tube has returned to the home position, in response to activation of the drive mechanism.

In a Further Embodiment

In a further embodiment the drug delivery device comprises an integrated reusable needle with a needle cleaning chamber 120.

In an alternative embodiment the drug delivery device comprises an integrated needle magazine, wherein a plurality of needles First List of Embodiments 1. A drug delivery device (100, 200) for delivering a fixed dose, wherein the drug delivery device comprises:
   a housing assembly,
   a drug reservoir with a piston
   a drive mechanism comprising a piston rod (109, 209) for advancing the piston to expel a drug during dosing, and a drive tube (180, 280) connected to the piston rod (109, 209), wherein the drive tube (180,) is rotatably arranged during dosing and thereby adapted to advance the piston rod (109, 209), wherein the drive mechanism is adapted to deliver the predefined fixed dose in response to activation;
   an activation mechanism for activating the drive mechanism, in response to moving the drive tube in an axial direction,
wherein the housing assembly comprises a guide structure for guiding the drive tube during activation and delivery of a dose, wherein the guide structure comprises an axial portion (156, 256) providing a sliding surface for guiding the drive tube during activation, and for providing a rotational stop defining an end of dose, and a helical portion (157, 257) providing a sliding surface adapted for guiding the drive tube (180, 280) during dosing;
wherein the drive tube (180, 280) comprises a guide structure comprising an axial portion (182, 282) adapted for slidably engaging the axial portion of the housing assembly for activation, and a helical portion (189, 289) for slidably engaging the helical portion of the housing assembly during dosing.

2. The drug delivery device according to embodiment 1, wherein the guide structure (156, 157, 256, 257) of the housing assembly is a closed guide providing a work cycle for the drive tube, and wherein a starting position and an end of dose position of the drive tube is the same.

3. The drug delivery device according to any of the previous embodiments, wherein the housing assembly further comprises an inner tread, wherein the piston rod (109, 209) comprises an outer thread engaging the inner thread of the housing assembly.

4. The drug delivery device according to any of the previous embodiments, wherein the drive tube is axially splined to the piston rod.

5. The drug delivery device according to any of the previous embodiments, wherein the drive mechanism further comprises a motor mechanism for imparting rotation of the drive tube for delivering a dose, in response to activation of the drive mechanism,
wherein the drive tube is axially splined to the piston rod, whereby the drive tube (180, 280) is rotationally locked relative to the piston rod (109, 209),
wherein drive mechanism further comprises a return mechanism for moving the drive tube in an axial direction, and thereby returning the drive tube after activation.

6. The drug delivery device according to any of the previous embodiments, wherein the triggering mechanism comprises a movably arranged connector (170, 270), wherein the connector comprises an activation tab (178, 278), and wherein the activation tab is adapted for engaging a surface portion (183.1, 283.1) of the drive tube, in response to moving the connector in an axial direction, whereby the connector is operatively connected to the drive mechanism and adapted for triggering the drive mechanism, wherein the surface portion (183.1, 283.1) is oriented in a direction towards the activation tab (178, 278).

7. The drug delivery device according to any of the previous embodiments, wherein the drug delivery device comprises:
   a stationary state, wherein the drive tube (180) is arranged in a first axial position and a first angular position, wherein the drive tube is locked to the housing, wherein the guide structure (182, 189, 282, 289) of the drive tube abuts the axial portion (156, 256) of the housing assembly and the helical portion (157, 257) of the guide structure of the housing assembly,
   a first dosing state, wherein the drive tube (180, 280) is arranged in a second axial position and the first angular position, whereby the drive mechanism is activated and
   a second dosing state, wherein the helical portion (189, 289) of the guide structure is slidably arranged along the helical portion (157, 257) of the guide structure of the housing assembly, whereby a dose can be expelled.

8. The drug delivery device according to embodiment 7, wherein the connector (170, 270) is adapted to move the drive tube between the first axial and the second axial position, whereby the drug delivery device (100, 200) is changed from the stationary state to the first dosing state, in response to moving the connector (170, 270) from a first axial to a second axial position, and wherein the drive mechanism is adapted to rotate the drive tube, and thereby change the injection device from the first dosing state, through the second dosing state and to the stationary state, in response to setting the injection device in the first dosing state.

9. The drug delivery device according to any of the previous embodiments, wherein the motor mechanism comprises a torsional drive spring (108, 208) for rotating the drive tube by unwinding, wherein the drive spring (108, 208) is fixed between the housing assembly and the drive tube (180, 280), wherein the drive spring further is compressible for distally moving the drive tube axially during rotation, whereby the drive spring provides the returning mechanism for returning the drive tube after activation.

10. The drug delivery device according to embodiment 9, wherein the drive spring (108, 208) comprises a compressible section (108.4).

11. The drug delivery device according to any of embodiments 9-10, wherein the activation tab (178, 278) comprises a transverse surface portion, and wherein the engageable surface portion (183.1, 283.1) of the drive tube is transverse, whereby initiation of dosing is provided by a rotational movement induced by the torsional drive spring.

12. The drug delivery device according to any of the embodiments 1-8, wherein the motor mechanism comprises a compression drive spring, wherein the activation tab (178, 278) comprises a helical surface portion, wherein the engageable surface portion (183.1, 283.1) of the drive tube for activating the drive tube comprises a helical surface portion, wherein the activation tab is adapted to impart an initial rotation of the drive tube in the dosing direction, in response to engaging the tab (183, 283) and moving the drive tube against the biasing force of the compression spring and between the distal and the proximal position, and wherein the helical portion (157. 257) of the housing assembly and the compression spring is adapted to provide further rotation of the drive tube, in response to the initial rotation, whereby a complete fixed dose can be delivered.

13. The drug delivery device according to any of the previous embodiments, wherein the piston rod (109, 209) comprises an axially extending track (109.2), wherein the drive tube (180, 280) comprises inward protrusions (180.2) adapted to slidably engage the axial track (109.2), whereby the drive tube (180, 280) is rotationally locked relative to the piston rod (109, 210).

14. The drug delivery device according to any of the previous embodiments, wherein the drug delivery device further comprises a shield (110, 210) for operating the connector (170, 270), wherein the shield is adapted to cover a portion of a needle cannula (124) in a distal position, and for exposing the needle cannula in a proximal position, wherein, for the shield being in the proximal position, the needle can be inserted into a subject, and wherein the shield is adapted to move the connector (170, 270) between the first and the second axial position, in response to moving the shield from the distal to the proximal position, wherein the first and the second position of the connector is a distal and a proximal position.

15. The drug delivery device according to embodiment 1 or 2, wherein the piston rod is axially splined to the housing assembly, whereby the piston rod is axially movable and rotationally locked relative to the housing assembly, wherein the drive tube (180, 280) further comprises an inner thread, wherein the piston rod (109, 209) further comprises an outer thread for threadably engaging the inner thread of the drive tube (180, 280), whereby the piston rod is operationally connected to the housing assembly and the drive tube and wherein the piston rod is advanced during rotation, wherein the motor mechanism comprises a compressional drive spring for axially moving the drive tube and the piston, whereby the drive mechanism and the drive-and-return guide are adapted to return the drive tube to the first position.

Second List of Embodiments

1. A drug delivery device (100, 200) for delivering a fixed dose, wherein the drug delivery device comprises:
   a housing assembly,
   a drug reservoir with a piston
   a drive mechanism comprising a piston rod (109, 209) operationally arranged in the housing assembly and adapted for advancing the piston to expel a drug during dosing, and a drive tube (180, 280) operationally arranged with the piston rod (109, 209), wherein the drive tube (180, 280) is adapted to be axially movable relative to the housing assembly and rotationally blocked in a stationary state, and adapted to be axially movable and rotatable relative to the housing in a dosing state, wherein the drive mechanism is adapted for axial movement and rotation of the drive tube (180, 280) in the dosing state and thereby advance the piston rod (109, 209) to deliver the fixed dose in response to activation;

an activation mechanism for activating the drive mechanism, in response to moving the drive tube in an axial direction, wherein the housing assembly comprises a guide structure for guiding the drive tube during activation and delivery of a dose, wherein the guide structure comprises an axial portion (156, 256) providing a sliding surface for guiding the drive tube during activation, and for providing a rotational stop defining an end of dose position, and a helical portion (157, 257) providing a sliding surface adapted for guiding the drive tube (180, 280) during dosing;

wherein the drive tube (180, 280) comprises a guide structure comprising an axial portion (182, 282) adapted for slidably engaging the axial portion of the housing assembly for activation, and a helical portion (189, 289) for slidably engaging the helical portion of the housing assembly during dosing, whereby the drive tube (180, 280) can be guided along the axial portion (156, 256) without rotation and thereby changed from the stationary state to the dosing state during activation, whereby the drive tube (180, 280) can be moved axially and rotated by the drive mechanism in the dosing state, and whereby the drive tube (180, 280) can be guided along the helical portion (189, 289) until the end of dose position and thereby changed from the dosing state to the stationary state, in response to activation of the drive mechanism.

2. The drug delivery device according to embodiment 1, wherein the guide structure (156, 157, 256, 257) of the housing assembly is a closed guide providing a work cycle for the drive tube, and wherein a starting position and an end of dose position of the drive tube is the same.

3. The drug delivery device according to any of the previous embodiments, wherein the housing assembly further comprises an inner tread, wherein the piston rod (109, 209) comprises an outer thread engaging the inner thread of the housing assembly.

4. The drug delivery device according to any of the previous embodiments, wherein the drive tube is axially splined to the piston rod, whereby relative axial movement is allowed and relative rotation is prevented, and whereby the piston rod (109, 209) is advanced in response to rotation of the drive tube (180, 280).

5. The drug delivery device according to any of the previous embodiments, wherein the drive mechanism further comprises a motor mechanism for imparting rotation of the drive tube for delivering a dose, in response to activation of the drive mechanism, wherein the drive tube is axially splined to the piston rod, whereby the drive tube (180, 280) is axially movable and rotationally locked relative to the piston rod (109, 209), wherein drive mechanism further comprises a return mechanism for moving the drive tube in an axial direction, and thereby returning the drive tube after activation.

6. The drug delivery device according to any of the previous embodiments, wherein the triggering mechanism comprises a movably arranged connector (170, 270), wherein the connector comprises an activation tab (178, 278), and wherein the activation tab is adapted for engaging a surface portion (183.1, 283.1) of the drive tube, in response to moving the connector in an axial direction, whereby the connector is operatively connected to the drive mechanism and adapted for triggering the drive mechanism, wherein the surface portion (183.1, 283.1) is oriented in a direction towards the activation tab (178, 278).

7. The drug delivery device according to any of the previous embodiments, wherein the stationary state comprises that the drive tube (180) can be arranged in a home position, wherein the drive tube (180, 280) can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the guide structure (182, 189, 282, 289) of the drive tube abuts the axial portion (156, 256) of the housing assembly and the helical portion (157, 257) of the guide structure of the housing assembly; wherein the dosing state comprises:

the drive tube can be arranged in a first dosing position, wherein the drive tube (180, 280) can be arranged in a second axial position and the first angular position, whereby the drive mechanism is activated and a second dosing position, wherein the drive tube can be arranged in an axial position between the first and the second axial positions, and an angular position different from the first angular position, wherein the helical portion (189, 289) of the guide structure is slidably arranged along the helical portion (157, 257) of the guide structure of the housing assembly, whereby a dose can be expelled.

8. The drug delivery device according to embodiment 7, wherein the connector (170, 270) is adapted to move the drive tube between the first axial and the second axial position, whereby the position of the drive tube (180, 280) is changed from the home position to the first dosing position, in response to moving the connector (170, 270) from a first axial to a second axial position, and wherein the drive mechanism is adapted to rotate the drive tube (180, 280), and thereby change the position of the drive tube (180, 280) from the first dosing position, to the second dosing position and to the home position, in response to activation of the drive mechanism by setting the drive tube (180, 280) in the first dosing position.

9. The drug delivery device according to any of the previous embodiments, wherein the motor mechanism comprises a torsional drive spring (108, 208) for rotating the drive tube by unwinding, wherein the drive spring (108, 208) is fixed between the housing assembly and the drive tube (180, 280), wherein the drive spring further is compressible for moving the drive tube axially during rotation, whereby the drive spring provides the returning mechanism for returning the drive tube after activation.

10. The drug delivery device according to embodiment 9, wherein the drive spring (108, 208) comprises a compressible section (108.4).

11. The drug delivery device according to any of embodiments 9-10, wherein the activation tab (178, 278) of the connector (170, 270) comprises a transverse surface portion, and wherein the engageable surface portion (183.1, 283.1) of the drive tube is transverse, whereby initiation of dosing can be provided by a rotational movement induced by the torsional drive spring, in response to activation of the drive mechanism.

12. The drug delivery device according to any of the embodiments 1-8, wherein the motor mechanism comprises a compression drive spring, wherein the activation tab (178, 278) comprises a helical surface portion, wherein the engageable surface portion (183.1, 283.1) of the drive tube for activating the drive tube comprises a helical surface portion, wherein the activation tab is adapted to impart an initial rotation of the drive tube in the dosing direction, in response to engaging the tab (183, 283) and moving the drive tube against the biasing force of the compression spring and between the distal and the proximal position, and wherein the helical portion (157. 257) of the housing assembly and the compression spring is adapted to provide further rotation of the drive tube, in response to the initial rotation, whereby a complete fixed dose can be delivered.

13. The drug delivery device according to any of the previous embodiments, wherein the piston rod (109, 209) comprises an axially extending track (109.2), wherein the drive tube (180, 280) comprises inward protrusions (180.2) adapted to slidably engage the axial track (109.2), whereby the drive tube (180, 280) is rotationally locked relative to the piston rod (109, 210) and allowed to move axially.

14. The drug delivery device according to any of the previous embodiments, wherein the drug delivery device further comprises a shield (110, 210) for operating the connector (170, 270), wherein the shield is adapted to cover a portion of a needle cannula (124) in a distal position, and for exposing the needle cannula in a proximal position, wherein, for the shield being in the proximal position, the needle can be inserted into a subject, and wherein the shield is adapted to move the connector (170, 270) between the first and the second axial position, in response to moving the shield from the distal to the proximal position, wherein the first and the second position of the connector is a distal and a proximal position.

15. The drug delivery device according to embodiment 1 or 2, wherein the piston rod is axially splined to the housing assembly, whereby the piston rod is axially movable and rotationally locked relative to the housing assembly, wherein the drive tube further comprises an inner thread, whereby the piston rod is operationally arranged in the housing assembly, wherein the piston rod further comprises an outer thread for threadably engaging the inner thread of the drive tube, whereby the piston rod is operationally arranged with the housing assembly and the drive tube and wherein the piston rod is advanced during rotation of the drive tube, wherein the drive mechanism comprises a motor mechanism comprising a compressional drive spring for axially moving the drive tube and the piston,
wherein the drug delivery device further comprises a connector with an inclined activation tab adapted to engage an inclined surface of the drive tube and impart an initial rotation of the drive tube in the dosing direction, in response to engagement between the activation tab and the drive tube against the biasing force of the compressional drive spring, wherein the stationary state comprises the drive tube can be arranged in a home position, wherein the drive tube can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the guide structure of the drive tube abuts the axial portion of the housing assembly and the helical portion of the guide structure of the housing assembly;
wherein the dosing state comprises:
the drive tube can be arranged in a first dosing position, wherein the drive tube can be arranged in a second axial position and the first angular position, wherein the activation tab engages the drive tube against the biasing force of the compressional drive spring, whereby the drive mechanism is activated, and
a second dosing position, wherein the drive tube can be arranged in an axial position between the first and the second axial position, and an angular position different from the first angular position, wherein the helical portion (189, 289) of the guide structure is slidably arranged at any position along the helical portion (157, 257) of the guide structure of the housing assembly, whereby a dose can be expelled
wherein the drive tube and the piston moves together, when the position of the drive tube is changed from the home position to the first dosing position,
wherein the drive tube can rotate relative to the piston rod, in response to the angular position of the drive tube is changed from the first dosing position to the second dosing position, wherein the change of angular position relative to the housing is induced by the helical guide surface of the housing and the compressional drive spring,
wherein the drive tube at the same time can move together with the piston rod, in response to the axial position of the drive tube is changed from the first dosing position to the home position, wherein the change of axial position relative to the housing is induced by the helical guide surface of the housing and the compressional drive spring,
whereby a fixed dose has been delivered when the drive tube has returned to the home position, in response to activation of the drive mechanism.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:
1. A drug delivery device for delivering a fixed dose, wherein the drug delivery device comprises:
  a housing assembly,
  a drug reservoir with a piston
  a drive mechanism comprising a piston rod operationally arranged in the housing assembly and adapted for advancing the piston to expel a drug during dosing, and a drive tube operationally arranged with the piston rod, wherein the drive tube is adapted to be axially movable relative to the housing assembly and rotationally blocked in a stationary state, and adapted to be axially movable and rotatable relative to the housing in a dosing state, wherein the drive mechanism is adapted for axial movement and rotation of the drive tube in the dosing state and thereby advance the piston rod to deliver the fixed dose in response to activation;
  a triggering mechanism for activating the drive mechanism, in response to moving the drive tube in an axial direction,
  wherein the housing assembly comprises a housing guide structure for guiding the drive tube during activation and delivery of a dose, wherein the housing guide structure comprises an axial housing portion providing a first sliding surface for guiding the drive tube during activation, and for providing a rotational stop defining an end of dose position, and a circumferential housing portion providing a second sliding surface adapted for guiding the drive tube during dosing;

wherein the drive tube comprises a drive guide structure comprising an axial drive portion adapted for slidably engaging the corresponding axial housing portion for activation, and a circumferential drive portion for slidably engaging the corresponding circumferential housing portion during dosing, whereby the drive tube can be guided along the axial housing portion without rotation and thereby changed from the stationary state to the dosing state during activation, whereby the drive tube can be moved axially and rotated by the drive mechanism in the dosing state, and whereby the drive tube can be guided along the circumferential housing portion until the end of dose position and thereby changed from the dosing state to the stationary state, in response to activation of the drive mechanism.

2. The drug delivery device according to claim 1, wherein the housing guide structure is a closed guide providing a work cycle for the drive tube, and wherein a starting position and the end of dose position of the drive tube is the same.

3. The drug delivery device according to claim 1, wherein the circumferential portion of the housing guide structure is a helical housing portion, or a stepped housing portion comprising at least one housing step, and wherein the corresponding circumferential drive portion of the drive guide portion is a helical drive portion corresponding to the helical housing portion or a stepped drive portion comprising at least one drive step corresponding to the stepped housing portion.

4. The drug delivery device according to claim 1, wherein the drive tube is axially splined to the piston rod, whereby relative axial movement is allowed and relative rotation is prevented, and whereby the piston rod is advanced in response to rotation of the drive tube.

5. The drug delivery device according to claim 1, wherein the drive mechanism further comprises a motor mechanism for imparting rotation of the drive tube for delivering the dose, in response to activation of the drive mechanism, wherein the drive tube is axially splined to the piston rod, whereby the drive tube is axially movable and rotationally locked relative to the piston rod, wherein the drive mechanism further comprises a return mechanism for moving the drive tube in an axial direction, and thereby returning the drive tube after activation.

6. The drug delivery device according to claim 1, wherein the triggering mechanism comprises a movably arranged connector, wherein the connector comprises an activation tab, and wherein the activation tab is adapted for engaging a surface portion of the drive tube, in response to moving the connector in an axial direction, whereby the connector is operatively connected to the drive mechanism and adapted for triggering the drive mechanism, wherein the surface portion is oriented in a direction towards the activation tab.

7. The drug delivery device according to claim 1, wherein the stationary state comprises that the drive tube can be arranged in a home position, wherein the drive tube can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the drive guide structure abuts the axial housing portion and the helical housing portion of the housing guide structure wherein the dosing state comprises:

the drive tube can be arranged in a first dosing position, wherein the drive tube can be arranged in a second axial position and the first angular position, whereby the drive mechanism is activated and a second dosing position, wherein the drive tube can be arranged in an axial position between the first and the second axial positions, and an angular position different from the first angular position, wherein the helical drive portion is slidably arranged along the helical housing portion, whereby the dose can be expelled.

8. The drug delivery device according to claim 7, wherein a connector is adapted to move the drive tube between the first axial and the second axial position, whereby the position of the drive tube is changed from the home position to the first dosing position, in response to moving the connector from a first axial to a second axial connector position, and wherein the drive mechanism is adapted to rotate the drive tube, and thereby change the position of the drive tube from the first dosing position, to the second dosing position and to the home position, in response to activation of the drive mechanism by setting the drive tube in the first dosing position.

9. The drug delivery device according to claim 1, wherein a motor mechanism comprises a torsional drive spring for rotating the drive tube by unwinding, wherein the drive spring is fixed between the housing assembly and the drive tube, wherein the drive spring further is compressible for moving the drive tube axially during rotation, whereby the drive spring provides a returning mechanism for returning the drive tube after activation.

10. The drug delivery device according to claim 9, wherein the drive spring comprises a compressible section.

11. The drug delivery device according to claim 1, wherein an activation tab of a connector comprises a transverse surface portion, and wherein an engageable surface portion of the drive tube is transverse, whereby initiation of dosing can be provided by a rotational movement induced by a torsional drive spring, in response to activation of the drive mechanism.

12. The drug delivery device according to claim 1, wherein a motor mechanism comprises a compression drive spring, wherein an activation tab comprises a helical tab surface portion, wherein the engageable surface portion of the drive tube for activating the drive tube comprises a helical drive surface portion, wherein the activation tab is adapted to impart an initial rotation of the drive tube in a dosing direction, in response to engaging the activation tab and moving the drive tube against a biasing force of the compression spring and between a distal and a proximal position, and wherein the helical housing portion and the compression spring are adapted to provide further rotation of the drive tube, in response to the initial rotation, whereby a complete fixed dose can be delivered.

13. The drug delivery device according to claim 1, wherein the piston rod comprises an axially extending track, wherein the drive tube comprises inward protrusions adapted to slidably engage the axial track, whereby the drive tube is rotationally locked relative to the piston rod and allowed to move axially.

14. The drug delivery device according to claim 1, wherein the drug delivery device further comprises a shield for operating a connector, wherein the shield is adapted to cover a portion of a needle cannula in a distal shield position, and for exposing the needle cannula in a proximal shield position, wherein, for the shield being in the proximal shield position, the needle can be inserted into a subject, and wherein the shield is adapted to move the connector between a first and a second axial connector position, in response to moving the shield from the distal to the proximal shield position, wherein the first and the second axial connector position is a distal and a proximal connector position.

15. The drug delivery device according to claim 1, wherein the piston rod is axially splined to the housing assembly, whereby the piston rod is axially movable and rotationally locked relative to the housing assembly, wherein the drive tube further comprises an inner thread, whereby the piston rod is operationally arranged in the housing assembly, wherein the piston rod further comprises an outer thread for threadably engaging the inner thread of the drive tube, whereby the piston rod is operationally arranged with the housing assembly and the drive tube and wherein the piston rod is advanced during rotation of the drive tube, wherein the drive mechanism comprises a motor mechanism comprising a compressional drive spring for axially moving the drive tube and the piston,
- wherein the drug delivery device further comprises a connector with an inclined activation tab adapted to engage an inclined surface of the drive tube and impart an initial rotation of the drive tube in a dosing direction, in response to engagement between the activation tab and the drive tube against a biasing force of the compressional drive spring,
- wherein the stationary state comprises the drive tube arranged in a home position, wherein the drive tube can be arranged in a first axial position, wherein the drive tube is allowed to move in one axial direction and blocked by the housing in the other axial direction, and a first angular position, wherein the drive tube is rotationally blocked by the housing in one direction and restricted in the other rotational direction by the drive mechanism, wherein the drive guide structure abuts the axial housing portion and the helical housing portion;

wherein the dosing state comprises:
- the drive tube can be arranged in a first dosing position, wherein the drive tube can be arranged in a second axial position and the first angular position, wherein the activation tab engages the drive tube against the biasing force of the compressional drive spring, whereby the drive mechanism is activated, and
- a second dosing position, wherein the drive tube can be arranged in an axial position between the first and the second axial position, and an angular position different from the first angular position, wherein the helical drive portion is slidably arranged at any position along the helical housing portion, whereby a dose can be expelled wherein the drive tube and the piston move together, when the position of the drive tube is changed from the home position to the first dosing position, wherein the drive tube can rotate relative to the piston rod, in response to the angular position of the drive tube changing from the first dosing position to the second dosing position, wherein the change of angular position relative to the housing is induced by the helical housing portion and the compressional drive spring, wherein the drive tube at the same time can move together with the piston rod, in response to the axial position of the drive tube changing from the first dosing position to the home position, wherein the change of axial position relative to the housing is induced by the helical housing portion and the compressional drive spring, whereby a fixed dose has been delivered when the drive tube has returned to the home position, in response to activation of the drive mechanism.

* * * * *